(12) United States Patent
Shirai et al.

(10) Patent No.: US 9,550,834 B2
(45) Date of Patent: Jan. 24, 2017

(54) METHOD FOR PREPARING GLYCAN-HYDROLYZED ANTIBODY, AND HOMOGENEOUS GLYCOSYLATED ANTIBODY

(71) Applicants: THE NOGUCHI INSTITUTE, Tokyo (JP); IMMUNO-BIOLOGICAL LABORATORIES CO., LTD., Fujioka-shi, Gunma (JP)

(72) Inventors: Takashi Shirai, Tokyo (JP); Masako Mori, Tokyo (JP); Masaki Kurogochi, Tokyo (JP); Masahiro Tomita, Fujioka (JP)

(73) Assignees: THE NOGUCHI INSTITUTE, Tokyo (JP); IMMUNO-BIOLOGICAL LABORATORIES CO., LTD., Fujioka-shi (JP)

( * ) Notice: Subject to any disclaimer, the term of this patent is extended or adjusted under 35 U.S.C. 154(b) by 0 days.

(21) Appl. No.: 14/690,028

(22) Filed: Apr. 17, 2015

(65) Prior Publication Data
US 2016/0032010 A1 Feb. 4, 2016

(30) Foreign Application Priority Data

Apr. 25, 2014 (JP) ................................ 2014-091157
Oct. 31, 2014 (JP) ................................ 2014-222191

(51) Int. Cl.
*C07K 16/32* (2006.01)
*C12Q 1/37* (2006.01)

(52) U.S. Cl.
CPC ................ *C07K 16/32* (2013.01); *C12Q 1/37* (2013.01); *C07K 2317/14* (2013.01); *C07K 2317/21* (2013.01); *C07K 2317/24* (2013.01); *C07K 2317/41* (2013.01); *C07K 2317/732* (2013.01); *C12Y 302/01096* (2013.01); *G01N 2333/924* (2013.01); *G01N 2400/02* (2013.01)

(58) Field of Classification Search
CPC .................................................... C07K 16/32
See application file for complete search history.

(56) References Cited

FOREIGN PATENT DOCUMENTS

WO   WO 2007/133855 A2   11/2007
WO   WO 2013/120066 A1   8/2013

OTHER PUBLICATIONS

Baruah et al. J. Mol. Biol., 2012, 420:1-7.*
Huang et al. JACS, 2012, 134:12308-12318.*
Ishikiriyama et al. J of Bioscience and Bioengineering, 2009, 107(1):67-72.*
Zou et al. JACS, 2011, 133:18975-18991.*
Davies et al. "Expression of GnTIII in a Recombinant Anti-CD20 CHO Production Cell Line: Expression of Antibodies with Altered Glycoforms Leads to an Increase in ADCC Through Higher Affinity for FcγRIII", Biotechnol Bioeng 74: 288-294 (2001).
Goodfellow et al. "An Endoglycosidase with Alternative Glycan Specificity Allows Broadened Glycoprotein Remodelling", J. Am. Chem. Soc., 134, 8030-8033 (2012).
Huang et al. "Chemoenzymatic Glycoengineering of Intact IgG Antibodies for Gain of Functions", J. Am. Chem. Soc., 134, 12308-12318 (2012).
Huang et al. "Glycosynthases Enable a Highly Efficient Chemoenzymatic Synthesis of N-Glycoproteins Carrying Intact Natural N-Glycans", J. Am. Chem. Soc., 131, 2214-2223 (2009).
Krapp et al. "Structural Analysis of Human IgG-Fc Glycoforms Reveals a Correlation Between Glycosylation and Structural Integrity", J Mol Biol 325: 979-989 (2003).
Lifely et al. "Glycosylation and biological activity of CAMPATH-1H expressed in different cell lines and grown under different culture conditions", Glycobiology 5: 813-822 (1995).
Lund et al. "Expression and characterization of truncated forms of humanized L243 IgG1 Architectural features can influence synthesis of its oligosaccharide chains and affect superoxide production triggered through human Fcγ receptor I", Eur J Biochem 267: 7246-7256 (2000).
Mimura et al. "The influence of glycosylation on the thermal stability and effector function expression of human IgG1-Fc: properties of a series of truncated glycoforms", Mol Immunol 37: 697-706 (2000).
Niwa et al. "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma", Cancer Res. 64: 2127-2133 (2004).
Roy Jefferis "Glycosylation as a strategy to improve Antibody-based therapeutics", Nature Review 8: 226-234 (2009).
Shinkawa et al. "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", J. Biol. Chem., Jan. 2003; 278: 3466-3473.
Umana et al. "Engineered glycoforms of an antineuroblastoma IgG1 with optimized antibody-dependent cellular cytotoxic activity", Nat Biotechnol 17: 176-180 (1999).
Weng et al. "Clinical Outcome of Lymphoma Patients After Idiotype Vaccination Is Correlated With Humoral Immune Response and Immunoglobulin G Fc Receptor Genotype", J Clin Oncol, 22 (23) : p. 4717-24 (2004).
Weng et al. "Two Immunoglobulin G Fragment C Receptor Polymorphisms Independently Predict Response to Rituximab in Patients With Follicular Lymphoma", J Clin Oncol, 21 (21) : p. 3940-7 (2003).
Wu et al. "A Novel Polymorphism of FcγRIIIa (CD16) Alters Receptor Function and Predisposes to Autoimmune Disease", J Clin Invest, 100 (5) : p. 1059-70 (1997).
Yamane-Ohnuki et al. "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnol Bioeng 87: 614-622 (2004).

* cited by examiner

*Primary Examiner* — Bin Shen
(74) *Attorney, Agent, or Firm* — Birch, Stewart, Kolasch & Birch, LLP

(57) ABSTRACT

The present invention is aimed to provide a method for preparing an acceptor that is N-glycan hydrolyzed antibody or a Fc fragment thereof used for producing antibody having a homogeneous N-glycan structure; a method for determining a combination of endoglycosidases for use in said preparation; and a method for measuring N-glycans linked to an antibody. The present invention is directed to a method for producing a N-glycan hydrolyzed antibody or Fc fragment thereof, comprising reacting the antibody or the Fc fragment thereof with several endoglycosidases; and a method for determining quantitative information of an objective N-glycan with a desired structure linked to an antibody or a Fc thereof, comprising a protease treatment step and a glycopeptide measurement step, etc.

11 Claims, 25 Drawing Sheets

--PRIOR ART--

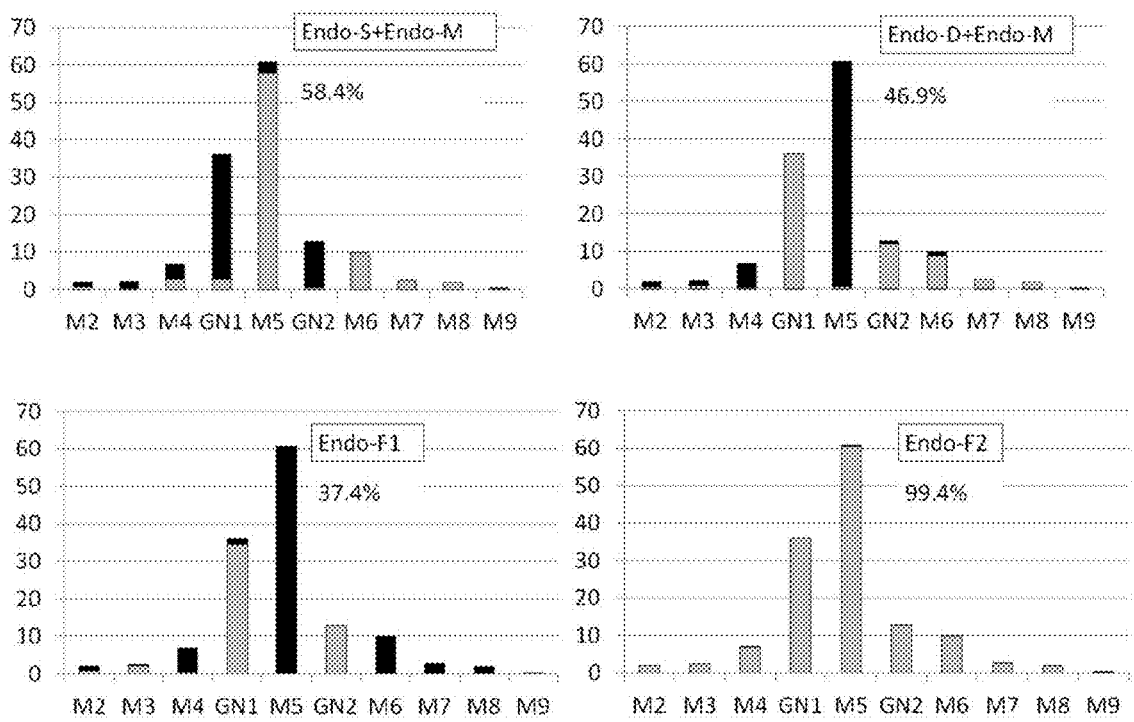

METHOD FOR PREPARING GLYCAN-HYDROLYZED ANTIBODY, AND HOMOGENEOUS GLYCOSYLATED ANTIBODY

CROSS REFERENCE

All publications cited throughout the present application are incorporated herein by reference in their entirety. In addition, the present application claims priority from Japanese Patent Applications Nos. 2014-091157 and 2014-222191 filed on 25 Apr. 2014 and 31 Oct. 2014, respectively. Entire contents of the aforementioned Japanese patent applications which the present application claims priority, are incorporated herein by reference.

TECHNICAL FIELD

The present invention relates to the synthesis of a glycoprotein having a homogeneous N-glycan structure. Specifically, the present invention relates to a newly developed method for preparing an acceptor antibody for remodeling N-glycans in an antibody.

BACKGROUND ART

So-called biotechnology-based pharmaceutical products have been approved, including erythropoietin, or monoclonal antibodies as represented by infliximab, bevacizumab, trastuzumab and adalimumab. These are glycoproteins wherein N-glycans linked to a protein. Immunoglobulin classes of antibodies used in cancer therapy are typically IgG. When the IgG binds to an antigen expressed on a cancer cell, various cascades are turned on to exert anticancer activity which includes 1) antibody-dependent cellular cytotoxicity (ADCC); 2) complement-dependent cytotoxicity (CDC); and 3) a change of signal transduction.

An asparagine at position 297 (N297) in the CH2 domain of the Fc region of an intact Ig antibody is attached to heterogeneous N-glycans. Said N-glycans are mainly biantennary complex type N-glycans having various N-glycan structures. It has been known that this N-glycan is essential for activation of the effector function by an immune complex, and that the activity changes depending on a structure of the N-glycan. For instance, it has been known that lack of α1-6 linked fucose (hereinafter also referred to as a "core fucose") increases ADCC activity mediated by FcγRIIIa (Shinkawa, Toyohide, et al., J. Biol. Chem., January 2003; 278: 3466-3473). It has been reported that the ADCC activity of fucose-depleted trastuzumab is at least 50 times higher than that of core fucose-linked trastuzumab, and the same results have been reported regarding rituximab, anti-CCR4 antibody, etc. (Niwa, Rinpei, et al., Cancer Res. 64: 2127-2133 (2004)).

In general, *Escherichia coli*, which are commonly used as a means for producing biotechnology-based pharmaceutical products, do not attach a N-glycan to a protein. Thus, yeast and the like have been used in the production of antibodies. However, a yeast is considered to be problematic because a yeast does not attach the same N-glycan as human but attaches a so-called high mannose type N-glycan. A method of production using insect cells has been proposed, but the same problems with a yeast is concerned. From these reasons, at present, most of antibody drugs are produced by mammalian cells (CHO cells, NS0 cells, etc.) that are able to attach a human-type N-glycan, but αGal moiety in the N-glycan attached by NS0 cells has antigenicity. It has been known that N-glycans of an antibody produced by CHO cells or the like is biosynthesized by glycosyltransferase, and that a structure and an amount of the made N-glycan changes depending on number of passage even though the same cell line used. Hence, glycoproteins produced by CHO cells or the like have a problem that the glycoproteins are heterogeneous in N-glycan level, although they are homogeneous in an amino acid sequence level. Moreover, it has been reported that types and abundance ratios of a N-glycan structure linked to a Fc of IgG in human serum is completely different from that of a N-glycan structure linked to Fc produced by CHO (Yamane-Ohnuki, N., et al., Biotechnol Bioeng 87: 614-622 (2004)).

In the case of the N-linked glycans, various types of N-glycans exist as combination of various characters such as a high mannose type N-glycan, a biantennary complex type N-glycan and a complex type N-glycan; the presence or absence of sialic acid (Sia); a difference in the linkage manner; the presence or absence of core fucose; the presence or absence of branched N-acetylglucosamine (GlcNAc); and the like. Accordingly, all of commercially available antibody drugs include a large number of N-glycan structures, and their quality maintenance has been an important issue. The heterogeneity of N-glycan structures make it difficult to approve biosimilars as identical ingredients, and erythropolis has been permitted as a different ingredient name such as Epoetin Kappa, for example.

In the study of N-glycan linked to an antibody and its effect on activity or stability of the antibody by using an antibody having truncated N-glycans revealed that the N-glycan has an effect on the structural stability and activity of the CH2 domain (Mimura, Y., et al., MoI Immunol 37: 697-706 (2000), and Krapp, S., et al., J MoI Biol 325: 979-989 (2003)). Furthermore, a N-linked glycan with branched GlcNAc and the removal of core fucose has been known as a example of preferable characteristic of a N-glycan structure for a pharmaceutical. However, most of commercially available antibody drugs include such N-glycans in only several percentages.

These results of analysis on the function of a N-glycan structure in an antibody give rise to need to produce an antibody having a homogeneous N-glycan structure that imparts preferable characteristics as pharmaceuticals to the antibody. Moreover, it has been also desired to produce an antibody having a homogeneous N-glycan structure in order to achieve pharmaceutical grade quality control.

It has been reported that a genetic polymorphism of FcγR influences on ADCC activity, and that among patients administered with rituximab, those with V/V homozygote at the amino acid position 176 of FcγRIIIa has a higher affinity to IgG1 and IgG3 than those with F/F homozygote (Wu, J., et al., J Clin Invest, 100 (5): pp. 1059-70 (1997)). Furthermore, a patient having a homologous chromosome 158V/158V of FcγRIIIa and a patient having a homologous chromosome 131H/131H of FcγRIIa show higher reactivity with rituximab than a patient having a 158F gene of FcγRIIIa or a patient having a 131R gene of FcγRIIa (Weng, W. K. and R. Levy, J Clin Oncol, 21 (21): pp. 3940-7 (2003)). Further, it has been reported that the 158 V/V genotype of FcγRIIIa has a higher progression-free survival rate than V/F and F/F genotypes in vaccine therapy using an anti-idiotype antibody, (Weng, W. K., et al., J Clin Oncol, 22 (23): pp. 4717-24 (2004)). As such, it has been known that the effects of antibody drugs depend on the genetic polymorphism of FcγR. However, there have been no reports regarding a N-glycan structure giving optimal effects depending on the genetic polymorphism of FcγR.

Thus, it has been desired to produce an antibody having a homogeneous N-glycan structure in an analysis of a preferred N-glycan structure.

Various studies have been conducted to control N-glycans linked to an antibody. For example, a truncated antibody has been examined for determining its effect on attachment of a N-glycan to N297 or on structure of N-glycan (Lund, J., et al., Eur J Biochem 267: 7246-7257 (2000)). In addition, it has been reported that a N-glycosylation pattern is different depending on the type of a cell used for production of an antibody (Lifely, M. R., et al., Glycobiology 5: 813-822 (1995)).

Moreover, studies on β (1,4)-N-acetylglucosaminyltransferase III (GnTIII) that catalyzes the formation of branched GlcNAc have been revealed the optimal expression level of GnTIII for the ADCC activity of an antibody (Umana, P., et al., Nat Biotechnol 17: 176-180 (1999)), and that a co-expression of GnTIII in cells producing a large amount of antibody induces production of an antibody having branched GlcNAc, and the antibodies produced thereby kills target cells at 10 to 20 times lower concentrations than the antibodies produced under no expression of GnTIII (Davies, J., et al., Biotechnol Bioeng 74: 288-294 (2001)).

Knockout of α-fucosyltransferase such as FUT8 for removing core fucose has been disclosed (Yamane-Ohnuki, N., et al., Biotechnol Bioeng 87: 614-622 (2004)). However, this method controls only the core fucose and does not provide an antibody having a homogeneous N-glycan structure. The endoglycosidase S (EndoS, Endo-S, or endo-S) (J. J. Goodfellow, B. G. Davis et al. J. Am. Chem. Soc., 134, 8030-8033 (2012)) and a mutant form thereof (W. Huang, Lai-Xi Wang et al, J. Am. Chem. Soc., 134, 12308-12318 (2012), and WO 2013/120066) have been reported as endoglycosidases that hydrolyze N-glycans in an antibody. However, it has been known that these endoglycosidases recognize a N-glycan structure and have specificity to a specific structure of IgG. Hence, EndoS recognize and hydrolyze specific structures of N-glycans linked to antibodies produced by CHO cells, which leads to a problem of remaining antibodies having unreacted N-glycans as impurities. J. J. Goodfellow, B. G. Davis et al. J. Am. Chem. Soc., 134, 8030-8033 (2012) discloses, a method for preparing an acceptor antibody GlcNAc-Asn-Rituxan which is aimed for removing core fucose, wherein Rituxan produced by CHO cells is hydrolyzed by EndoS, which is then reacted with α-fucosidase from bovine for 20 days. However, this method is so complicated that it is not suitable for industrialization.

On the other hand, in the field of glycoengineering on proteins other than antibodies, there have been various reports. Yamane-Ohnuki, N., et al., Biotechnol Bioeng 87: 614-622 (2004) describes that using endo-β-N-acetylglucosaminidase M (endoglycosidase M, Endo-M, or endo-M) in vitro, N-glycan without fucose was attached to insulin not having N-glycan, and a N-glycoprotein, the monocyte chemotactic protein 3 (MCP-3) was synthesized. However, it has been realized that when an antibody is used as a glycoprotein, a N-glycan locates inside the Fc domain and that make it difficult to completely hydrolyze the N-glycan by Endo-M in contrast to other glycoproteins. Alternatively, other report on glycoengineering on proteins except for antibodies includes a method for producing a glycoprotein having a N-glycan of interest by utilizing a transglycosylation reaction of endoglycosidase, wherein N-glycans in the glycoprotein is hydrolyzed with leaving the GlcNAc at a reducing end so as to prepare an acceptor protein, and then a glycosyl donor of interest is attached to the remaining GlcNAc. This method is described to be used as a method for synthesizing a glycoprotein having any desired homogeneous N-glycan structure by using a glycan derivative having a homogeneous N-glycan structure as a donor. (WO 2007/133855). In order to synthesize a glycoprotein having a homogeneous N-glycan structure by applying a glycan remodeling method, it has been considered that at least three techniques, namely, endoglycosidase (mutant Endo-M, etc.), an oxazoline derivative, and a donor substrate are necessary. It has been reported that, by using these techniques, high mannose type N-glycan conjugated to a RNase B protein can be successfully replaced with a biantennary complex N-glycan to synthesize a glycoprotein having a homogeneous N-glycan structure (W. Huang, Cishan Li et al, J. Am. Chem. Soc., 131, 2214-2223 (2009)).

However, in the case of an antibody remodeling as an acceptor protein, there are several problems such as the conformational location of N297 to be inside the Fc domain inhibits the endoglycosidase to approach to the N-glycan, and when α1-6 fucose is coupled to GlcNAc, the N-glycan cannot be hydrolyzed by Endo-M or the like. Due to these problems, the aforementioned glycoengineering method for proteins other than antibodies cannot be directly applied to antibody glycoengineering. Although there are several reports regarding glycoengineering for antibodies (Roy Jefferis, Nature Review 8: 226-234 (2009)), there have been no reports on a production method that is applicable to commercial production of an antibody having a homogeneous N-glycan structure, i.e. having only N-glycans of interest.

SUMMARY OF INVENTION

An object of the present invention is to fulfill the needs over the years that produce an antibody having a homogeneous N-glycan structure with high purity. In one aspect, the present invention is objected to provide a simple method for preparing a glycan-hydrolyzed antibody or a Fc fragment thereof (acceptor), for example, an IgG antibody or a Fc fragment thereof in which N-glycans linked to the asparagines at position 297 are hydrolyzed with remaining N-acetylglucosamines directly linked to the asparagines, which is used for producing an antibody having a homogeneous N-glycan structure. It is also an object of the present invention to provide a simple method for preparing an acceptor antibody, which does not have core fucose for production of an antibody having a homogeneous N-glycan structure. In another aspect, the present invention aims to enable the production of a glycoprotein having a homogeneous human type N-glycan structure and the screening of an effective N-glycan structure. In order to achieve these objects, the present invention provides a simple method for preparing an acceptor by treating an antibody or a Fc fragment thereof (e.g., an antibody produced by animal (cells), yeast, or insect (cells), or a Fc fragment thereof) with a combination of several endoglycosidases.

The protein produced by the conventional protein production method using animal cells does not always give a N-glycan linked to Asn even though the protein has a consensus sequence Asn·X·Ser/Thr, and even in case that the protein has a N-glycan, the N-glycan varies in type and in ratio. Thus, said proteins are a mixture of several hundreds of compounds by considering N-glycan structure. In contrast to this conventional production method, a chemoenzymatic method has been proposed to attempt to obtain an antibody having a homogeneous N-glycan structure. In the conventional methods, the steric hindrance was considered to be a reason for low efficiency of hydrolysis of an antibody-linked N-glycan rather than substrate specificity, usage of several glycosidases has not been attempted to improve hydrolysis efficiency. In Kavitha Baruah et al., J. Mol. Biol. (2012) 420: 1-7, the antibody in the serum has been treated by combination of two types of endoglycosidases, EndoS and EndoH, in order to prevent the serum IgG to inhibit the binding of a monoclonal antibody to a cell surface Fcγ receptor. However Kavitha Baruah et al. does not intend to produce a glycan-hydrolyzed antibody (acceptor), and is silent about N-glycan hydrolysis efficiency by these enzymes. The present inventors have firstly conducted intensive studies regarding a method for providing a homogeneous acceptor and found for the first time that a use of an appropriately selected combination of two or more types of endoglycosidases enables extremely efficient hydrolysis of N-glycans having various structures.

Accordingly, in one aspect, the present invention relates to a method for producing a N-glycans hydrolyzed antibody or a Fc fragment thereof (acceptor), comprising allowing the antibody or the Fc thereof to react with several endoglycosidases. For example, the present invention relates to a method for producing an acceptor from an antibody having different types of N-linked glycans heterogeneously or a Fc fragment thereof (a heterogeneous N-glycan-linked antibody or a Fc fragment thereof), comprising allowing the heterogeneous N-glycan-linked antibody or a Fc fragment thereof to react with several endoglycosidases.

Moreover, the present inventors have conducted various studies about a method for determining a combination of endoglycosidases for efficient N-glycan hydrolysis. Previously, the hydrolyzed characteristics of antibody-linked N-glycans by endoglycosidase have been analyzed by a method of treating the Fc region of IgG with endoglycosidase, and then directly detecting the characteristics by LC-ESI MS (Guozhang Zou et al, J. Am. Chem. Soc., 133, 18975-18991 (2011); Shu-Quan Fan et al, J. Biol. Chem., 287, 11272-11281 (2012)), or by a method of treating an intact antibody with endoglycosidase, then separating the heavy chain of the antibody from the light chain thereof, which is followed by detecting the heavy chain by LC-ESI MS (W. Huang, Lai-Xi Wang et al., J. Am. Chem. Soc., 134, 12308-12318 (2012), WO2013/12006), or the like. However, in such methods, a molecular weight of a detected protein is too large to precisely and quantitatively distinguish molecules, which differs in a molecular weight of a N-glycan (molecular weight: 162 to 1500). In another method, N-glycans linked to an antibody are hydrolyzed by endoglycosidase, and then are labeled with fluorescence to be detected (Kavitha Baruah et al., J. Mol. Biol., 420: 1-7 (2012)). Although, this method enables precise and quantitative measurement of the hydrolyzed sugar moiety, N-glycans linked to (remaining in) an antibody are not detected by this method and it has not been suitable for precise measurement of hydrolysis efficiency.

The present inventors have conducted intensive studies regarding a method for more precisely measuring the amount of N-glycans linked to an antibody or a Fc fragment thereof, and found that a method of treating an antibody with protease to produce a glycopeptide and analyzing the glycopeptide, enables quantitative and simple analysis of N-glycans linked to the antibody. Namely, in one aspect, the present invention relates to a method for determining quantitative information regarding a N-glycan (objective N-glycan) with a given structure linked to an antibody or a Fc thereof, comprising (a) a protease treatment step of treating the antibody or the Fc thereof with protease, and (b) a measurement step of measuring a quantity of glycopeptide having the objective N-glycan among glycopeptides obtained by the protease treatment step.

Further, the present inventors measured the binding of various types of antibodies with a homogeneous N-glycan structure prepared by the above method to FcγRIIIa, and found that a N-glycan structure affects binding activity and some specific N-glycan structures exhibit excellent binding activity. In one aspect, the present invention relates to an antibody having a homogeneous N-glycan structure, and to a pharmaceutical composition comprising said antibody as an active ingredient for treating diseases that can be treated by ADCC activity. The present invention also relates to an antibody having a homogeneous N-glycan structure that is used for treating or preventing diseases that can be treated by ADCC activity.

In the present application, "antibody" is a glycoprotein molecule produced by B cells among lymphocytes in nature, which recognizes and binds to a molecule such as a specific protein (antigen). Antibody is referred to as an immunoglobulin (Ig) as a substance, and corresponds to gamma globulin in plasma. An antibody is divided into several classes (isotypes), depending on a structure of a constant region. In mammals, an antibody is classified into 5 types, i.e. IgG, IgA, IgM, IgD and IgE, depending on a structure of a constant region. The antibody of the present invention may be any of these immunoglobulin classes, and is preferably IgG. In humans, IgG has four subclasses, IgG1 to IgG4, and IgA has two subclasses, IgA1 and IgA2. The antibody of the present invention may be any of these subclasses. In the present application, the term "antibody" is a generic name of the above described classes and subclasses, and further includes non-human antibodies (e.g., antibodies of mammals such as a mouse, a rat, and a rabbit), chimeric antibodies (e.g., a mouse-human chimeric antibody), humanized antibodies, and fully human antibodies. In addition, the antibody may be either a monoclonal antibody or polyclonal antibodies. "Antibody" herein is preferably an IgG antibody linked to two or more different types of N-glycans heterogeneously being a high mannose type, paucimannose type, complex type, hybrid type without core fucose. Alternatively, the antibody of the present application may be an IgG antibody produced by a silkworm, which was introduced with the IgG antibody gene. Examples of the antibody include trastuzumab and Rituxan.

Herein, the "Fc fragment" or "Fc" of an antibody means a constant region (fragment, crystallizable) of an antibody, and is preferably a dimeric Fc, in which two fragments are linked to each other via a disulfide bond or the like.

Herein, the amino acid number in an antibody indicates a number shown by EU Index of Kabat et al. (Kabat et al., Sequences of proteins of Immunological Interest, 1991 Fifth edition).

Herein, the "N-glycan" means a N-glycan that attaches to an antibody as far as such interpretation does not cause inconsistency. In general, a N-glycan attaches to an antibody (antibody-linked N-glycan). The type of a sugar moiety constituting such an antibody-linked N-glycan is not particularly limited and includes glucose, galactose, mannose, fucose, N-acetylglucosamine, N-acetylgalactosamine, N-acetylneuraminic acid, and xylose. In an IgG antibody, a N-glycan attaches to the side chain of asparagine at position 297 via N-acetylglucosamine (N-linked glycan). In an IgG antibody prepared by mammalian cells or the like, a fucose conjugates to the N-acetylglucosamine linked to the side chain of asparagine at position 297, which is called as "core fucose." The number of structures of N-glycans is limited to some extent. A small structural difference in N-glycans is discriminated and precisely recognized to control various life phenomena. The antibody-linked N-glycan has various structures (see, for example, *Seibutsu Kagaku Jikken Ho* (Biochemistry Experimental Methods) 23—*Toutanpaku Tosa Kenkyu Ho* (Glycoprotein Sugar Chain Study Method), Chemical Society of Japan, Scientific Societies Press, edited by Reiko TAKAHASHI (1989)). All N-glycans have a common core structure as shown below. The terminal N-glycan linked to an antibody (the right end in the following structure) is referred to as a "reducing end" and the opposite end (the left end in the following structure) is referred to as a "non-reducing end." The attachment of fucose to the N-acetylglucosamine at the reducing end includes an α1,3 linkage and an α1,6 linkage.

[Formula 1]

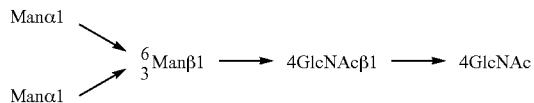

Examples of the antibody-linked N-glycan include: a high mannose type N-glycan, in which only mannose attaches to a non-reducing end of a core structure; a complex type N-glycan, which has one or multiple branches of galactose-N-acetylglucosamine (hereinafter referred to as "Gal-GlcNAc") in parallel on the non-reducing end side of a core structure, and which further has structures such as sialic acid or bisecting N-acetylglucosamine on the non-reducing end side of Gal-GlcNAc; and a hybrid type N-glycan having both branches from a high mannose type N-glycan and a complex type N-glycan on the non-reducing end side of a core structure. Specific examples of the structures of an antibody-linked N-glycan are shown in FIG. 1. In the present description, M2, M3, M4, M5, M6, M7, M8, M9, GN1, GN2 (=G0), G1a, G1b, G2 and A2 mean N-glycans having the structures shown in FIG. 1, or antibodies having said N-glycans. In FIG. 1, a core fucose does not conjugate to the N-glycan structures, however, a core fucose may conjugate to the N-glycans shown as M2, M3, M4, M5, M6, M7, M8, M9, GN1, GN2 (=G0), G1a, G1b, G2 and A2 in this description as far as such interpretation is not inconsistent.

In the present description, the "antibody having a heterogeneous N-glycan structure" means an antibody having N-glycans with two or more different types of structures heterogeneously. The heterogeneous N-glycan-linked antibody herein may be any antibody included in the aforementioned definition of "antibody" as long as N-glycan linked to the antibody are heterogeneous.

In the present description, the "antibody having a homogeneous N-glycan structure" and "homogeneous glycosylated antibody" means the antibody in which N-glycan structures linked to the antibody are identical. An antibody has two N-glycosylation sites and includes: a fully glycosylated type antibody, in which N-glycans conjugate to both of the sites; a hemi-glycosylated type antibody, in which a N-glycan conjugates to either one site; and an aglycosylated type antibody, in which no N-glycans conjugate to the two sites (Shiyi Wang et al., J. Chromatogr. A1217 (2010) 6496-6502). The term "homogeneous (homo)" means that N-glycans conjugating at the two sites have an identical structure. Examples of such a N-glycan structure include M2, M3, M4, M5, M6, M7, M8, M9, GN1, GN2 (=G0), G1a, G1b, G2 and A2. Preferably, the antibody having a homogeneous N-glycan structure is an isolated antibody having a homogeneous N-glycan structure having any one type of N-glycan selected from A2, G2, G0, G1a, G1b and M3. Most preferably, the antibody having a homogeneous N-glycan structure is an antibody having a homogeneous N-glycan structure of A2, G2 or G0. The antibody having a homogeneous N-glycan structure may be preferably trastuzumab having a homogeneous N-glycan structure of A2, G2, or G0. In addition, the antibody of the present invention includes a plurality of antibodies consisting of antibodies substantially having a homogeneous N-glycan structure. Herein, "substantially having a homogeneous N-glycan structure" means that 80% or more (preferably 90% or more, 95% or more, 97% or more, 98% or more, 99% or more, 99.5% or more, and 99.9% or more) of the N-glycan structures of the plurality of antibodies are identical to one another.

In another aspect, the present invention relates to a composition comprising a plurality of (more than one molecule of) antibodies, wherein the antibodies have a substantially identical N-glycan structure. The antibody included in this composition may be either a fully glycosylated type antibody or a hemi-glycosylated type antibody, and is preferably a fully glycosylated type antibody. The phrase "antibodies have a substantially identical N-glycan structure" does not require that other N-glycan structures are not completely present, and other N-glycan structures can be mixed to such an extent that they do not influence on the achievement of an object (e.g., the use of the antibodies as pharmaceutical products, etc.). The phrase "antibodies have a substantially identical N-glycan structure" may means 90%, 95%, 96%, 97%, 98%, 99%, 99.5%, 99.9%, or 99.99% of N-glycans linked to the antibodies of interest are identical to one another in the composition.

In the present description, the "acceptor" means an antibody or a Fc fragment thereof, in which some part of N-glycans linked to the antibody or the Fc fragment are hydrolyzed, or in which N-glycans are hydrolyzed remaining N-acetylglucosamines directly linked to the antibody or the Fc fragment (an antibody or a Fc fragment thereof having only the N-acetylglucosamines). In particular, in a case of IgG, the acceptor means an antibody in which N-glycans linked to the asparagines at position 297 are hydrolyzed remaining N-acetylglucosamines directly linked to the asparagines at position 297, or in other words, an antibody in which only the N-acetylglucosamines are conjugated to the asparagines at position 297. Herein, "only the N-acetylglucosamine" means that sugar moieties consisting the main structure of a N-glycan do not conjugate to the N-acetylglucosamine, but usually core fucose conjugated to the N-acetylglucosamine can be present or absent. As far as such interpretation do not causes inconsistency, "acceptor" may have a core fucose linked to N-acetylglucosamine that directly conjugates to an antibody or a Fc fragment thereof. Preferably, an acceptor does not have core fucose linked to N-acetylglucosamines that directly conjugates to an antibody or a Fc fragment thereof.

In the present invention, the "endoglycosidase" means an enzyme, which hydrolyzes an internal glycoside bond, i.e. an enzyme that cleave N-glycan between the two N-acetylglucosamine residues of the core structure that are not the terminal residue. The endoglycosidase is not particularly limited, as long as it is capable of hydrolyzing N-glycans from an antibody, and preferably is an endoglycosidase classified into EC3.2.1.96. The endoglycosidase of the present invention includes endo-β-N-acetylglucosaminidase D (endoglycosidase D, Endo-D, or endo-D), endo-β-N-acetyl-glucosaminidase H (endoglycosidase H, Endo-H, or endo-H), endoglycosidase S (EndoS, Endo-S, or endo-S), endo-β-N-acetylglucosaminidase M (endoglycosidase M, Endo-M, or endo-M), endo-β-N-acetylglucosaminidase LL (endoglycosidase LL, EndoLL, Endo-LL, or endo-LL), endo-β-N-acetylglucosaminidase F1 (endoglycosidase F1, Endo-F1, or endo-F1), endo-β-N-acetylglucosaminidase F2 (endoglycosidase F2, Endo-F2, or endo-F2), and endo-β-N-acetylglucosaminidase F3 (endoglycosidase F3, Endo-F3, or endo-F3).

The "ADCC" means a mechanism whereby a target coated with an antibody is damaged by a cell having a Fc receptor that recognizes the Fc portion of the antibody. The "ADCC activity" means the ability (activity) of an antibody to exert cytotoxicity due to ADCC in binding to a target. It is considered that the ADCC activity mainly depends on the binding activity of the Fc region of an antibody to a Fc receptor.

The "Fc receptor" is a receptor specific to the Fc region of an antibody, which includes FcγRI (CD64), FcγRII-A (CD32), FcγRII-B2 (CD32), FcγRII-B1 (CD32), FcγRIIIa (CD16a), FcγRIIIb (CD16b), FcεRI, and FcαRI (CD89). Fc receptors are known for its ligand of classes of antibodies, and specifically FcγRI binds to IgG3, IgG1 and IgG4, FcγRII binds to IgG3 IgG1, and IgG2, and that FcγRIII binds to IgG1 and IgG3. The Fc receptor herein is preferably FcγRIII because almost all ADCC are known to be mediated by natural killer cells having a Fc receptor FcγRIII on the cell surface. As described above, FcγRIIIa is known to have several variants. The FcγRIIIa herein may be any of these variants, and preferably is FcγRIIIa (FcγRIIIa-V158) having valine as an amino acid at position 158.

The "diseases that can be treated by ADCC activity" are not particularly limited as long as that can be treated by binding antibodies to target cells and then destroying the antibody coated target cells by cytotoxic cells such as natural killer cells. The diseases can be selected depending on the target of the antibody. Examples of such diseases include protozoal, bacterial or viral infectious diseases, cancers, and parasitic infections. When the antibody is trastuzumab, the target disease is breast cancer or stomach cancer.

In another aspect, the present invention relates to a pharmaceutical composition comprising a said antibody as an active ingredient. The type of the pharmaceutical composition is not particularly limited, and a formulation includes a tablet, a capsule, a granule, a powder agent, syrup, a suspending agent, a suppository, an ointment, a cream, a gel, a patch, an inhaler, and an injection. These formulations can be prepared according to ordinary methods. A liquid preparation may be in a form, which is dissolved or suspended in water or another suitable solvent at time of use. A tablet and a granule may be coated according to well-known methods. An injection is prepared by dissolving the compound of the present invention in water or physiological saline or glucose solution as necessary, which can be added buffer or preservative. The pharmaceutical composition can be provided in any appropriate preparation form for oral administration or parenteral administration. The pharmaceutical composition can be prepared as that for oral administration, such as a granule, a fine grain agent, a powder agent, a hard capsule, a soft capsule, syrup, an emulsion, a suspending agent or a liquid agent; or that for parenteral administration, such as an injection for intravenous administration, intramuscular administration or subcutaneous administration, a drop, a transdermal absorption agent, a transmucosal absorption agent, a nasal drop, an inhaler, or a suppository. An injection or a drop can be prepared in a powdery form such as a freeze-dried form which may be dissolved in a suitable aqueous medium such as a physiological saline at time of use.

Advantageous Effects of Invention

According to the production method of the present invention, an acceptor antibody can be prepared efficiently. Moreover, the present invention enables to obtain an efficient combination of endoglycosidases to hydrolyze N-glycans, and to efficiently produce an acceptor antibody at low costs. Further, the antibody having a homogeneous N-glycan structure of the present invention can be superior in attachment to a Fc receptor and can provide an excellent therapeutic agent for diseases that can be treated by ADCC activity.

BRIEF DESCRIPTION OF DRAWINGS

FIG. 7C includes graphs showing the amount (pmol) of an antibody-linked N-glycan with each structure per 10 μg of mouse IgG1 produced by the silk gland of silkworm treated or untreated with various endo-glycosidases or a combination thereof (Endo-F3, Endo-F1+Endo-F2, Endo-F1+Endo-F3, and Endo-F2+Endo-F3). The black bar shows the amount of a N-glycan with indicated structure before treatment with endoglycosidase, and the grey bar shows that after treatment with endoglycosidase. The longitudinal axis indicates pmol/10 μg IgG1, and the horizontal axis indicates N-glycan structure. The percentage in the table indicates the amount of the remaining N-glycan.

MODE FOR CARRYING OUT THE INVENTION

Method for Producing Antibody

Figure 1:
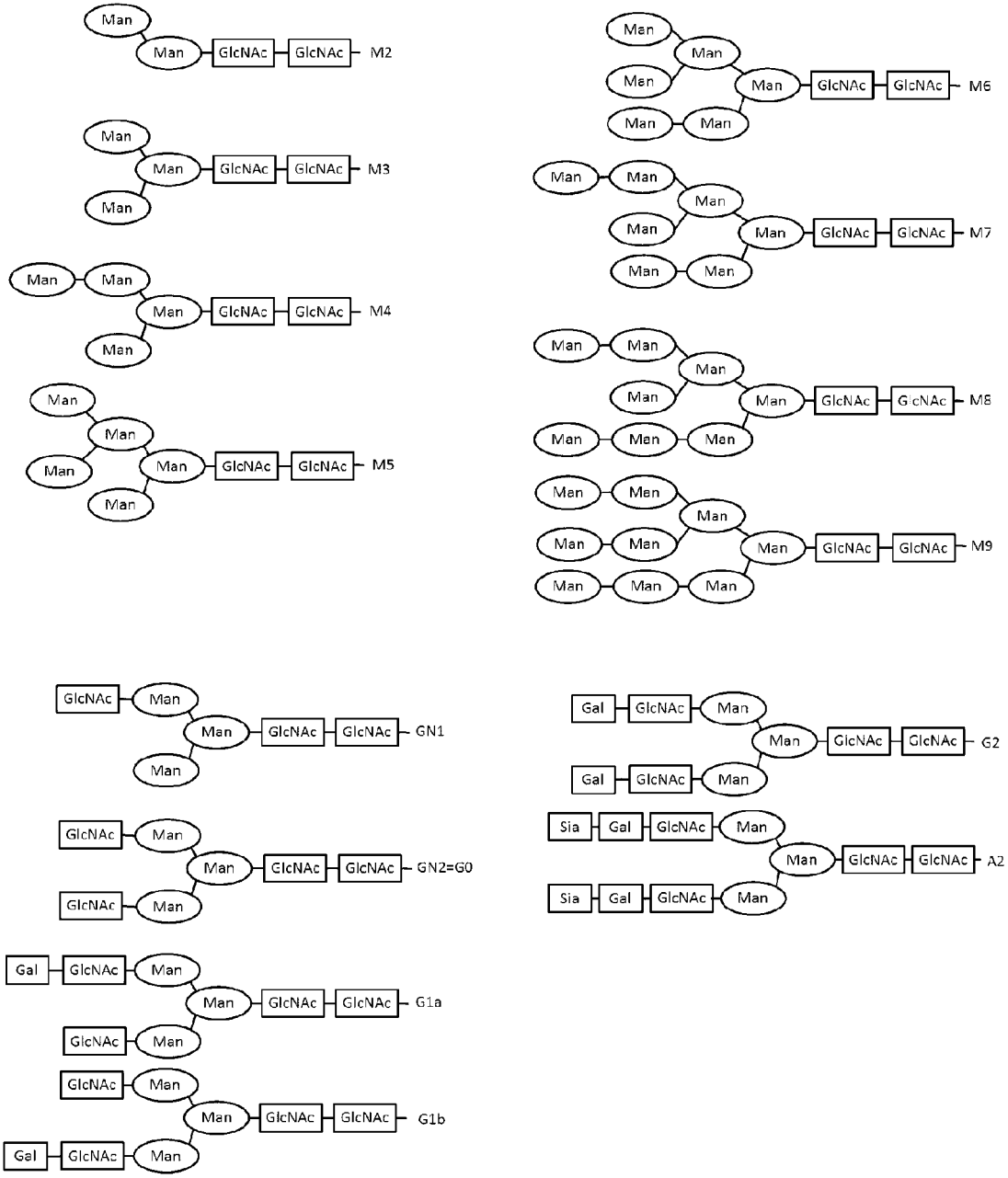
FIG. 1 illustrates examples of N-glycan structures. The abbreviations indicate the following sugars: GlcNAc: N-acetylglucosamine, Man: mannose, Gal: galactose, and Sia: sialic acid.

An antibody can be produced by a genetic recombination technique well known in the art. Specifically, the antibody can be obtained by inserting an antibody gene into a vector and introducing the antibody expression vector into silkworm, yeast, etc. For example, the antibody can be obtained by the following method: isolating cDNAs of the heavy chain and light chain of an antibody; adding the 5'-untranslated region sequence of BmNPV polyhedrin to the 5'-terminus of each of the heavy chain and light chain cDNAs by PCR using a primer comprising a 5'-untranslated region sequence of BmNPV polyhedrin (Japanese Patent publication No. 2008-125366A); inserting obtained heavy chain cDNA into the NruI site of a silkworm transformation vector pMSG3.1 MG (Japanese Patent publication No. 2012-182995A); and preparing a plasmid vector for introducing the antibody cDNA into silkworm by inserting the light chain cDNA into the Eco47III site of the vector.

The obtained plasmid vector is purified by Plasmid Midi Kit (QIAGEN) and then mixed with a helper plasmid pHA3PIG (Nat. Biotechnol. 18, 81-84 (2000)) in an amount ratio of 1:1, which is precipitated with ethanol, and is then dissolved in an injection buffer (0.5 mM phosphate buffer pH 7.0, 5 mM KCl) to obtain a DNA concentration of 10 to 1000 μg/ml. The mixed vector solution is injected into a silkworm egg at the blastodermic phase that is two to eight hours after oviposition (silkworm embryo) in a trace amount of liquid (approximately 1 to 200 nl per egg). The trace amount vector DNA injected egg is incubated at approximately 25° C., and the hatched silkworm is raised. The obtained reproductive adult worms are mated, so as to obtain egg mass of F1 generation. Eggs of transgenic silkworms emitting green fluorescence from their eyes or nerve systems are selected from egg mass on the 3rd to 10th day after oviposition, which is hatched to establish transgenic silkworms that are introduced with the antibody cDNA.

The obtained transgenic silkworm is mated with a silkworm expressing an IE1 gene that is a transactivator derived from BmNPV (Japanese Patent publication No. 2012-182995A). Silkworms having both the antibody cDNA and the IE1 gene are selected from obtained silkworms of F2 generation and are raised to make cocoons. The cocoons of silkworms including both the antibody cDNA and the IE1 gene are immersed in an extraction buffer (PBS, 0.1% Triton X-100, 0.5 M NaCl), which is stirred for 30 minutes at room temperature to prepare a cocoon extract. The extract is filtrated through a 0.45-μm filter, which is then subjected to a protein G column (Protein G Sepharose 4 Fast Flow, GE Healthcare). The antibody is eluted with 0.1 M glycine (pH 2.7), and is then added 1 M Tris (pH 9.0) for neutralization, followed by a dialysis against PBS.

An Fc fragment of the antibody can be prepared by various methods well known in the art. For example, the antibody obtained by the above method can be treated with papain to produce a Fc fragment.

<Method for Quantifying Antibody-Linked N-Glycan>

In one aspect, the present invention relates to a method for determining quantitative information of a N-glycan of a desired structure (an objective N-glycan) linked to an antibody or a Fc fragment thereof, wherein the method comprises (a) a protease treatment step comprising treating the antibody or the Fc fragment thereof with protease, and (b) a measurement step comprising measuring an amount of glycopeptides to which the objective N-glycan conjugate to glycopeptides obtained by the protease treating step.

The method of the present invention can be used, in particular, for the purpose of obtaining quantitative information regarding an antibody-linked N-glycan that remains after the hydrolysis of N-glycans by endoglycosidase. Specifically, the present invention relates to a method for determining quantitative information of a N-glycan of a desired structure linked to an antibody or a Fc fragment thereof that is treated with desired endoglycosidases (an objective N-glycan), wherein the method comprises (a) a reaction step comprising reacting the antibody or the Fc fragment thereof with endoglycosidases, (b) a protease treatment step comprising treating the obtained antibody or the Fc fragment thereof with protease after the reaction step, (c) a measurement step comprising measuring a glycopeptide having the objective N-glycan among glycopeptides obtained by the protease treating step, and a determination of the quantitative information of the objective N-glycan linked to the antibody or the Fc thereof treated with the endoglycosidases based on the measured value of the glycopeptide having the objective N-glycan.

In the above described method for quantifying an antibody-linked N-glycan, the "objective N-glycan" means a N-glycan having a desired structure that conjugates to an antibody or a Fc fragment thereof, which is intended to obtain quantitative information. The objective N-glycan may be one type or two or more types of N-glycans. Two or more types of objective N-glycans having different structures can be measured simultaneously or separately to determine the quantitative information thereof. The above method for quantifying an antibody-linked N-glycan, the "quantitative information" means information reflecting the amount of a N-glycan linked to an antibody (or that remaining after hydrolysis by endoglycosidases). The "quantitative information" is not particularly limited, as long as that can indicate an amount, and may mean an (absolute) amount or a relative numerical value such as a numerical value or a ratio relative to a threshold or a control, or staged evaluation (indicating a large to small amount). The "quantitative information" generally means information of the amount of one type of objective N-glycan. However, when there are two or more types of objective N-glycans, the quantitative information may be quantitative information regarding each N-glycan, or may also be quantitative information regarding all of the two or more types of N-glycans (e.g., the total amount of antibody-linked objective N-glycans, etc.).

The protease used in the above described "protease treatment step" is not particularly limited, as long as it is capable of hydrolyzing an antibody and does not have an influence on a structure of a N-glycan linked to the antibody, and for example, can be trypsin. The treatment with protease can be carried out by a method well known in the art depending on the types and optimal conditions (pH, temperature, etc.) of used protease. The "reaction step" of reacting an antibody or a Fc fragment thereof with endoglycosidase can be carried out by a method well known in the art depending on the type and optimal conditions (pH, temperature, etc.) of used endoglycosidase. For instance, the treatment with endoglycosidase can be carried out by adding endoglycosidase to an antibody or a Fc fragment thereof in a 50 mM sodium phosphate buffer solution (pH 6.0 to 8.0), and then incubating the mixture at 37° C. for 1 to 30 hours. In the "reaction step", one type of endoglycosidase can be used, or alternatively two or more types of endoglycosidases can be used in combination. The measurement of a glycopeptide in the above "measurement step" can be carried out by the method described below.

Furthermore, determination of quantitative information of a N-glycan having a desired structure linked to an antibody or a Fc fragment thereof (an objective N-glycan) can be carried out by determining quantitative information based on the measured value obtained from the measurement step depending on the properties of the quantitative information and on the measurement method applied in the measurement step. For instance, determination of quantitative information can be carried out by directly determining the measured value obtained in the measurement step (a measured value itself such as fluorescence intensity, or the amount of a N-glycan-linked antibody calculated as a result of the measurement) as quantitative information. Otherwise, determination of quantitative information can be carried out by calculating, evaluating, or classifying the measured value obtained from the measurement step. For instance, quantitative information may be determined as the ratio of the amount of an objective N-glycan-linked antibody to a total amount of the antibodies, or as the amount of an objective N-glycan-linked antibody that exceeds or does not exceed a specific threshold. Alternatively, determination of quantitative information may be the ratio of the amount of objective N-glycans linked to an evaluated antibody or a Fc fragment thereof to that to a control antibody or a Fc fragment thereof, or a difference between the amount of objective N-glycans linked to a control antibody or a Fc fragment thereof and that linked an antibody to be evaluated or a Fc fragment thereof.

A glycopeptide having an objective N-glycan is derived from the above antibody or the Fc thereof that is treated with endoglycosidase, and thus has the same N-glycan as that linked to the antibody or the Fc fragment thereof. Accordingly, the amount of a glycopeptide having an objective N-glycan reflects the amount of the antibody or the Fc fragment thereof having an objective N-glycan that is treated with endoglycosidases. In the determination step that comprises determining the quantitative information of the objective N-glycan that attaches to the antibody or the Fc thereof treated with the endoglycosidases from the measured value of the glycopeptide having the objective N-glycan, the measured value of the glycopeptide having the objective N-glycan may be directly determined as quantitative information of the objective N-glycan linked to the antibody or the Fc thereof treated with endoglycosidases, or may be obtained by calculation based on the measured value of the glycopeptide having an objective N-glycan. For example, when the measured value of the glycopeptide having an objective N-glycan is based on amount, the obtained amount can be directly determined as the amount of the objective N-glycan linked to the antibody or Fc fragment thereof treated with endoglycosidases.

<Method for Determining Information Regarding Amount of Antibody-Linked N-Glycan Hydrolyzed>

In one aspect, the present invention relates to a method for determining information of the amount of an antibody-linked N-glycan hydrolyzed by endoglycosidases. Specifically, the present invention relates to a method for determining information of the amount of an objective N-glycan linked to an antibody or a Fc fragment thereof hydrolyzed by endoglycosidases, wherein the objective N-glycan is one type of N-glycan having a desired structure, comprising:
(a) a reaction step comprising reacting the antibody or the Fc fragment thereof with endoglycosidases,
(b) a protease treatment step comprising treating the antibody or the Fc thereof reacted with endoglycosidases with protease to produce a glycopeptide,
(c) a protease treatment step comprising treating the antibody or the Fc thereof not reacted with endoglycosidases with protease to produce a glycopeptide,
(d) a quantification step comprising quantifying the glycopeptide having objective N-glycan obtained from the protease treatment step comprising treating the antibody or the Fc thereof reacted with endoglycosidases with protease,
(e) a quantification step comprising quantifying the glycopeptide having objective N-glycan obtained from the protease treatment step comprising treating the antibody or the Fc thereof no reacted with endoglycosidases with protease, and
(f) a determination step comprising determining information of the amount of the objective N-glycan hydrolyzed by endoglycosidases from the quantitative values obtained in the quantification steps for the antibody or the Fc thereof reacted with endoglycosidases and for the antibody or the Fc thereof not reacted with endoglycosidases.

In another aspect, the method for determining information of hydrolyzed amount of an antibody-linked N-glycan of the present invention may be a method for determining information of the hydrolyzed amount of two or more types of objective N-glycans in an antibody having a heterogeneous N-glycan structure. The present invention includes a method for determining information of a hydrolyzed amount of two or more types of objective N-glycans of desired structure that heterogeneously linked to an antibody or a Fc thereof by endoglycosidases, wherein the method comprises:
(a) a reaction step comprising reacting the antibody or the Fc thereof with endoglycosidases,
(b) a protease treatment step comprising treating the antibody or the Fc thereof reacted with endoglycosidases with protease to produce a glycopeptide,
(c) a protease treatment step comprising treating the antibody or the Fc thereof not reacted with endoglycosidases to produce a glycopeptide,
(d) a quantification step comprising quantifying the glycopeptide having objective N-glycan obtained from the protease treatment step comprising treating the antibody or the Fc thereof reacted with endoglycosidases with protease,
(e) a quantification step comprising quantifying the glycopeptide having objective N-glycan obtained from the protease treatment step comprising treating the antibody or the Fc thereof no reacted with endoglycosidases with protease, and
(f) a determination step comprising determining information of the amount of each of the objective N-glycan hydrolyzed by endoglycosidases from the quantitative values obtained in the quantification steps for the antibody or the Fc thereof reacted with endoglycosidases and for the antibody or the Fc thereof not reacted with endoglycosidases.

In the above described method for determining information of the hydrolyzed amount of an antibody-linked N-glycan, the "information of the hydrolyzed amount of an antibody-linked N-glycan hydrolyzed by endoglycosidases" is not particularly limited, as long as that can be an indicator for the amount of the antibody-linked N-glycan hydrolyzed by endoglycosidases. Thus, it may mean an (absolute) amount or a relative numerical value such as a numerical value or a ratio relative to a threshold or a control, or staged evaluation (indicating a large to small amount). When there are two or more types of objective N-glycans, the "quantitative information" may mean quantitative information of each N-glycan, or it may also mean quantitative information of all of the N-glycans (e.g., the total hydrolyzed amount, etc.). Otherwise, the "quantitative information" may also be a "N-glycan hydrolyzed pattern" that is an aggregation of quantitative information of the hydrolyzed amounts of individual N-glycans for N-glycans having two or more types of structures.

Descriptions regarding the "protease treatment step," the "reaction step," and the "measurement step" in the aforementioned "method for quantifying an antibody-linked N-glycan" can be directly applied to the "method for determining information of hydrolyzed amount of an antibody-linked N-glycan." In the "method for determining information regarding the hydrolyzed amount of an antibody-linked N-glycan", the "protease treatment step" and/or the "measurement step" for the antibody or the Fc thereof not reacted with endoglycosidases may be conducted at the same time with those steps for the antibody or the Fc thereof reacted with endoglycosidases, or may be carried out separately at different time. The aforementioned "method for quantifying an antibody-linked N-glycan" may not comprise the "protease treatment step" and/or the "measurement step" for the antibody or the Fc thereof not reacted with endoglycosidases, and the predetermined quantitative value of the antibody or the Fc thereof not reacted with endoglycosidases can be used in the determination step instead.

Determination of information of the amount of a N-glycan having a desired structure that attaches to an antibody or a Fc fragment thereof (objective N-glycan) hydrolyzed by endoglycosidases can be achieved by calculating the hydrolyzed amount based on the measured value obtained in the measurement step depending on the properties of the information of the hydrolyzed amount and the measurement method applied. For instance, determination of the information of the hydrolyzed amount can be carried out by calculating the ratio of endoglycosidases-treated/endoglycosidases-untreated by endoglycosidases or a difference ((endoglycosidase untreated group)–(endoglycosidase treated group)) of the measured value obtained in the measurement step (a measured value itself such as fluorescence intensity, or the amount of a N-glycan-linked antibody calculated from the measurement). Otherwise, determination of the information of the hydrolyzed amount can be carried out by evaluating or classifying from the measured value obtained in the measurement step. For instance, such information of the hydrolyzed amount may be determined as the ratio or difference of the objective N-glycans treated/untreated by endoglycosidases that exceeds/not-exceed a specific threshold.

In particular, when objective N-glycans have two or more types of structures, the ratio of endoglycosidases-treated/endoglycosidases-untreated by endoglycosidases or a difference ((endoglycosidase untreated group)–(endoglycosidase treated group)) can be calculated for an individual N-glycan having each structure, and then the information of the amount of N-glycans hydrolyzed by endoglycosidases can be determined as an aggregation of these information (hydrolysis pattern).

<Method for Determining Combination of Endoglycosidases for Preparation of Acceptor>

In a further aspect, the present invention relates to a method for determining a combination of two or more types of endoglycosidases for preparing an acceptor. Specifically, the present invention relates to a method for determining a combination of two or more types of endoglycosidases which is suitable for hydrolyzing N-glycans linked to an antibody, comprising:

a step of determining information of the hydrolyzed amount of two or more types of objective N-glycans having a desired structure that heterogeneously attach to an antibody or a Fc thereof by endoglycosidases by applying the above method for determining information of the hydrolyzed amount of an antibody-linked N-glycan, a step of selecting a combination of two or more types of endoglycosidases showing complementary N-glycan hydrolysis from the obtained information of the hydrolyzed amount of objective N-glycans by endoglycosidases, and a step of determining the selected two or more types of endoglycosidases as a combination of endoglycosidases suitable for cleaving the N-glycans linked to the antibody.

In the method for determining a combination of endoglycosidases for preparation of an acceptor, the "step of selecting a combination of two or more types of endoglycosidases showing complementary N-glycan hydrolysis" can be carried out as follows: a candidate endoglycosidase that hydrolyzes a large amount of N-glycans of one or more types of structures (referred to as a "candidate hydrolyzed N-glycan") and that hydrolyzes a small amount of other N-glycans having one or more types of structures (referred to as a "candidate non-hydrolyzed N-glycan") is selected, then an endoglycosidase that hydrolyzes a large amount of the candidate non-hydrolyzed N-glycan is selected as a complementary endoglycosidase, and a combination of the candidate endoglycosidase and the complementary endoglycosidase can be selected as a "combination of two or more types of endoglycosidases showing complementary N-glycan hydrolysis." The "step of determining the selected two or more types of endoglycosidases as a combination of endoglycosidases suitable for hydrolyzing the N-glycans linked to the antibody" can be carried out by determining the above combination of the candidate endoglycosidase and the complementary endoglycosidase as a combination suitable for hydrolyzing the N-glycans linked to the antibody. In selection of endoglycosidases and determination of a combination thereof, several endoglycosidases can be selected as candidate endoglycosidases, or several endoglycosidases can be selected as complementary endoglycosidases, so that the determined combination of endoglycosidases includes three or more types of endoglycosidases. Furthermore, as combinations of candidate endoglycosidases and complementary endoglycosidases, two or more combinations may be determined. As a candidate endoglycosidase initially selected, a desired endoglycosidase can be selected. Preferably, it is an endoglycosidase that hydrolyzes a large amount of antibody-linked N-glycan. The hydrolyzed amount of an antibody-linked N-glycan by endoglycosidases can be determined by the method described above for determining information regarding the hydrolyzed amount of an antibody-linked N-glycan.

Alternatively, the "step of selecting a combination of two or more types of endoglycosidases showing complementary N-glycan hydrolysis" may be carried out by comparing hydrolysis patterns of N-glycans having multiple structures obtained for individual endoglycosidases, and then determining a combination of endoglycosidases so that the N-glycan hydrolysis patterns are complementary to one another.

Further, in the method for determining a combination of endoglycosidases for preparation of an acceptor, two or more combinations of two or more types of endoglycosidases showing complementary N-glycan hydrolysis may be determined, and then those combinations of the endoglycosidases are used in the above "method for determining information of the hydrolyzed amount of an antibody-linked N-glycan" to determine information of the hydrolyzed amount of N-glycans having desired types of structures, which is followed by comparing the determined information of the hydrolyzed amount of N-glycans to determine an appropriate combination of endoglycosidases for preparation of an acceptor. The above method may further comprises a step of determining information of the hydrolyzed amount of objective N-glycans hydrolyzed by the said two or more types of endoglycosidases showing complementary N-glycan hydrolysis (this step comprises, as necessary, a reaction step, a protease treatment step, and/or a quantification step by using said two or more types of endoglycosidases showing complementary N-glycan hydrolysis) and a step of determining a combination that hydrolyzes a large amount of objective N-glycans as a combination of endoglycosidases for preparation of an acceptor from said two or more combination of two or more types of endoglycosidases showing complementary N-glycan hydrolysis. Herein, the phrase "that hydrolyzes a large amount of objective N-glycans" means that the total hydrolyzed amount of one or more types of objective N-glycans or the total hydrolyzed amount of all of the linked N-glycans is large.

Specifically, the method for determining a combination of endoglycosidases for preparation of an acceptor of the present invention may be the following method: a method for determining a combination of two or more types of endoglycosidases suitable for hydrolyzing N-glycans linked to an antibody, comprising:

a step of determining information of the hydrolyzed amount of two or more types of objective N-glycans of a desired structure that heterogeneously attaches to an antibody or a Fc thereof by endoglycosidases, by applying the above method for determining information of the hydrolyzed amount of an antibody-linked N-glycan, a step of selecting two or more combinations of two or more types of endoglycosidases showing complementary N-glycan hydrolysis from the obtained information of the hydrolyzed amount of objective N-glycans by endoglycosidases, a step of determining information of the hydrolyzed amount of objective N-glycans for each of the selected two or more combinations of two or more types of endoglycosidases, by applying the above method for determining information of the hydrolyzed amount of an antibody-linked N-glycan, and a step of comparing the information of the hydrolyzed amounts of the objective N-glycans to determine a combination of two or more types of endoglycosidases suitable for hydrolyzing N-glycans linked to an antibody.

In the above, the "information of the hydrolyzed amount of an objective N-glycan" may mean a hydrolysis pattern, the total hydrolyzed amount of one or more types of objective N-glycans, or the total hydrolyzed amount of all of the linked N-glycans. In this case, the step of determining a combination of two or more types of endoglycosidases suitable for hydrolyzing N-glycans linked to an antibody can be carried out, for example, by comparing the total hydrolyzed amount of all of the N-glycans, (one or more types of) N-glycans that attaches to an endoglycosidase-untreated antibody or a Fc fragment thereof in large amounts, or specific (one or more types of) objective N-glycans of interest between tested combinations of two or more types of endoglycosidases, and then determining the combination that cleaves all of N-glycan in larger amount, that hydrolyzes (one or more types of) N-glycans that attach to endoglycosidase-untreated antibody or Fc fragment thereof in larger amounts, or that hydrolyzes the specific (one or more types of) objective N-glycans of interest in larger amount, respectively, as a combination of two or more types of endoglycosidases suitable for hydrolyzing N-glycans linked to the antibody.

In using the total hydrolyzed amount is used as an indicator in the above determination step, the method of the present invention can further comprise a step of determining information of the hydrolyzed amount of all N-glycans, one or more types of objective N-glycans, and/or (one or more types of) N-glycans that attaches to an endoglycosidase-untreated antibody or a Fc fragment thereof in large amounts, by the two or more types of endoglycosidases showing complementary N-glycan hydrolysis, and a step of determining a combination of two or more types of endoglycosidases showing complementary N-glycan hydrolysis that hydrolyzes larger in a total amount as a combination of endoglycosidases for hydrolyzing the N-glycans linked to the antibody.

<Method for Measuring Glycopeptide>

A quantification step comprising quantifying a glycopeptide having each N-glycan structure obtained by the above described protease treatment step can be carried out by mass spectrometry.

A composition ratio of an antibody-linked N-glycan can be analyzed by acid hydrolysis using trifluoroacetic acid or the like to separate neutral hexose or hexosamine, specifically by using a carbohydrate composition analyzer (BioLC) manufactured by Dionex. The BioLC is a device for analyzing a sugar composition by applying a HPAEC-PAD (high performance anion-exchange chromatography-pulsed amperometric detection) method [Journal of Liquid Chromatography (J. Liq. Chromatogr.), 6, 1577 (1983)]. Also, a composition ratio can be analyzed by a fluorescence labeling method using 2-aminopyridine. Specifically, a sample is acid hydrolyzed by well known methods [Agricultural and Biological Chemistry (Agric. Biol. Chem.), 55 (1): 283-284 (1991)], and labeled with fluorescence by 2-aminopyridylation, which is then analyzed by HPLC to calculate the composition ratio.

The structural analysis of a N-glycan linked to an antibody can be carried out by a two-dimensional N-glycan mapping method [Analytical Biochemistry (Anal. Biochem.), 171, 73 (1988), *Seibutsu Kagaku Jikken Ho* (Organic Chemistry Experimental Methods) 23—*Toutanpaku Tosa Kenkyu Ho* (Glycoprotein Sugar Chain Study Method), Chemical Society of Japan, Scientific Societies Press, edited by Reiko TAKAHASHI (1989)]. The two-dimensional N-glycan mapping method can estimate a N-glycan structure by plotting the X axis as the retention time or elution position of a N-glycan in reverse phase chromatography, and the Y axis as the retention time or elution position of a N-glycan in normal phase chromatography, and comparing the obtained results with the results of the known N-glycans.

Specifically, a N-glycan is released from an antibody by anhydrous hydrazine treatment, which is then labeled with 2-aminopyridine (hereinafter abbreviated as "PA") [Journal of Biochemistry (J. Biochem.), 95, 197 (1984)] and separated from an excessive amount of 2-aminopyridylation reagent or the like by gel filtration, followed by reverse phase chromatography. Subsequently, each of the peaks of the fractionated N-glycans are subjected to normal phase chromatography. A N-glycan structure can be estimated by plotting the obtained results on a two-dimensional N-glycan map, and comparing with Oligosaccharide Standard (manufactured by TaKaRa) or a publication [Analytical Biochemistry (Anal. Biochem.), 171, 73 (1988)]. Moreover, the structure of each N-glycan estimated by said two-dimensional N-glycan mapping can be confirmed by mass spectrometry using MALDI-TOF-MS or the like.

<Method for Preparing Acceptor>

In another aspect, the present invention relates to a method of for preparing an acceptor by hydrolyzing N-glycans linked to an antibody. Specifically, the present invention relates to a method for producing a N-glycans hydrolyzed antibody (e.g., in the case of an IgG antibody, an antibody in which N-glycans linked to the side chain of asparagine at position 297 are hydrolyzed except for N-acetylglucosamine at the reducing terminal), comprising reacting the antibody with several endoglycosidases. Herein, several endoglycosidases may be two or more types of endoglycosidases selected from the group consisting of endoglycosidase D, endoglycosidase H, endoglycosidase S, endoglycosidase M, endoglycosidase LL, endoglycosidase F1, endoglycosidase F2, and endoglycosidase F3.

A combination of two or more types of endoglycosidases used in the method of the present invention may include a desired combination of endoglycosidases. For example, several endoglycosidases can be a combination of endoglycosidases having different substrate specificity that are classified into EC3.2.1.96. Preferably, the combination of endoglycosidases is a combination determined by the above method.

For example, a combination of two or more types of endoglycosidases used in the method of the present invention includes the following combinations:
(i) endoglycosidase D and endoglycosidase S,
(ii) endoglycosidase S and endoglycosidase LL,
(iii) endoglycosidase D and endoglycosidase LL,
(iv) endoglycosidase D and endoglycosidase H,
(v) endoglycosidase S and endoglycosidase H,
(vi) endoglycosidase F1 and endoglycosidase F2,
(vii) endoglycosidase F1 and endoglycosidase F3,
(iii) endoglycosidase F2 and endoglycosidase F3,
(iX) endoglycosidase D, endoglycosidase S and endoglycosidase LL,
(X) endoglycosidase D, endoglycosidase S and endoglycosidase H, and
(Xi) endoglycosidase D, endoglycosidase S and endoglycosidase F1.

In one aspect, the present invention relates to a method for preparing an acceptor (preferably, an antibody linked to an only N-acetylglucosamine (e.g., in the case of an IgG antibody, an antibody linked to an only N-acetylglucosamine at the asparagine at position 297) or a Fc fragment thereof) from antibodies to which two or more different types of N-linked glycans heterogeneously attach (heterogeneous N-glycan-linked antibody) or Fc fragments thereof, comprising reacting the heterogeneous N-glycan-linked antibody (e.g., IgG antibody) or a Fc fragment thereof with several endoglycosidases, wherein said several endoglycosidases are determined by the above method for determining a combination of endoglycosidases for preparation of an acceptor. In other words, the present invention relates to a method for preparing an acceptor (preferably, a N-glycans hydrolyzed antibody remaining N-acetylglucosamine, or a Fc fragment thereof), comprising reacting the antibody with several endoglycosidases determined by the above method.

It has been a problem of the N-glycan engineering on an antibody that 80% or more of antibodies comprise core fucoses when said antibodies are produced by CHO cells, and that endoglycosidase digestion cannot make acceptors. In order to solve this problem, preferably an antibody produced by yeast or silkworm can be used as a starting material in the above method to prepare an acceptor without core fucose (e.g., an IgG antibody linked to an only N-acetylglucosamine at the asparagine at position 297, or a Fc fragment thereof) more simply and inexpensively. Specifically, the present invention relates to a method for preparing an acceptor for production of a glycoprotein having a homogeneous N-glycan structure, comprising reacting an antibody produced by yeast or silkworm or a Fc fragment thereof with several endoglycosidases. In particular, by using several endoglycosidases, an acceptor can be prepared from a high mannose type N-glycan-linked antibody or a Fc fragment thereof particularly produced by yeast or silkworm.

<Method for Preparing Homogeneous N-Glycan-Linked Antibody>

Further, the present invention provides a method for preparing a homogeneous glycosylated antibody or a Fc fragment thereof by using the acceptor prepared by the above described method. Specifically, the present invention relates to a method for preparing an antibody having a desired homogeneous N-glycan structure (a homogeneous N-glycan-linked antibody) or a Fc fragment thereof, comprising:

an acceptor preparation step comprising preparing an acceptor by the above method, and an antibody generation step comprising reacting obtained acceptor with a glycosyl donor by using glycosynthase to synthesize an antibody or a Fc fragment thereof having the desired homogeneous N-glycan structure.

Otherwise, the present invention relates to a method for preparing an antibody or a Fc fragment thereof introduced homogeneous N-glycans (the "A-GlcNAc-antibody" in the following formula), comprising reacting the acceptor prepared by the above method (the "GlcNAc-antibody" in the following formula) and a glycosyl donor (the "A-GlcNAc-Oxa" in the following formula) derivatized from the homogeneous oligosaccharide (A-GlcNAc-OH) with oxazoline, by enzymatic transglycosylation using glycosynthase. Herein, the term "antibody" includes a Fc fragment of the antibody.

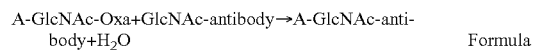

Formula (wherein A represents oligosaccharides, and GlcNAc-Oxa represents an oxazoline derivative of GlcNAc.)

A N-glycan linked to said homogeneous N-glycan linked antibody can have a desired structure, and may be, for example, a high mannose type N-glycan (any one of M3, M4, M5, M6, M7, M8, and M9) or a complex type N-glycan (any one of A2, G2, G1a, G1b, and G0 (=GN2)).

The above described antibody remodeling step can be carried out by a method well known in the art, for example, by adding a dehydration condensation material to a glycosyl donor in the presence of a supplementation material, and then adding an acceptor antibody thereto and glycosynthase to catalyze.

The pharmaceutical composition of the present invention can be used in an oral administration form or a parenteral administration form such as an injection or a drop. When the present compound is administered to mammals, it may be orally administered in the form of a tablet, a powder agent, a granule or syrup, or it may also be parenterally administered in the form of an injection or a drop.

The pharmaceutical composition of the present invention can be formulated according to an ordinary method using a pharmaceutically acceptable general carrier. When a solid preparation for oral administration is prepared, an excipient, and as necessary, a binder, a disintegrator, a lubricant and the like are added to a main agent, and thereafter, a solvent, a granule, a powder agent, a capsule or the like can be prepared according to an ordinary method. When an injection is prepared, a pH adjuster, a buffer, a stabilizer, a solubilizer and the like are added to a main agent, as necessary, and thereafter, a subcutaneous or intravenous injection can be prepared according to an ordinary method.

In another aspect, the present invention relates to a method for treating or preventing diseases that can be treated by ADCC activity, comprising administering an effective amount of the antibody of the present invention to a patient in need thereof. Otherwise, the present invention relates to a use of the antibody of the present invention for producing a therapeutic or preventive agent for diseases that can be treated by ADCC activity. For example, when the antibody of the present invention is used for therapeutic or preventive purpose, the antibody of the present invention can be administered in an oral administration form, or a parenteral administration form such as an injection or a drop. The dose applied when the antibody of the present invention is administered to a mammal or the like is different depending on symptoms, age, sex, body weight, administration form, etc. For example, when the antibody of the present invention is orally administered to an adult, the dose per day can be set at generally 0.1 to 1000 mg, and such a dose can be administered one to five times per day.

Hereinafter, the present invention will be described more in detail in the following examples. However, these examples are not intended to limit the scope of the present invention.

EXAMPLES

Example 1

Preparation of EndoLL (1) Cloning DNA of EndoLL

The amino acid sequence of *Lactococcus lactis* that produces a protein having an amino acid sequence showing high homology with a partial amino acid sequence of a known endo-β-N-acetylglucosaminidase was searched using NCBI blastp, and primers were then designed based on the corresponding genomic sequence. The primer sequences of sense and antisense primers are shown below.

```
EndoLL-12F (sense primer)
                               (SEQ ID NO: 3)
5' ttggaggattttatgaaaaaatcg 3'

EndoLL stopR (antisense primer)
                               (SEQ ID NO: 4)
5' tcagctatttttttgtcctaatacttg 3'
```

Using gDNA extracted from *Lactococcus lactis* (Accession No. MAFF516032) deposited in the National Institute of Agrobiological Sciences (2-1-2 Kannondai, Tsukuba, Ibaraki 305-8602, Japan) as a template, PCR was carried out with the aforementioned primers, and the amplified 2.8-kbps fragment was then separated and cleaved by 0.8% agarose gel electrophoresis. Thereafter, it was then purified using Wizard SV Gel and PCR Clean-up System (Promega). Using this DNA fragment as a template, PCR was further carried out with the following sense and antisense primers.

```
6P1-EndoLL-F (sense primer)
                               (SEQ ID NO: 5)
5' gggcccctgggatccaaaaaatcgaaaaaa 3'

6P1-EndoLL-R (antisense primer)
                               (SEQ ID NO: 6)
5' atgcggccgctcgagttagctatttttttg 3'
```

Figure 2:
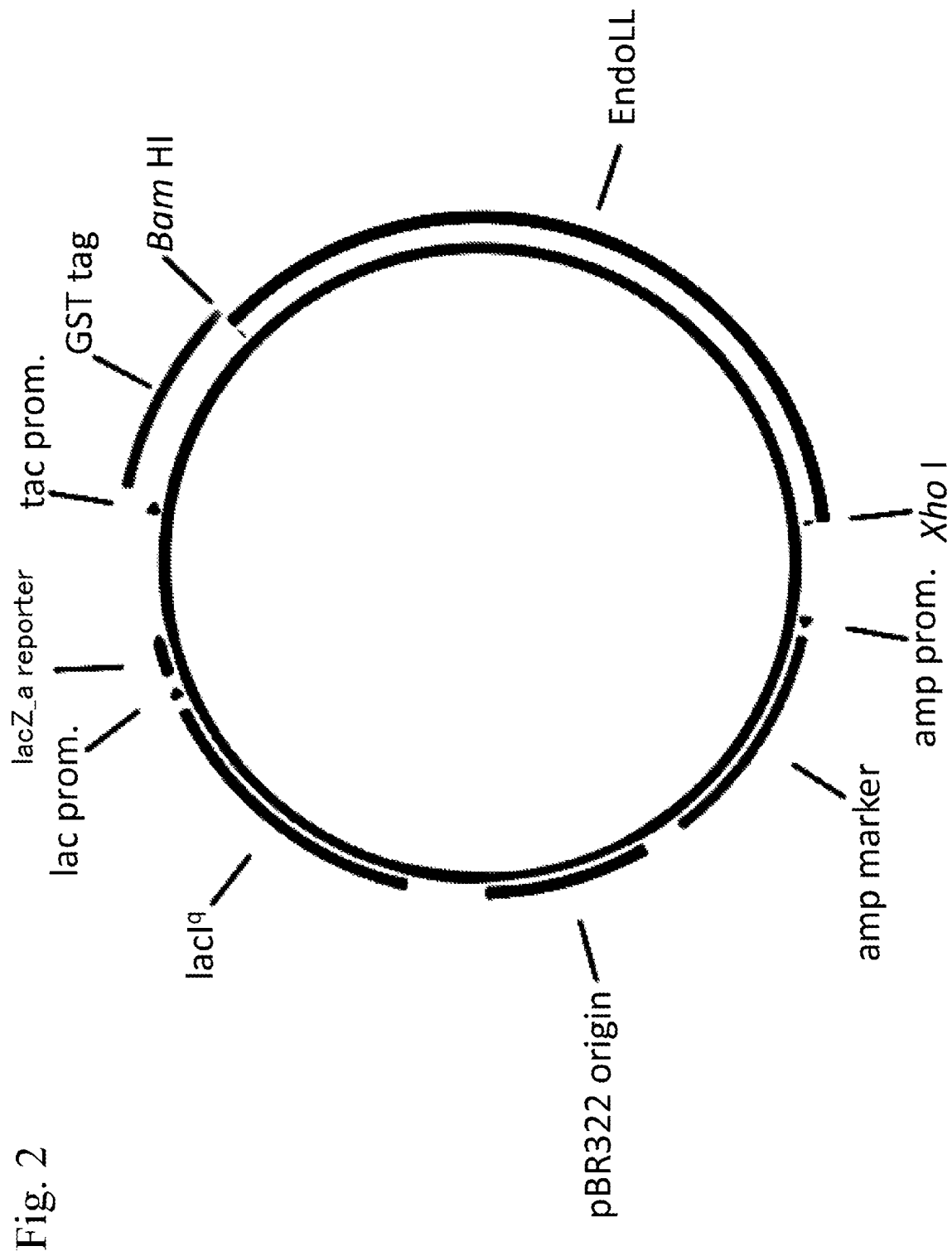
FIG. 2 illustrates a plasmid EndoLL/pGEX-6P-1.

The amplified 2.8-kbps fragment was separated and cleaved by 0.8% agarose gel electrophoresis, and it was then purified using Wizard SV Gel and PCR Clean-up System (Promega). Using this fragment and a linear pGEX-6P-1 vector cleaved by BamHI and XhoI, a plasmid EndoLL/pGEX-6P-1 was constructed employing In-Fusion HD Cloning Kit (Clontech) (FIG. 2).

The produced EndoLL was sequenced using an automatic nucleotide sequencing machine (manufactured by Applied Biosystems, 3730x1 DNA analyzer). The nucleic acid sequence thereof is shown in SEQ ID NO: 1.

(2) Expression of EndoLL in *Escherichia coli*

*Escherichia coli* BL-21 (DE3) strain was used as a host. Transformation was carried out according to the method of Inoue H, et al., Gene, 96, 23-28 (1990). Selection was carried out on a LB agar medium, to which carbenicillin had been added to a concentration of 50 µg/ml. Thereafter, growing colonies were inoculated in a LB liquid medium, to which carbenicillin had been added to a concentration of 50 µg/ml, and it was then cultured at 37° C. At the time point at which OD600 reached 0.8, the culture solution was quenched, and IPTG was added thereto to give a final concentration of 50 µg/ml. The culture solution was subjected to rotary shaking culture at 20° C. overnight, and thereafter, cells were collected.

The collected cell mass was suspended in a NETN buffer solution (50 mM Tris buffer solution pH 8.0, 150 mM sodium chloride, 1 mM EDTA, and 1% NP-40), and it was then subjected to ultrasonic disintegration using QSonica, Q125 (WAKENBTECH CO, LTD.). The thus disintegrated solution was centrifuged, and GST-Accept (Nacalai Tesque) gel was then added to a separated supernatant. The obtained mixture was subjected to rotary shaking culture at 4° C. for 2 hours, and GST-fused EndoLL was then recovered by affinity chromatography. Gel on which the GST-fused EndoLL had been adsorbed was washed with a NETN buffer solution, and was further washed with a NET buffer solution (50 mM Tris buffer solution pH 8.0, 150 mM sodium chloride, and 1 mM EDTA). To the thus washed gel, into which an equal amount of the NET buffer solution had been added, Turbo3C protease was added, and the obtained mixture was then subjected to rotary shaking culture at 4° C. overnight. Thereafter, the culture captured on the resin was subjected to enzyme digestion. A supernatant obtained after the enzyme digestion was recovered, and it was defined as purified EndoLL.

The nucleic acid sequence encoding the obtained EndoLL is shown in SEQ ID NO: 1, and the amino acid sequence thereof is shown in SEQ ID NO: 2.

Example 2

Production of Mouse IgG1 by Silk Gland of Silkworm (1) Production of Vector The cDNAs of the heavy chain and light chain of mouse IgG1 were isolated from mouse hybridomas. Subsequently, PCR was carried out using primers comprising a 5'-untranslated region sequence of BmNPV polyhedrin (Japanese Patent Laid-Open No. 2008-125366), so that the 5'-untranslated region sequence of BmNPV polyhedrin could be added to the 5'-terminus of each of the heavy chain and light chain cDNAs. The obtained heavy chain cDNA of mouse IgG1 was inserted into the NruI site of a silkworm transformation vector pMSG3.1 MG (Japanese Patent Laid-Open No. 2012-182995), and thereafter, the light chain cDNA was inserted into an Eco47III site thereof, so as to complete a plasmid vector to be used for incorporation of mouse IgG1 cDNA into a silkworm.

(2) Production of Transgenic Silkworm

The above described plasmid vector was purified with Plasmid Midi Kit (QIAGEN), and it was then mixed with a helper plasmid pHA3PIG (Nat. Biotechnol. 18, 81-84 (2000)), so that the plasmid amount ratio became 1:1. Thereafter, the mixture was subjected to ethanol precipitation, and was then dissolved in an injection buffer (0.5 mM phosphate buffer pH 7.0, and 5 mM KCl), resulting in a DNA concentration of 200 µg/ml. This vector mixed solution was injected into a silkworm egg (silkworm embryo) that was in the blastodermic phase 2 to 8 hours after oviposition, in a trace amount of liquid of approximately 15 to 20 nl per egg.

The egg, into which such a trace amount of the vector DNA had been injected, was inoculated at 25° C., and the hatched silkworm was then raised. The obtained reproductive adult worms were mated to obtain an egg mass of F1 generation. The F1 egg mass on the 5th to 6th day after the oviposition day was observed under a fluorescence stereoscopic microscope, so that the eggs of transgenic silkworms emitting green fluorescence from the eyes or the nerve systems were screened. Silkworms hatched from the eggs emitting green fluorescence were raised, so that transgenic silkworms, into which the mouse IgG1 cDNA had been incorporated, could be established.

The above described transgenic silkworms were mated with silkworms that express an IE1 gene as a BmNPV-derived transactivator (Japanese Patent Laid-Open No. 2012-182995). It has been known that an IE1 protein synthesized from the IE1 gene acts on a BmNPV-derived hr3 enhancer or a sericin 1 promoter comprised in pMSG3.1 MG, and it increases the expression level of a recombinant protein in the middle silk gland (Biotechnol. Bioeng. 106, 860-870 (2010)). From the silkworms of F2 generation obtained as a result of the mating, silkworms having both the mouse IgG1 cDNA and the IE1 gene were selected, and the selected silkworms were then raised and allowed to produce cocoons.

(3) Purification of Mouse IgG1

Cocoons produced by the silkworms having both the mouse IgG1 cDNA and the IE1 gene were immersed in an extraction buffer (PBS, 0.1% Triton X-100, and 0.5 M NaCl), and the obtained solution was then stirred for 30 minutes at room temperature to prepare a cocoon extract. The extract was filtrated through a 0.45-μm filter, and was then subjected to a protein G column (Protein G Sepharose 4 Fast Flow, GE Healthcare). For elution of IgG1 from the column, a 0.1 M glycine-HCl buffer solution (pH 2.7) was used. 1 M Tris (pH 9.0) was added to the eluted IgG1 solution so as to neutralize it, and finally, the solution was dialyzed against PBS.

Example 3

Preparation of Acceptor of Mouse IgG1 Produced from Silkworm Silk Gland by Simultaneous Hydrolysis with EndoS, EndoLL and EndoD, and Confirmation by SDS-PAGE Mouse IgG1 (1 mg) produced by the silk gland of silkworms, and EndoS (2 μg), EndoLL (2 μg) and Remove-iT Endo-D ((NEB) 150 units) were added to a 50 mM sodium phosphate buffer solution (pH 7.5) to a total amount of 500 μl and the obtained mixture was then left at rest at 37° C. for 17 hours. To this reaction solution, 75 μl of Ab-Capcher ExTra (ProteNova Co., Ltd.) that had been equilibrated with a 50 mM sodium phosphate buffer solution (pH 7.5) was added, and the thus obtained mixture was then subjected to rotary shaking at room temperature for 3 hours, so that the antibody was captured on the gel carrier. The operation to wash the carrier with 450 μl of PBS for 5 minutes three times in total, and 150 μl of a 0.1 M glycine-HCl buffer solution (pH 2.7) was then added to the resulting carrier. The resulting solution was shaken at room temperature for 5 minutes for elution, and 2.5 μl of a 1 M Tris-HCl buffer solution (pH 9.0) was then added to the eluted solution, so as to neutralize it. This elution operation was carried out three times in total, and the eluted solutions were gathered. The eluted solution was concentrated with Amicon Ultra-0.5 (NMWL 30 kDa), and was then substituted with PBS. 0.5 μg out of the obtained 965 μg of mouse IgG1 acceptor was aligned with the same amount of mouse IgG1 before being subjected to simultaneous hydrolysis, and was then electrophoresed by 10% SDS-PAGE, so that the molecular weight thereof was examined.

Figure 3:
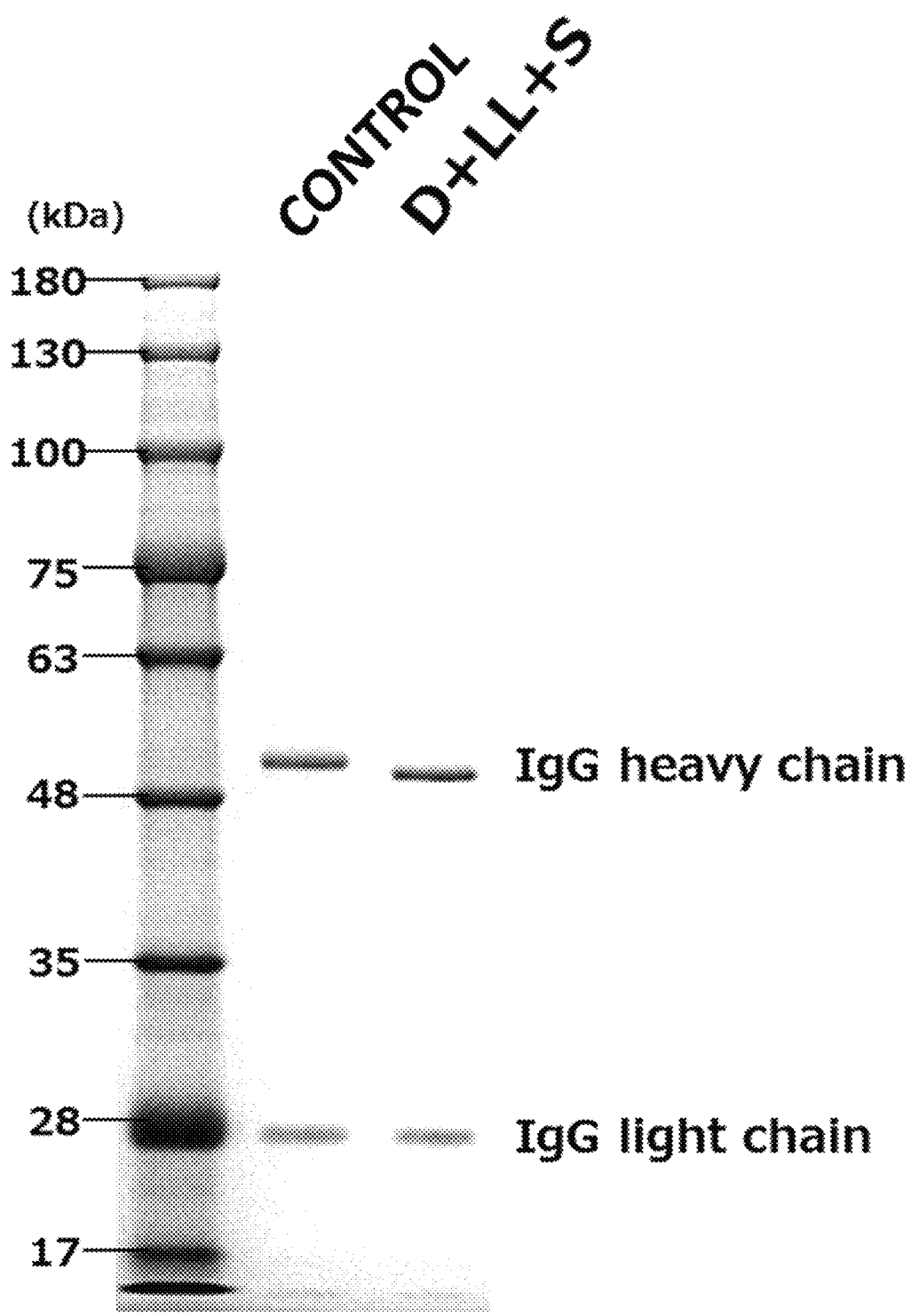
FIG. 3 is a photograph of SDS-PAGE performed on mouse IgG1 produced by the silk gland of silkworm, which was not digested or was digested with endoglycosidases of EndoS, EndoLL and Endo-D.

It was confirmed that the acceptor was shifted to a low molecular weight side because N-glycans were hydrolyzed, and that there were almost no unreacted N-glycans (FIG. 3).

Example 4

Confirmation of Hydrolysis of Mouse IgG1 by Endoglycosidase by SDS-PAGE

Mouse IgG1 (4 μg) produced by the silk gland of silkworms, and each glycosidase (1 μg) of EndoS, EndoLL, Remove-iT Endo-D, Endo-H (NEB) or Endo-M (Tokyo Chemical Industry Co., Ltd.), were added into a buffer solution to a total amount of 20 μl. The obtained mixture was reacted at 37° C. for 6 hours. When EndoS, EndoLL or Remove-iT Endo-D was used, a 50 mM sodium phosphate buffer solution (pH 7.5) was used as a buffer solution. When Endo-H was used, a 50 mM sodium citrate buffer solution (pH 5.5) was used as a buffer solution, and when Endo-M was used, a 50 mM sodium phosphate buffer solution (pH 6.0) was used as a buffer solution. After the reaction, the mouse IgG1 (0.5 μg) was electrophoresed by 10% SDS-PAGE, and the molecular weight thereof was examined.

Figure 4:
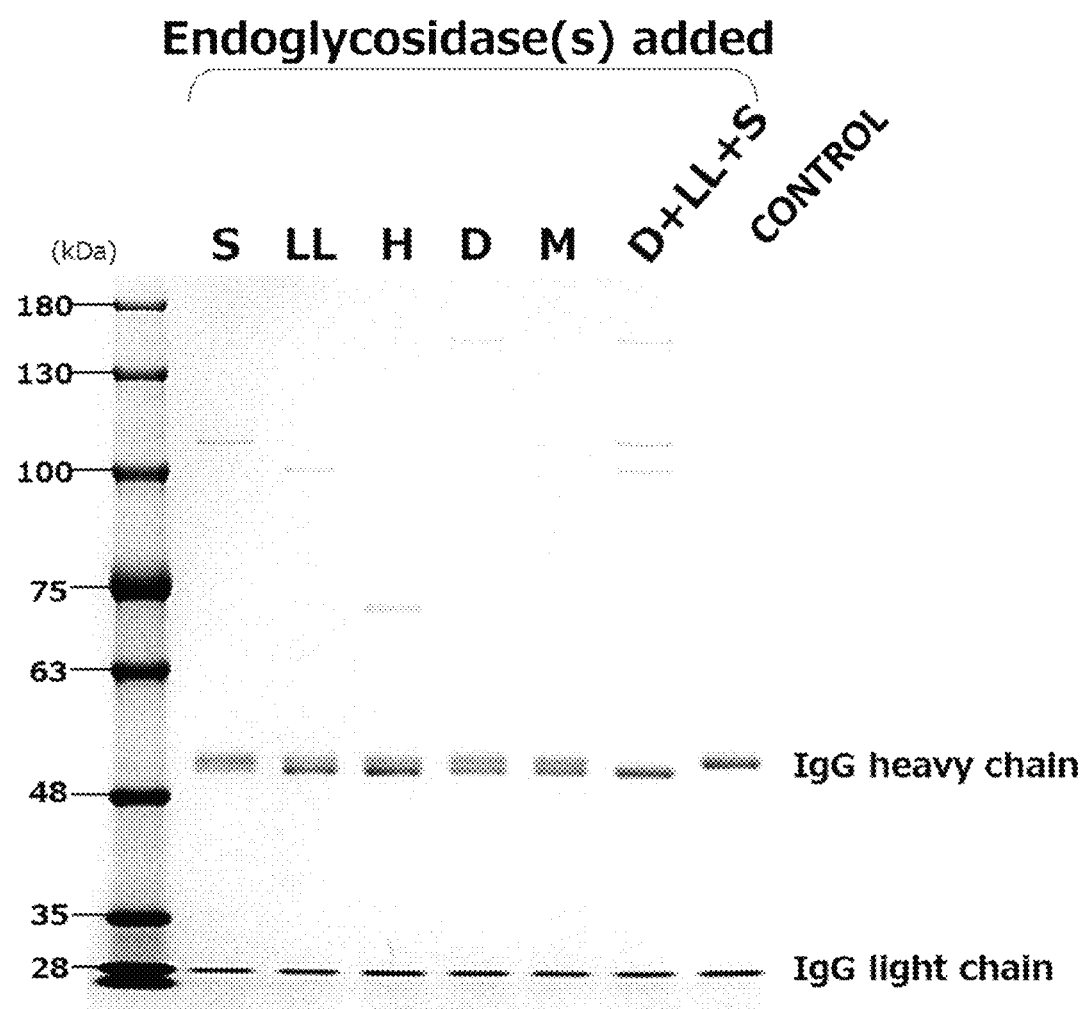
FIG. 4 is a photograph of SDS-PAGE performed on mouse IgG1 produced by the silk gland of silkworm, which was hydrolyzed with various types of endoglycosidases.

It was confirmed that when a single endoglycosidase was used as an enzyme in hydrolysis, unreacted N-glycans remained in all cases of the enzymes (FIG. 4). On the other hand, simultaneous hydrolytic products by EndoS, EndoLL and EndoD, which were aligned as controls, did not comprise such unreacted N-glycans, and all of them were shifted to a low molecular weight side.

Example 5

Analysis of Mouse IgG1 Glycopeptide Glu-Glu-Gln-Phe-Asn (Glycan)-Ser-Thr-Phe-Arg (SEQ ID NO: 7)

Mouse IgG1 (15 μg) produced by the silk gland of silkworms was dissolved in a 100 mM ammonium hydrogen carbonate aqueous solution (30 μL), and a 1.0% (w/v) RapiGest aqueous solution (3 μL) was then added to the above obtained solution. The obtained mixture was heated at 90° C. for 15 minutes, and it was then cooled at room temperature for 30 minutes. To this reaction solution, trypsin (Sequence Grade) (0.25 mg/ml, 5 μL) was added, and the obtained mixture was reacted at 37° C. for 12 hours. Thereafter, the reaction solution was heated at 90° C. for 30 minutes to inactivate the enzyme, and it was then desalted by a G-25 column (0.8×6 cm, 3 mL) and was concentrated. To the resulting solution, DMF (5 μL) was added, and the obtained mixture was then heated at 60° C. for 5 minutes. Thereafter, a 200 mM benzoic anhydride-methanol solution (100 μL) was added to the reaction solution, and the obtained mixture was then reacted while applying ultrasonic wave for 30 minutes using an ultrasonic washing machine. After that, a 0.5 M sodium hydroxide aqueous solution (60 μL) was added to the reaction solution, and the thus obtained mixture was then stirred at room temperature for 30 minutes. Thereafter, water (200 μL) was added to the reaction solution, and the mixture was then washed with EtOAc (400 μL) three times, followed by vacuum concentration. This reaction product was desalted by a G-25 column (0.8×6 cm, 3 mL), was then loaded on a C18 Spin column (10 mg), and was fully washed with water (2 mL). Thereafter, the reaction product was recovered with a 25% acetonitrile aqueous solution (650 μL) and a 50% acetonitrile aqueous solution (650 μL), and was then concentrated under reduced pressure. To this sample, water (20 μL), Sepharose 4B (wet 50 μL), ethanol (100 μL), and n-butanol (400 μL) were added in this order, and the obtained mixture was then stirred at room temperature for 1 hour. Thereafter, the solution was transferred into an empty column, was then washed with n-butanol:ethanol:water=8:2:1 (v/v/v) (2 mL). A mouse IgG1 glycopeptide was recovered with ethanol:water=1:2 (v/v) (2 mL), and was then concentrated under reduced pressure.

This sample was dissolved in water (10 μL), and 0.5 μL of the solution was then added onto a MALDI target plate. The solution was mixed with a DHBA solution (10 mg/ml of 50% acetonitrile aqueous solution) (1 μL), and was then dried and hardened. Employing MALDI-QIT-TOF MS apparatus (AXIMA-Resonance) manufactured by Shimadzu Corporation, MS measurement was carried out in a positive mode.

Figure 5:
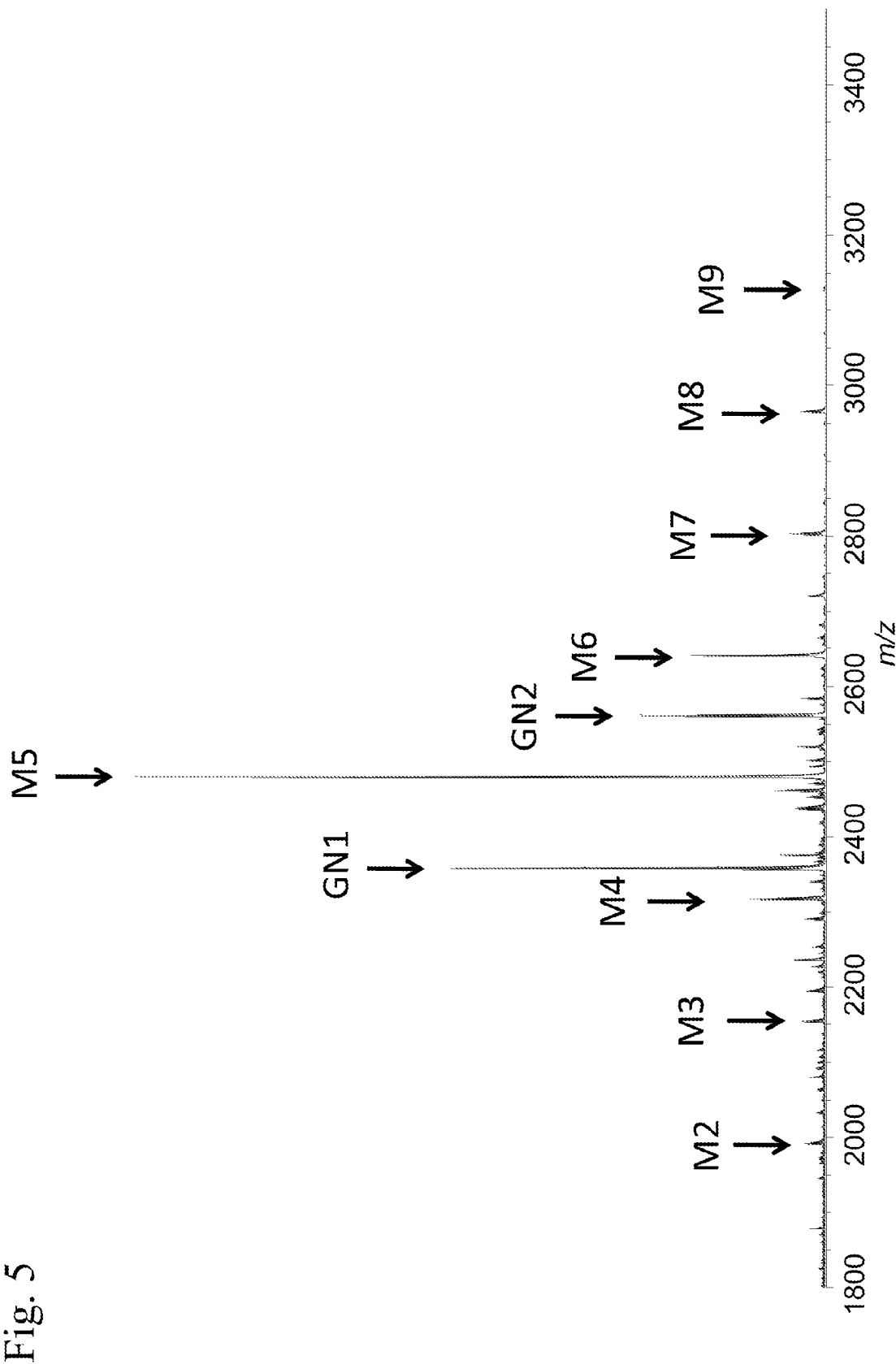
FIG. 5 shows a MS spectrum of a glycopeptide fragment (Bz-Glu-Glu-Gln-Phe-Asn (Glycan)-Ser-Thr-Phe-Arg (SEQ ID NO: 7)) of mouse IgG1 produced by the silk gland of silkworm. The longitudinal axis indicates an intensity ratio, and the horizontal axis indicates m/z values. "M2," "M3" and "M4" represent m/z=1992.19, 2154.28, and 2316.36, to which paucimannose type N-glycans M2, M3 and M4 conjugate, respectively. "GN1" and "GN2" represent m/z=2357.39 and 2560.51, to which complex type N-glycans GN1 and GN2 conjugate, respectively. "M5," "M6," "M7," "M8" and "M9" represent m/z=2478.44, 2640.53, 2802.63, 2964.72 and 3126.84, to which high mannose type N-glycans M5, M6, M7, M8 and M9 conjugate, respectively.
Figure 6A:
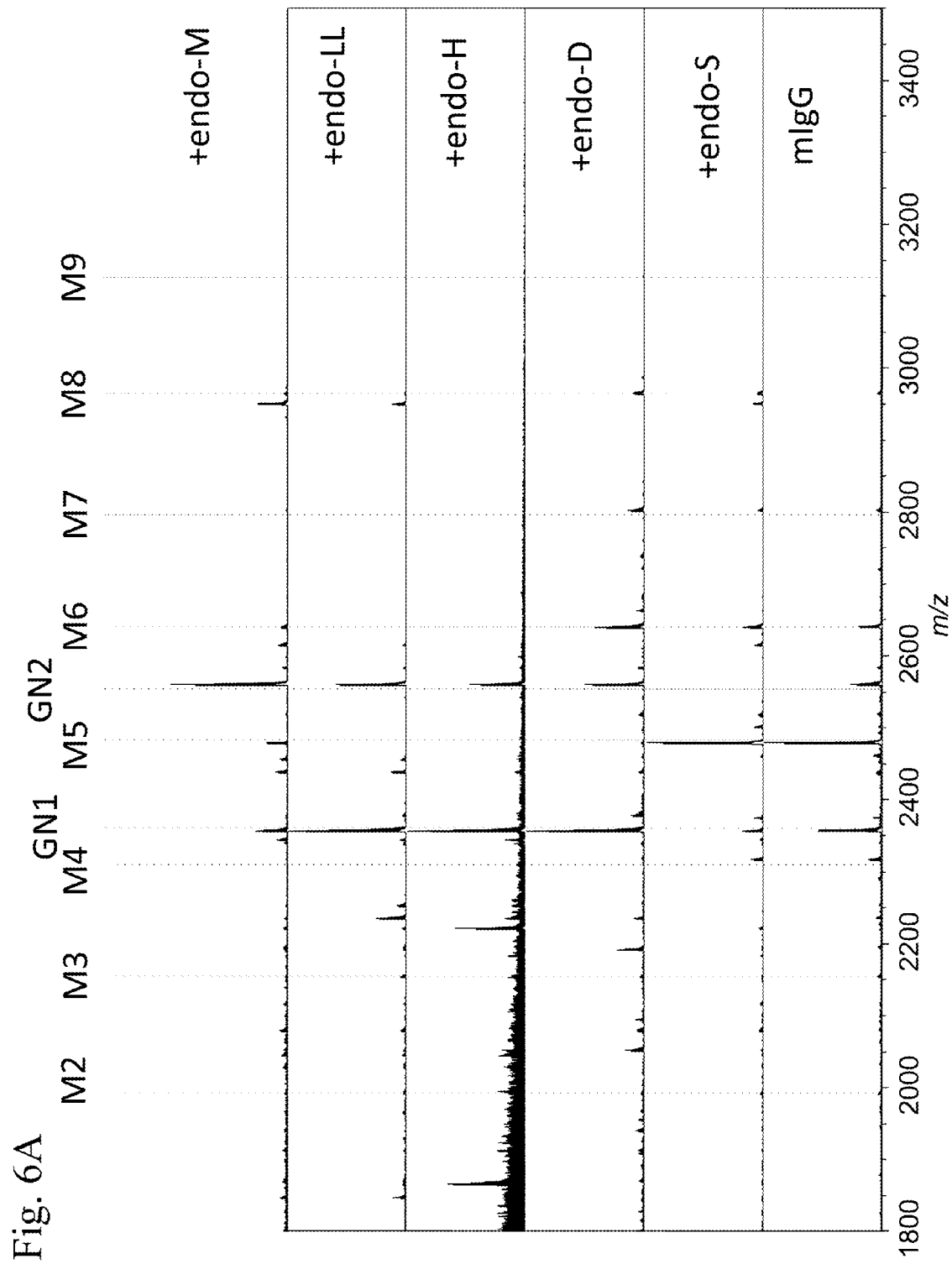
FIG. 6A shows MS spectra of a glycopeptide fragment (Bz-Glu-Glu-Gln-Phe-Asn (Glycan)-Ser-Thr-Phe-Arg (SEQ ID NO: 7)) of mouse IgG1 produced by the silk gland of silkworm treated or untreated with various endo-enzymes (Endo-M, EndoLL, Endo-H, Endo-D, and EndoS).
Figure 6B:
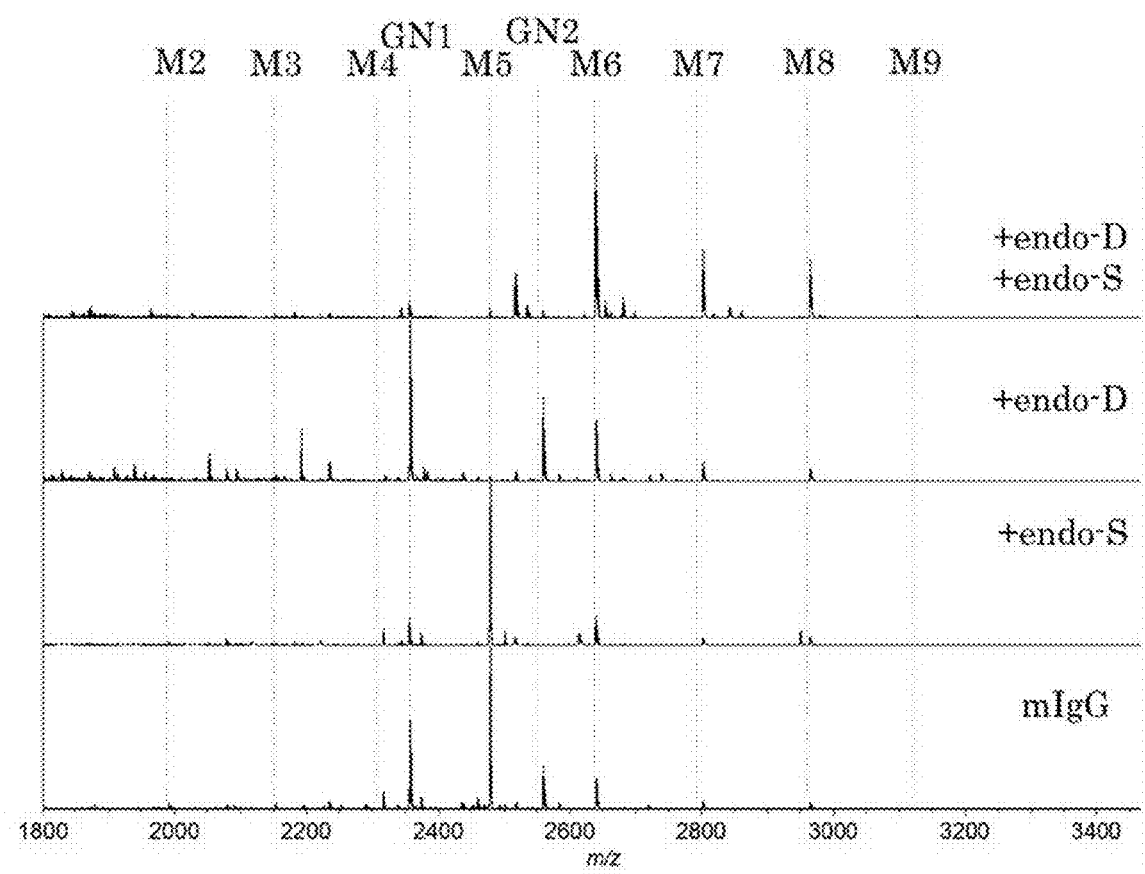
FIG. 6B shows MS spectra of a glycopeptide fragment (Bz-Glu-Glu-Gln-Phe-Asn (Glycan)-Ser-Thr-Phe-Arg (SEQ ID NO: 7)) of mouse IgG1 produced by the silk gland of silkworm treated or untreated with various endo-glycosidases or a combination thereof (Endo-D+EndoS, Endo-D, and EndoS).
Figure 6C:
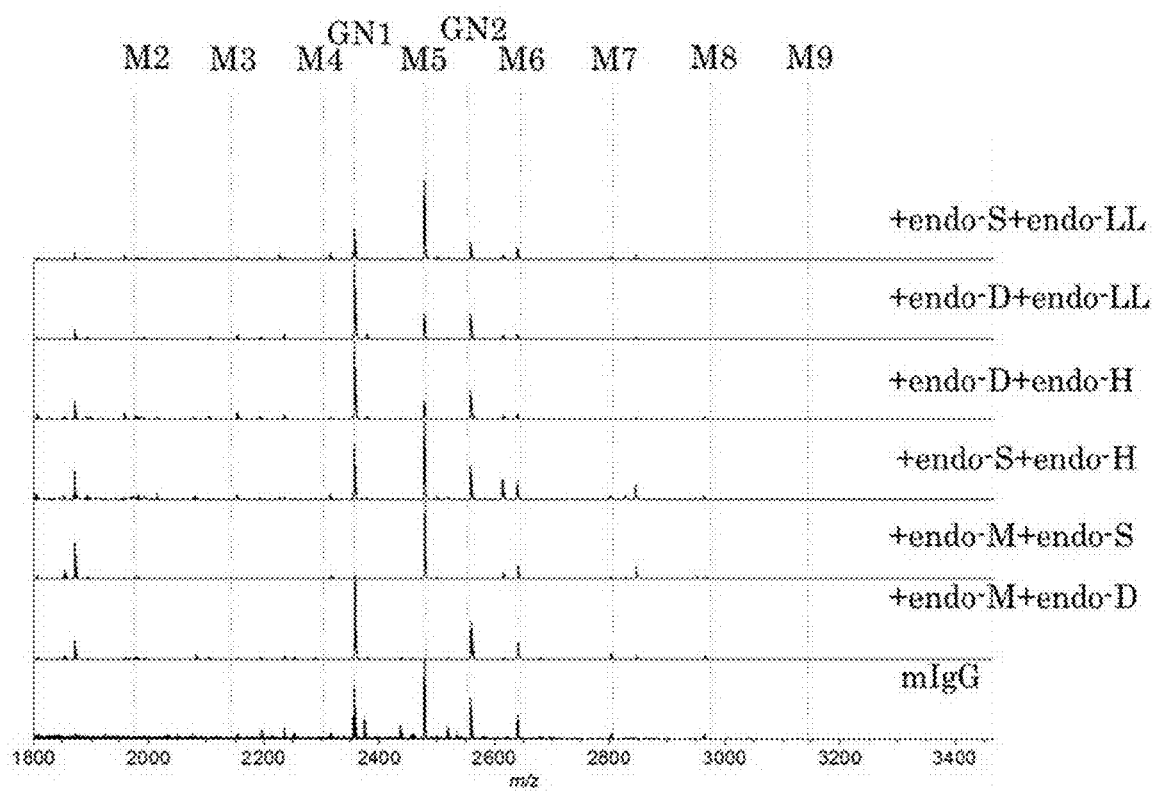
FIG. 6C shows MS spectra of a glycopeptide fragment (Bz-Glu-Glu-Gln-Phe-Asn (Glycan)-Ser-Thr-Phe-Arg (SEQ ID NO: 7)) of mouse IgG1 produced by the silk gland of silkworm treated or untreated with various endo-glycosidases or a combination thereof (Endo-M+Endo-D, Endo-M+EndoS, Endo-D+Endo-H, EndoS+Endo-H, Endo-D+EndoLL, and EndoS+EndoLL).
Figure 6D:
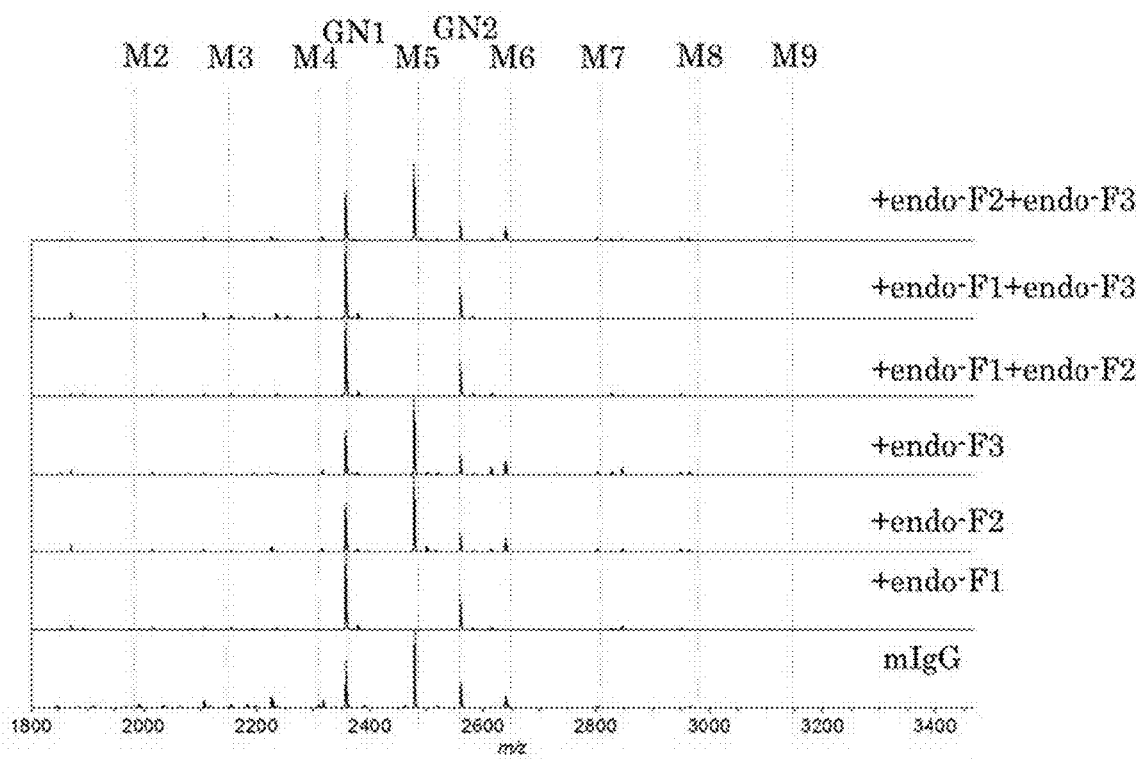
FIG. 6D shows MS spectra of a glycopeptide fragment (Bz-Glu-Glu-Gln-Phe-Asn (Glycan)-Ser-Thr-Phe-Arg (SEQ ID NO: 7)) of mouse IgG1 produced by the silk gland of silkworm treated or untreated with various endo-glycosidases or a combination thereof (Endo-F1, Endo-F2, Endo-F3, Endo-F1+Endo-F2, Endo-F1+Endo-F3, and Endo-F2+Endo-F3).

The results are shown in FIG. 5. As a result of the MS measurement, there were detected: m/z=1992.19, 2154.28, and 2316.36, in which paucimannose type N-glycans M2, M3 and M4 linked to Bz-Glu-Glu-Gln-Phe-Asn-Ser-Thr-Phe-Arg (SEQ ID NO: 7); m/z=2357.39 and 2560.51, in which complex type N-glycans GN1 and GN2 linked thereto; and m/z=2478.44, 2640.53, 2802.63, 2964.72, and 3126.84, in which high mannose type N-glycans M5, M6, M7, M8, and M9 linked thereto.

Example 6

Analysis of Digestion by Endo-Glycosidases of Mouse IgG1 Produced by Silk Gland of Silkworms Mouse IgG1 (15 μg) produced by the silk gland of silkworms, which had been treated with various endoglycosidases (Endo-M, EndoLL, Endo-H, Endo-D, EndoS, Endo-D+EndoS, Endo-M+Endo-D, Endo-M+EndoS, Endo-D+Endo-H, EndoS+Endo-H, Endo-D+EndoLL, EndoS+EndoLL, Endo-F1, Endo-F2, Endo-F3, Endo-F1+Endo-F2, Endo-F1+Endo-F3, or Endo-F2+Endo-F3), was dissolved in a 100 mM ammonium hydrogen carbonate aqueous solution (30 μL). Thereafter, a 1.0% (w/v) RapiGest aqueous solution (3 μL) was added to each solution, and the obtained mixture was heated at 90° C. for 15 minutes and was then cooled at room temperature for 30 minutes. To this reaction solution, trypsin (Sequence Grade) (0.25 mg/ml, 5 μL) was added, and the obtained mixture was reacted at 37° C. for 12 hours. Thereafter, the reaction solution was heated at 90° C. for 30 minutes to inactivate the enzyme, and it was then desalted by a G-25 column (0.8×6 cm, 3 mL) and was concentrated. To the resulting solution, DMF (5 μL) was added, and the obtained mixture was then heated at 60° C. for 5 minutes. Thereafter, a 200 mM benzoic anhydride-methanol solution (100 μL) was added to the reaction solution, and the obtained mixture was then reacted while applying ultrasonic wave for 30 minutes at room temperature using an ultrasonic washing machine. After that, a 0.5 M sodium hydroxide aqueous solution (60 μL) was added to the reaction solution, and the thus obtained mixture was then stirred at room temperature for 30 minutes. Thereafter, water (200 μL) was added to the reaction solution, and the mixture was then washed with EtOAc (400 μL) three times, followed by vacuum concentration. This reaction product was desalted by a G-25 column (0.8×6 cm, 3 mL), was then loaded on a C18 Spin column (10 mg), and was then fully washed with water (2 mL). Thereafter, the reaction product was recovered with a 25% acetonitrile aqueous solution (650 μL) and a 50% acetonitrile aqueous solution (650 μL), and was then concentrated under reduced pressure. To this sample, water (20 μL), Sepharose 4B (wet 50 μL), ethanol (100 μL), and n-butanol (400 μL) were added in this order, and the obtained mixture was then stirred at room temperature for 1 hour. Thereafter, the solution was transferred into an empty column, and was then washed with n-butanol:ethanol:water=8:2:1 (v/v/v) (2 mL). A mouse IgG1 glycopeptide was recovered with ethanol:water=1:2 (v/v) (2 mL), and was then concentrated under reduced pressure.

This sample was dissolved in water (10 μL), and 0.5 μL of the solution was then added onto a MALDI target plate. The solution was mixed with a DHBA solution (10 mg/ml of 50% acetonitrile aqueous solution) (1 μL), and was then dried and hardened. Employing MALDI-QIT-TOF MS apparatus (AXIMA-Resonance) manufactured by Shimadzu Corporation, MS measurement was carried out in a positive mode.

In the MS measurement, there were detected: m/z=1992.19, 2154.28, and 2316.36, in which paucimannose type N-glycans M2, M3 and M4 linked to Bz-Glu-Glu-Gln-Phe-Asn-Ser-Thr-Phe-Arg (SEQ ID NO: 7); m/z=2357.39 and 2560.51, in which complex type N-glycans GN1 and GN2 linked thereto; and m/z=2478.44, 2640.53, 2802.63, 2964.72, and 3126.8, in which high mannose type N-glycans M5, M6, M7, M8, and M9 linked thereto.

Figure 7A:
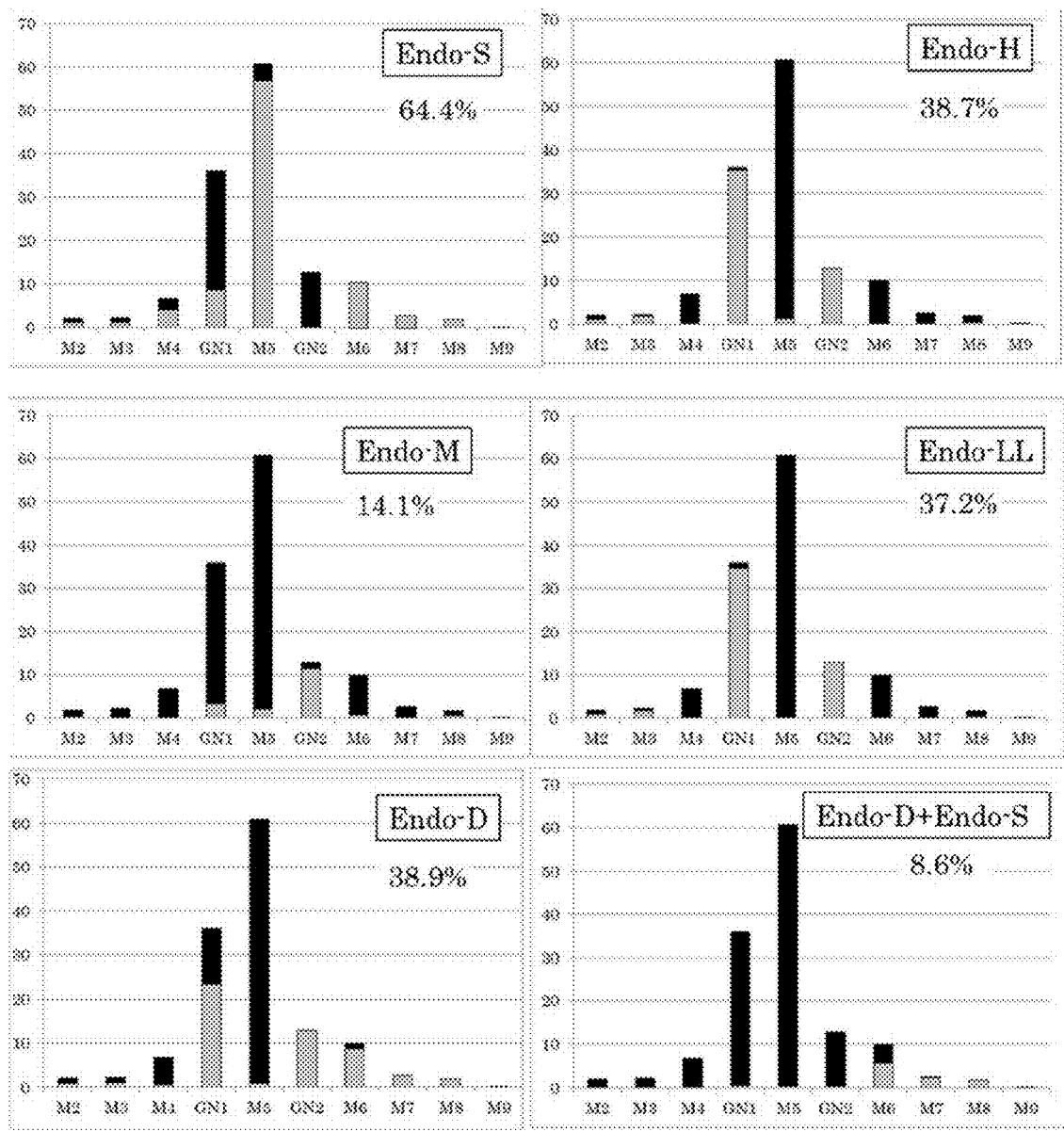
FIG. 7A is graphs showing the amount (pmol) of an antibody-linked N-glycan with each structure per 10 μg of mouse IgG1 produced by the silk gland of silkworm treated or untreated with various endo-glycosidases or a combination thereof (EndoS, Endo-H, Endo-M, EndoLL, Endo-D, and Endo-D+EndoS). The black bar shows the amount of a N-glycan with indicated structure before treatment with endoglycosidase, and the grey bar shows that after treatment with endoglycosidase. The longitudinal axis indicates pmol/10 μg IgG1, and the horizontal axis indicates N-glycan structure. The percentage in the table indicates the amount of the remaining N-glycan.
Figure 7B:
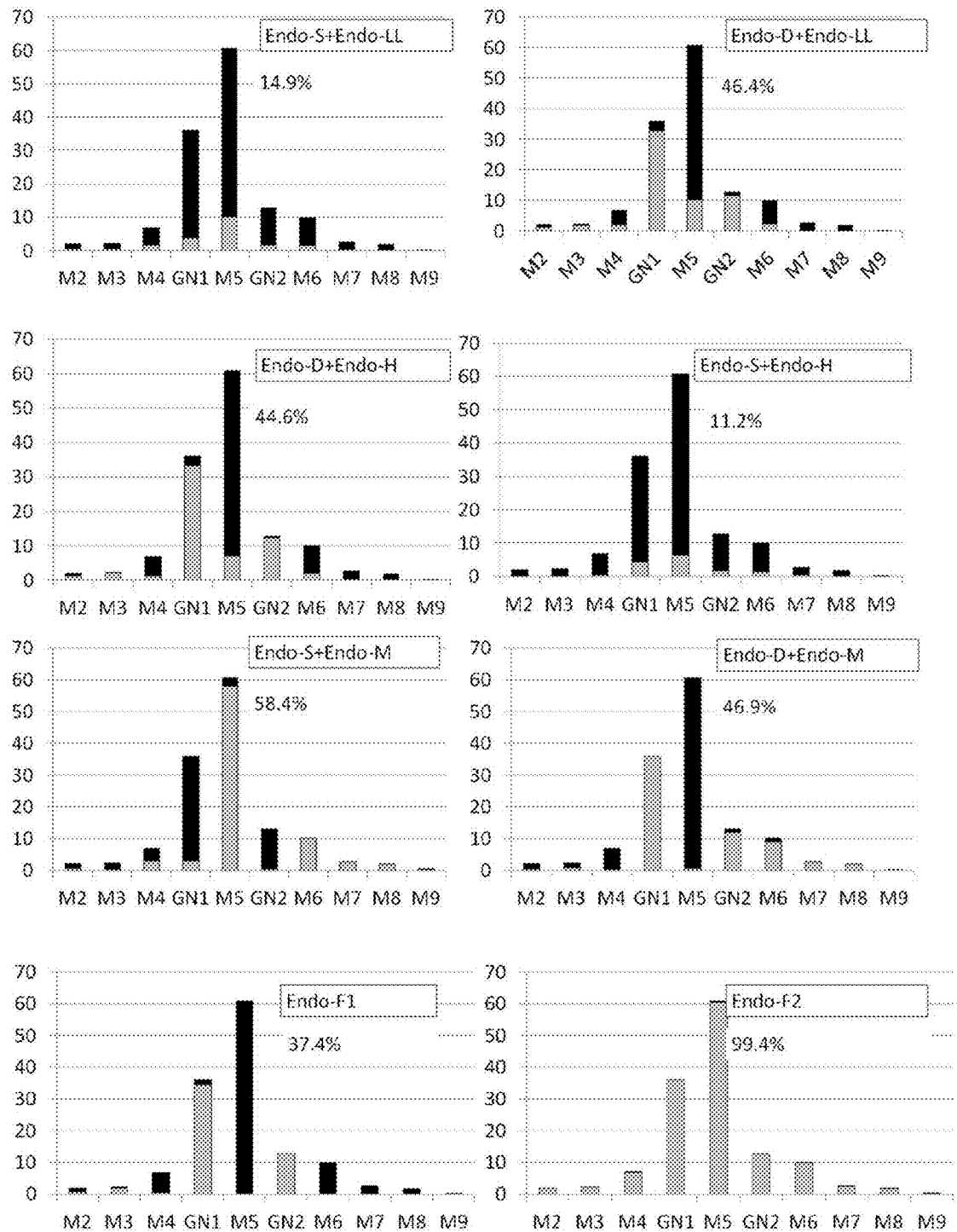
FIG. 7B is graphs showing the amount (pmol) of an antibody-linked N-glycan with each structure per 10 μg of mouse IgG1 produced by the silk gland of silkworm treated or untreated with various endo-glycosidases or a combination thereof (EndoS+EndoLL, Endo-D+EndoLL, Endo-D+Endo-H, EndoS+Endo-H, EndoS+Endo-M, Endo-D+Endo-M, Endo-F1, and Endo-F2). The black bar shows the amount of a N-glycan with indicated structure before treatment with endoglycosidase, and the grey bar shows that after treatment with endoglycosidase. The longitudinal axis indicates pmol/10 μg IgG1, and the horizontal axis indicates N-glycan structure. The percentage in the table indicates the amount of the remaining N-glycan.

The results are shown in FIG. 6A to FIG. 6D. In addition, the intensity ratio of individual N-glycans obtained by the treatment with individual endoglycosidases was overlapped with the intensity ratio of the N-glycans of antibodies that had not been treated with endoglycosidases, so as to prepare a bar graph, and the types of N-glycans hydrolyzed by the endoglycosidases were analyzed. The analytical results are shown in FIG. 7A to FIG. 7C.

Example 7

Production of Trastuzumab by Silk Gland of Silkworms

The trastuzumab heavy chain and light chain genes, to the 5'-terminus of each of which the 5'-untranslated region sequence of BmNPV polyhedrin had been added, were artificially synthesized. These synthesized genes were each inserted into a silkworm transformation vector pMSG3.1 MG according to the method described in Example 2, and a trace amount of the vector DNA was then injected into silkworm eggs, so as to produce transgenic silkworms, into which a trastuzumab gene had been incorporated. Thereafter, the transgenic silkworms were mated with silkworms expressing an IE1 gene to produce silkworms having both the trastuzumab gene and the IE1 gene. These silkworms were raised and allowed to produce cocoons. From the obtained cocoons, trastuzumab produced by the silk gland of silkworms was purified by the method described in Example 2.

Example 8

Preparation of Acceptor of Trastuzumab Produced from Silkworm Silk Gland by Simultaneous Hydrolysis with EndoS, EndoLL and EndoD Trastuzumab (500 μg) produced by the silk gland of silkworms, and EndoS (1 μg), EndoLL (1 μg) and RemoveiT Endo-D ((NEB) 100 units) were added to a 50 mM sodium phosphate buffer solution (pH 7.5) to a total amount of 200 μl, and the obtained mixture was then reacted at 37° C. for 22 hours. To this reaction solution, 10 μl of Ab-Capcher ExTra (ProteNova Co., Ltd.) that had been equilibrated with a 50 mM sodium phosphate buffer solution (pH 7.5) was added, and the thus obtained mixture was then subjected to rotary shaking at room temperature for 30 minutes, so that the antibody was captured on the gel carrier. To the carrier that had been washed with 500 μl of PBS at room temperature for 5 minutes, 100 μl of a 0.1 M glycine-HCl buffer solution (pH 2.7) was added for elution, and 0.3 μl of a 1 M Tris-HCl buffer solution (pH 9.0) was then added to the eluted solution so as to neutralize it. This elution operation was carried out twice in total, and the eluted solutions were gathered. While the eluted solution was concentrated with Amicon Ultra-0.5 (NMWL 30 kDa), the buffer was substituted with PBS. 0.5 μg out of the obtained 438 μg of trastuzumab acceptor was aligned with the same amount of mouse IgG1 before being subjected to simultaneous hydrolysis, and was then electrophoresed by 10% SDS-PAGE.

Figure 8:
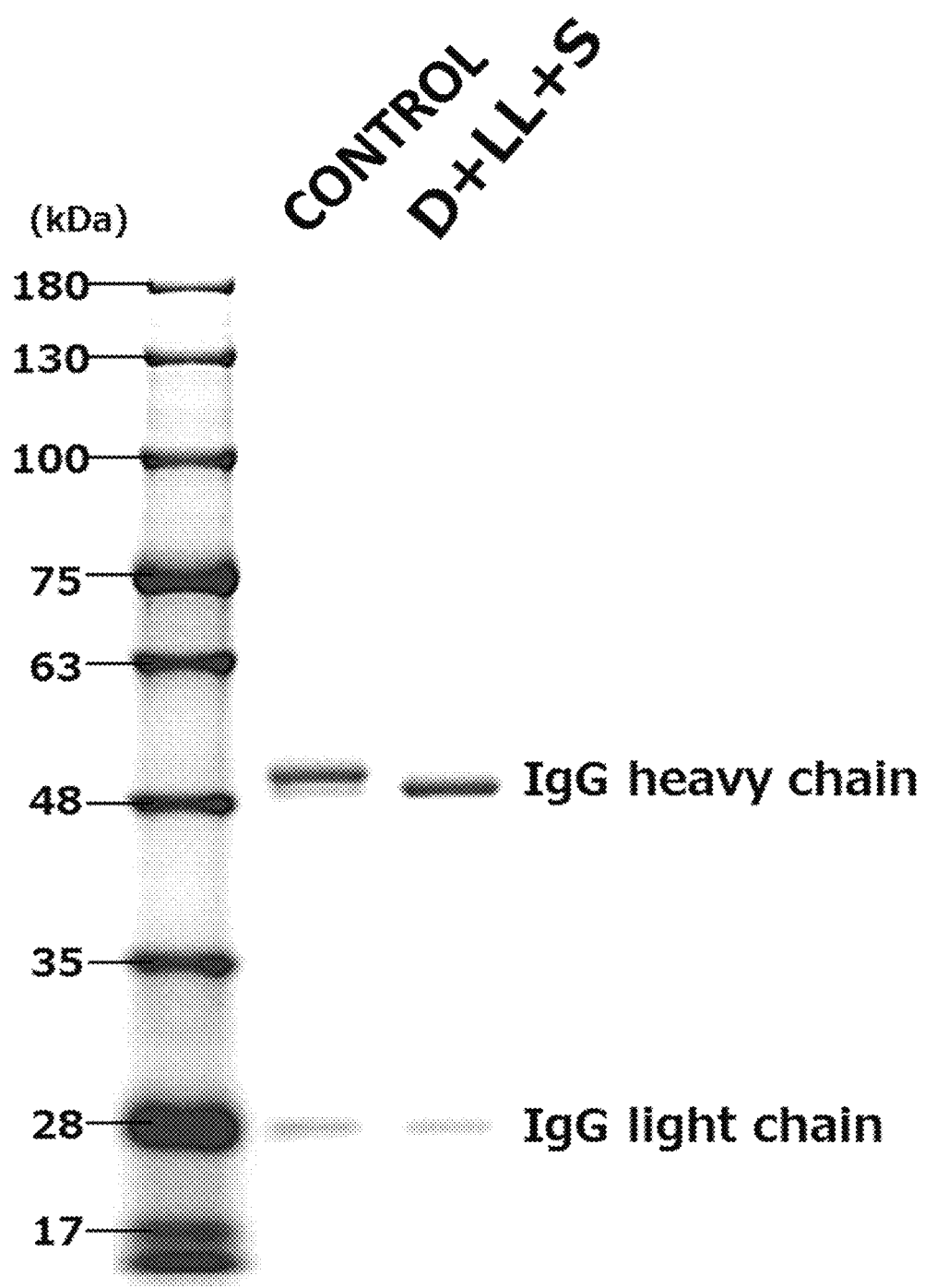
FIG. 8 is a photograph of SDS-PAGE performed on trastuzumab produced by the silk gland of silkworm which was not digested or digested by digestion with EndoS, EndoLL and Endo-D.

It could be confirmed that the acceptor was shifted to a low molecular weight side because N-glycans were hydrolyzed, and that there were no unreacted N-glycans (FIG. 8).

Example 9

Hydrolysis of Trastuzumab Produced by Silk Gland of Silkworms Using Various Types of Endoglycosidases as Single Form Trastuzumab (4 μg) produced by the silk gland of silkworms, and a single form (1 μg) of EndoS, EndoLL, Remove-iT Endo-D (NEB), Endo-H (NEB) or Endo-M (Tokyo Chemical Industry Co., Ltd.), or trastuzumab (4 μg) produced by the silk gland of silkworms, and Remove-iT Endo-D (1 μg) and EndoS (1 μg), were added into a buffer solution to a total amount of 20 μl. The obtained mixture was reacted at 37° C. for 6 hours. In the case of using EndoS, EndoLL, Remove-iT Endo-D or EndoS, and Remove-iT Endo-D for simultaneous hydrolysis, a 50 mM sodium phosphate buffer solution (pH 7.5) was used as a buffer solution. In the case of using Endo-H, a 50 mM sodium citrate buffer solution (pH 5.5) was used as a buffer solution, and in the case of using Endo-M, a 50 mM sodium phosphate buffer solution (pH 6.0) was used as a buffer solution. After completion of the reaction, trastuzumab (0.5 μg) was electrophoresed by 10% SDS-PAGE.

Figure 9:
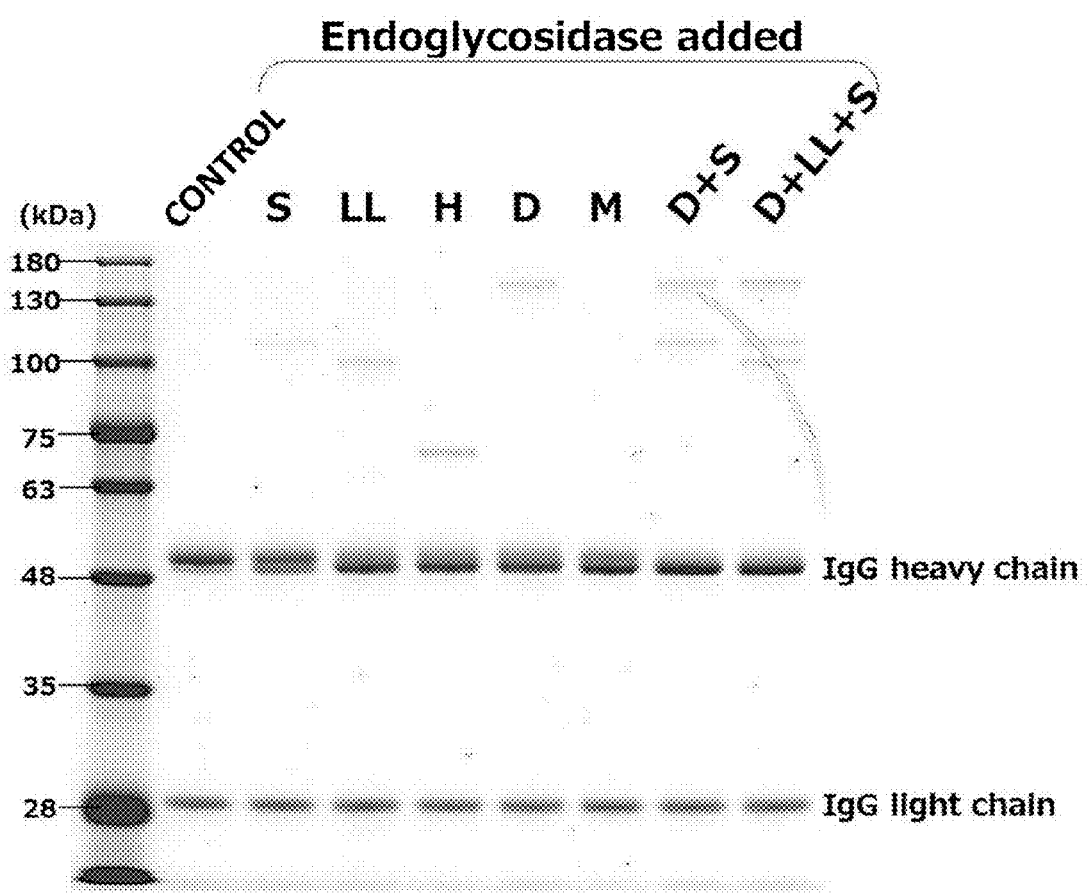
FIG. 9 is a photograph of SDS-PAGE performed on trastuzumab produced by the silk gland of silkworm that was hydrolyzed by various types of endoglycosidases.

The results are shown in FIG. 9. It was confirmed that when a single digestion of glycosidase was used in hydrolysis, unreacted N-glycans remained in all cases. On the other hand, simultaneous hydrolytic products by EndoS, EndoLL and Remove-iT Endo-D, which were aligned as controls, did not comprise such unreacted N-glycans, and all of them were shifted to a low molecular weight side. Even in the case of double digestion with EndoS and Remove-iT Endo-D, unreacted N-glycans were not apparently confirmed.

Example 10

Analysis of Trastuzumab Glycopeptide Glu-Glu-Gln-Tyr-Asn (Glycan)-Ser-Thr-Tyr-Arg (SEQ ID NO: 8) Produced by Silk Gland of Silkworms Trastuzumab (20 μg) produced by the silk gland of silkworms was dissolved in a 100 mM ammonium hydrogen carbonate aqueous solution (50 μL), and a 1.0% (w/v) RapiGest aqueous solution (5 μL) was then added to the above obtained solution. The obtained mixture was heated at 90° C. for 15 minutes, and it was then cooled at room temperature for 30 minutes. To this reaction solution, trypsin (Sequence Grade) (0.25 mg/ml, 5 μL) was added, and the obtained mixture was reacted at 37° C. for 30 hours. Thereafter, the reaction solution was heated at 90° C. for 30 minutes to inactivate the enzyme, and it was then desalted by a G-25 column (0.8×6 cm, 3 mL) and was concentrated. To the resulting solution, water (20 μL) and pyridine (10 μL) were added, and thereafter, a 200 mM benzoic acid-N-hydroxysuccinimide ester dimethylformamide solution (20 μL) was added to the reaction solution, and the obtained mixture was then reacted at 57° C. for 12 hours. Thereafter, a 0.5 M sodium hydroxide aqueous solution (60 μL) was added to the reaction solution, and the thus obtained mixture was then stirred at room temperature for 30 minutes. Thereafter, water (200 μL) was added to the reaction solution, and the mixture was then washed with EtOAc (400 μL) three times, followed by vacuum concentration. This reaction product was desalted by a G-25 column (0.8×6 cm, 3 mL), was then loaded on a C18 Spin column (10 mg), and was then fully washed with water (2 mL). Thereafter, the reaction product was recovered with a 25% acetonitrile aqueous solution (650 μL) and a 50% acetonitrile aqueous solution (650 μL), and was then concentrated under reduced pressure. To this sample, water (20 μL), Sepharose 4B (wet 50 μL), ethanol (100 μL), and n-butanol (400 μL) were added in this order, and the obtained mixture was then stirred at room temperature for 1 hour. Thereafter, the solution was transferred into an empty column, was then washed with n-butanol:ethanol:water=8:2:1 (v/v/v) (2 mL). A trastuzumab glycopeptide was recovered with ethanol:water=1:2 (v/v) (2 mL), and was then concentrated under reduced pressure.

This sample was dissolved in water (10 μL), and 0.5 μL of the solution was then added onto a MALDI target plate. The solution was mixed with a DHBA solution (10 mg/ml of 50% acetonitrile aqueous solution) (1 μL), and was then dried and hardened. Employing MALDI-QIT-TOF MS apparatus (AXIMA-Resonance) manufactured by Shimadzu Corporation, MS measurement was carried out in a positive mode.

Figure 10:
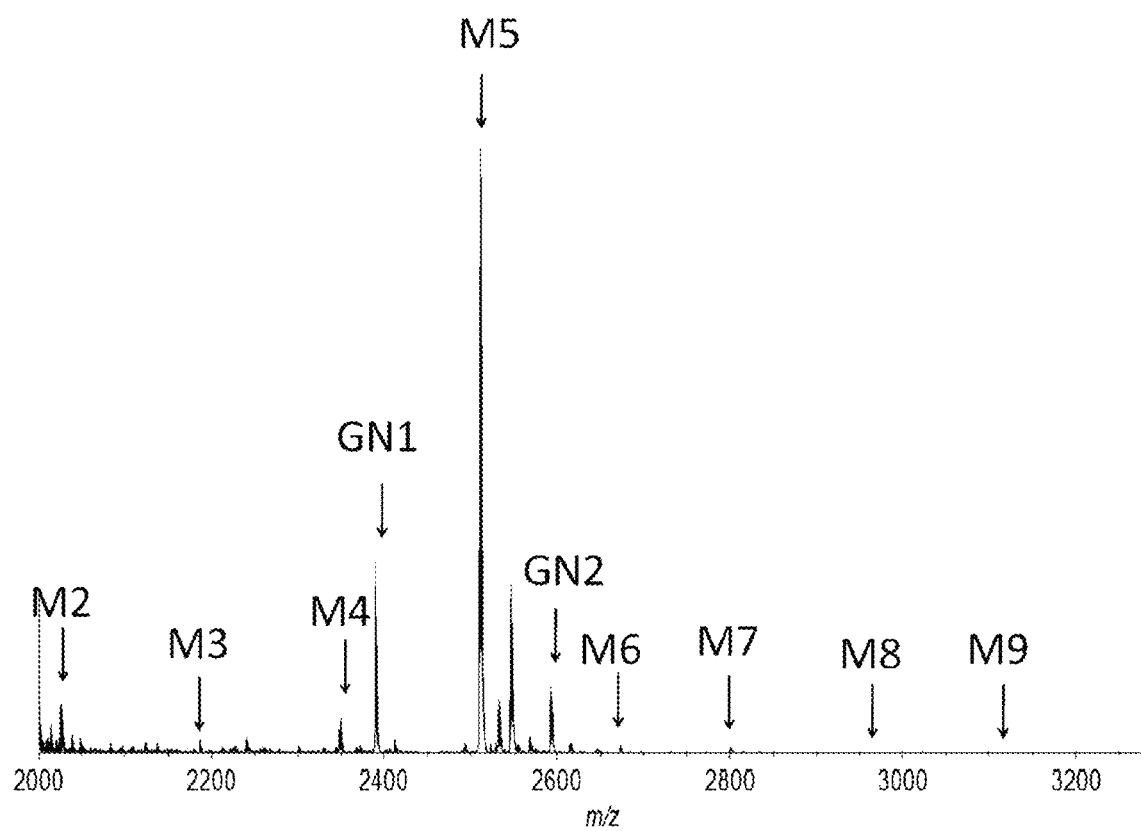
FIG. 10 shows a MS spectrum of a glycopeptide (Bz-Glu-Glu-Gln-Tyr-Asn (Glycan)-Ser-Thr-Tyr-Arg (SEQ ID NO: 8)) of trastuzumab produced by the silk gland of silkworm.

The results are shown in FIG. 10. As a result of the MS measurement, there were detected: m/z=2025.40, 2186.46, and 2348.56, in which paucimannose type N-glycans M2, M3 and M4 linked to Bz-Glu-Glu-Gln-Tyr-Asn-Ser-Thr-Tyr-Arg (SEQ ID NO: 8); m/z=2389.58 and 2592.74, in which complex type N-glycans GN1 and GN2 linked thereto; and m/z=2510.65, 2672.79, 2834.09, 2997.06, and 3158.54, in which high mannose type N-glycans M5, M6, M7, M8, and M9 linked thereto.

Example 11

Analysis of Digestion by Endo-Glycosidases of Trastuzumab Produced by Silk Gland of Silkworms Trastuzumab (20 μg) produced by the silk gland of silkworms, which had been treated with various endoenzymes (Endo-M, Endo-H, Endo-D, EndoS, or Endo-D+EndoS), was dissolved in a 100 mM ammonium hydrogen carbonate aqueous solution (50 μL). Thereafter, a 1.0% (w/v) RapiGest aqueous solution (5 μL) was added to each solution, and the obtained mixture was heated at 90° C. for 15 minutes and was then cooled at room temperature for 30 minutes. To this reaction solution, trypsin (Sequence Grade)

(0.25 mg/ml, 5 μL) was added, and the obtained mixture was reacted at 37° C. for 30 hours. Thereafter, the reaction solution was heated at 90° C. for 30 minutes to inactivate the enzyme, and it was then desalted by a G-25 column (0.8×6 cm, 3 mL) and was concentrated. To the resulting solution, water (20 μL) and pyridine (10 μL) were added, and thereafter, a 200 mM benzoic acid-N-hydroxysuccinimide ester dimethylformamide solution (20 μL) was then added to the reaction solution, and the obtained mixture was then reacted at 57° C. for 12 hours. Thereafter, a 0.5 M sodium hydroxide aqueous solution (60 μL) was added to the reaction solution, and the thus obtained mixture was then stirred at room temperature for 30 minutes. Thereafter, water (200 μL) was added to the reaction solution, and the mixture was then washed with EtOAc (400 μL) three times, followed by vacuum concentration. This reaction product was desalted by a G-25 column (0.8×6 cm, 3 mL), was then loaded on a C18 Spin column (10 mg), and was then fully washed with water (2 mL). Thereafter, the reaction product was recovered with a 25% acetonitrile aqueous solution (650 μL) and a 50% acetonitrile aqueous solution (650 μL), and was then concentrated under reduced pressure. To this sample, water (20 μL), Sepharose 4B (wet 50 μL), ethanol (100 μL), and n-butanol (400 μL) were added in this order, and the obtained mixture was then stirred at room temperature for 1 hour. Thereafter, the solution was transferred into an empty column, and was then washed with n-butanol:ethanol:water=8:2:1 (v/v/v) (2 mL). A trastuzumab glycopeptide was recovered with ethanol:water=1:2 (v/v) (2 mL), and was then concentrated under reduced pressure.

This sample was dissolved in water (10 μL), and 0.5 μL of the solution was then added onto a MALDI target plate. The solution was mixed with a DHBA solution (10 mg/ml of 50% acetonitrile aqueous solution) (1 μL), and was then dried and hardened. Employing MALDI-QIT-TOF MS apparatus (AXIMA-Resonance) manufactured by Shimadzu Corporation, MS measurement was carried out in a positive mode.

Figure 11:
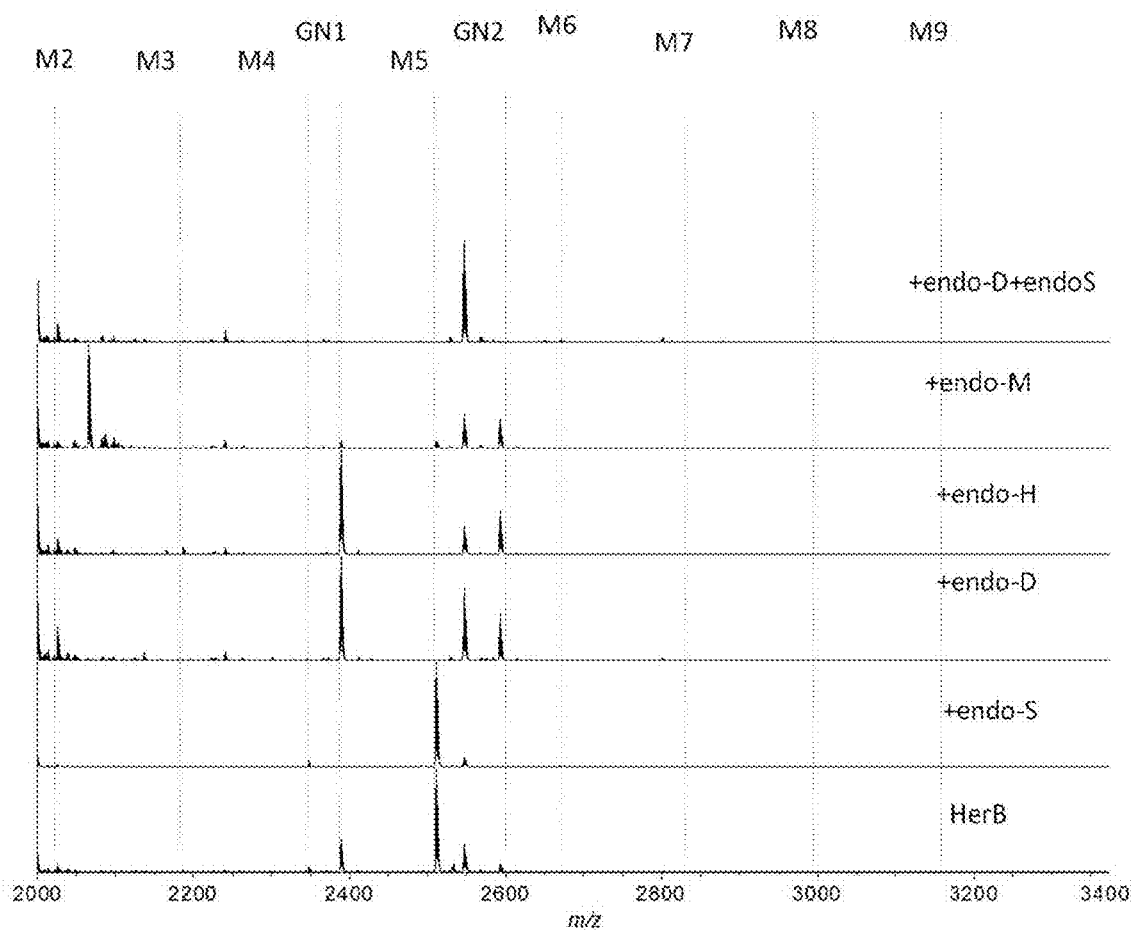
FIG. 11 shows MS spectra of trastuzumab produced by the silk gland of silkworm treated or untreated with various endo-glycosidases or a combination thereof (EndoS, Endo-D, Endo-H, Endo-M, and Endo-D+EndoS).
Figure 12:
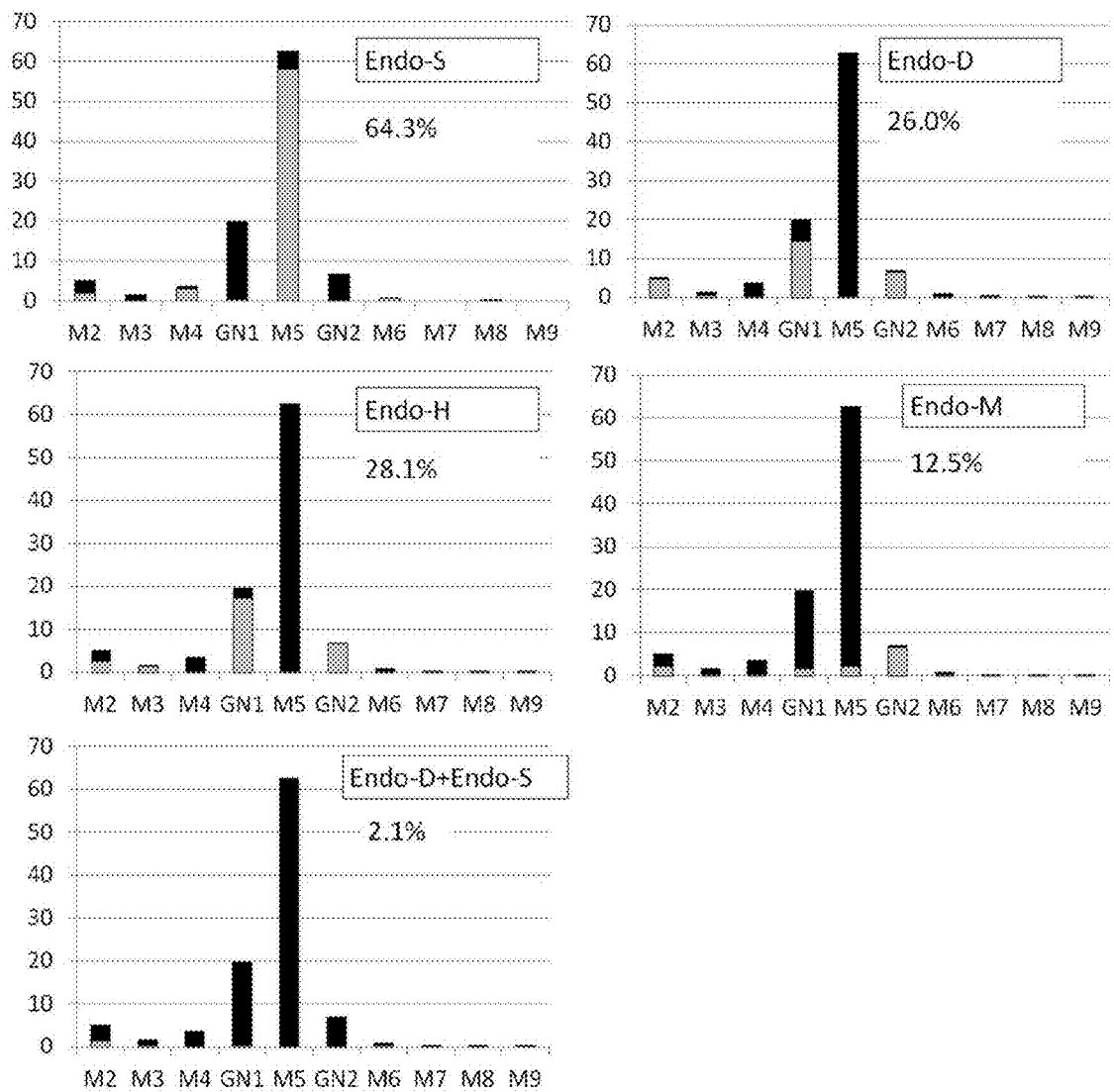
FIG. 12 is graphs showing the amount (pmol) of an antibody-linked N-glycan with each structure per 10 μg of trastuzumab produced by the silk gland of silkworm treated or untreated with various endo-glycosidases or a combination thereof (EndoS, Endo-D, Endo-H, Endo-M, and Endo-D+EndoS). The black bar shows the amount of a N-glycan with each structure before treatment with endoglycosidase, and the grey bar shows that after treatment with the endoglycosidase. The longitudinal axis indicates pmol/10 μg IgG1, and the horizontal axis indicates N-glycan structure. The percentage in the table indicates the amount of the remaining N-glycan.

In the MS measurement, there were detected: m/z=2025.40, 2186.46, and 2348.56, in which paucimannose type N-glycans M2, M3 and M4 linked to Bz-Glu-Glu-Gln-Tyr-Asn-Ser-Thr-Tyr-Arg (SEQ ID NO: 8); m/z=2389.58 and 2592.74, in which complex type N-glycans GN1 and GN2 linked thereto; and m/z=2510.65, 2672.79, 2834.09, 2997.06, and 3158.54, in which high mannose type N-glycans M5, M6, M7, M8, and M9 linked thereto The results are shown in FIG. 11. In addition, the intensity ratio of individual N-glycans obtained by the treatment with individual endoglycosidases was overlapped with the intensity ratio of the N-glycans of antibodies that had not been treated with endoglycosidases, so as to prepare a bar graph, and the types of N-glycans hydrolyzed by the endoglycosidases were analyzed. The analytical results are shown in FIG. 12.

Example 12

Remodeling of N-Glycans of Trastuzumab Produced by the Silk Gland of Silkworms

Figure 13:
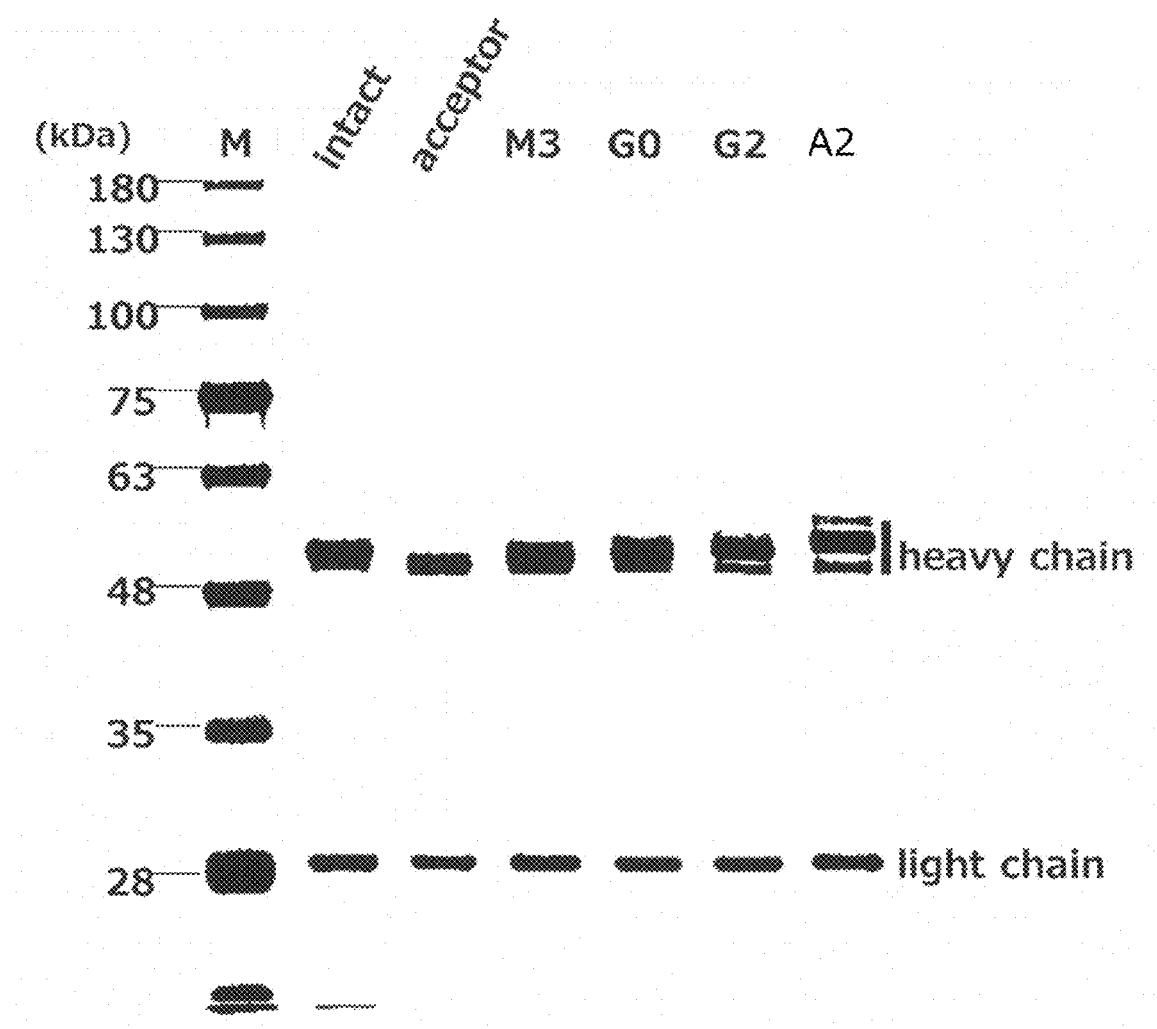
FIG. 13 is a photograph of SDS-PAGE on trastuzumab produced by the silk gland of silkworm, in which a N-glycan has been transglycosylated.
Figure 14:
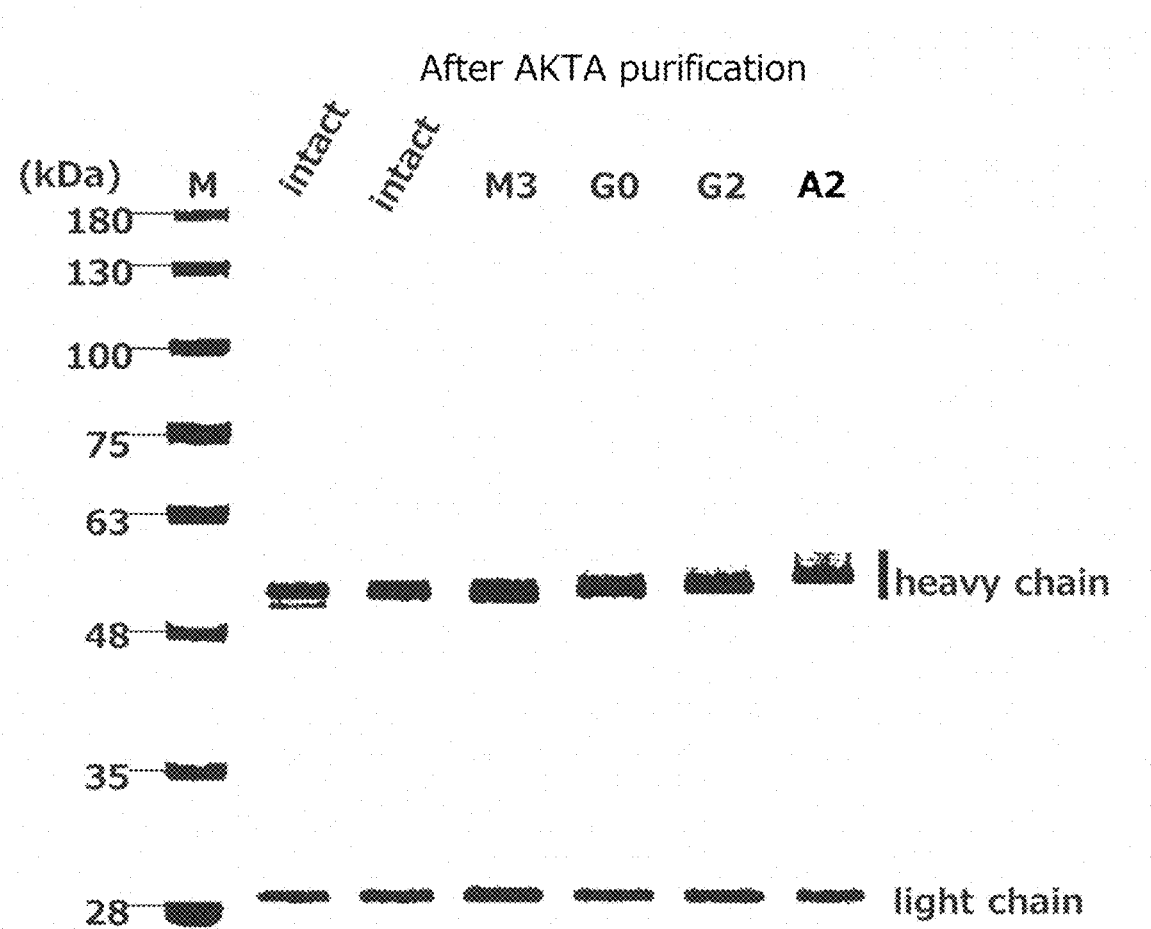
FIG. 14 is a photograph of SDS-PAGE on trastuzumab produced by the silk gland of silkworm, which has been separated and purified by an AKTA-FPLC system.

The trastuzumab acceptor (2 mg) produced by the silk gland of silkworm, which was prepared in Example 8, sugar oxazoline used as a glycosyl donor (1.875 μmol, A2 or G2 or G0 or M3), and GST-EndoS D233Q (200 μg) used as glycosyltransferase were added into a 50 mM Tris-HCl buffer solution (pH 7.5) to a total amount of 500 μl, and the obtained mixture was then reacted at 37° C. for 3 hours. To this reaction solution, 50 μl (bed volume) of COSMOGEL GST-Accept (Nacalai Tesque) that had been equilibrated with the same buffer solution as described above was added, and the obtained mixture was then subjected to rotary shaking at room temperature for 30 minutes, so that GST-EndoS D233Q was captured thereon. To a liquid from which the gel carrier had been removed, 30 μl (bed volume) of Ab-Capcher ExTra (ProteNova Co., Ltd.) that had also been equilibrated with a 50 mM Tris-HCl buffer solution (pH 7.5) was added, and the obtained mixture was then subjected to rotary shaking at room temperature for 1 hour, so that the antibody was captured on the gel carrier. The operation to perform rotary shaking on the gel carrier for 5 minutes to wash it with 500 μl of a NETN buffer (50 mM Tris-HCl buffer solution (pH 8.0), 150 mM sodium chloride, 1 mM EDTA, and 0.1% (w/w) NP-40) was carried out twice, and the carrier was then rinsed with 500 μl of PBS. To the washed carrier, 10 bed volumes of 0.1 M glycine-HCl (pH 2.7) was added. The obtained mixture was subjected to rotary shaking at room temperature for 15 minutes, and 1/30 volumes of a 1 M Tris-HCl buffer solution (pH 9.0) was added to the reaction mixture in a flow-through manner for neutralization. The neutralized elution solution was concentrated with Vivaspin-500 (NMWL 30 kDa) (Sartorius), and the solution was then substituted with PBS. After that, 1 μg out of 1.3 mg of the obtained glycoengineered antibody was subjected to 10% SDS-PAGE. As a result, it was confirmed that all of four types of sugar oxazolines were transferred to a N-acetylglucosamine acceptor, and thus that they were shifted to a high molecular weight side (FIG. 13 and FIG. 14).

Example 13

Purification of Glycoengineered Antibody and HPLC Analysis

Figure 15:
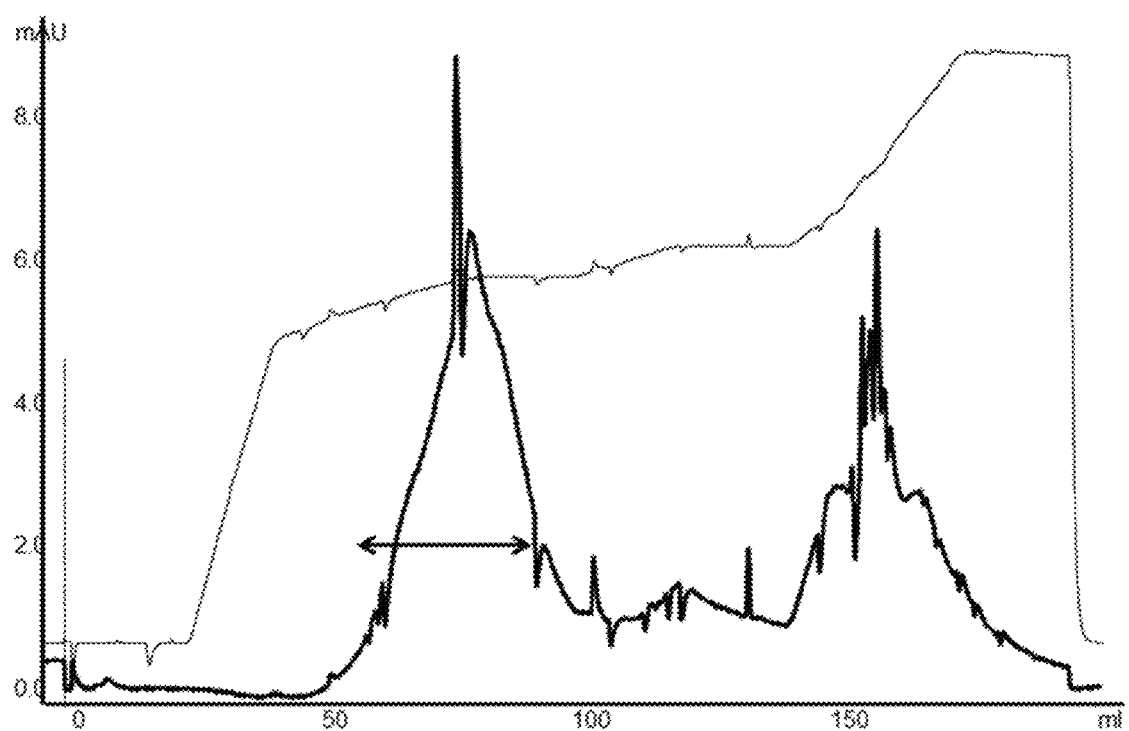
FIG. 15 is a chromatogram of purification of a glycoengineered antibody, in which a N-glycan A2 was attached to trastuzumab which had been produced by the silk gland of silkworm. The longitudinal axis indicates UV absorption intensity. The dotted line indicates the gradient of salt.
Figure 16:
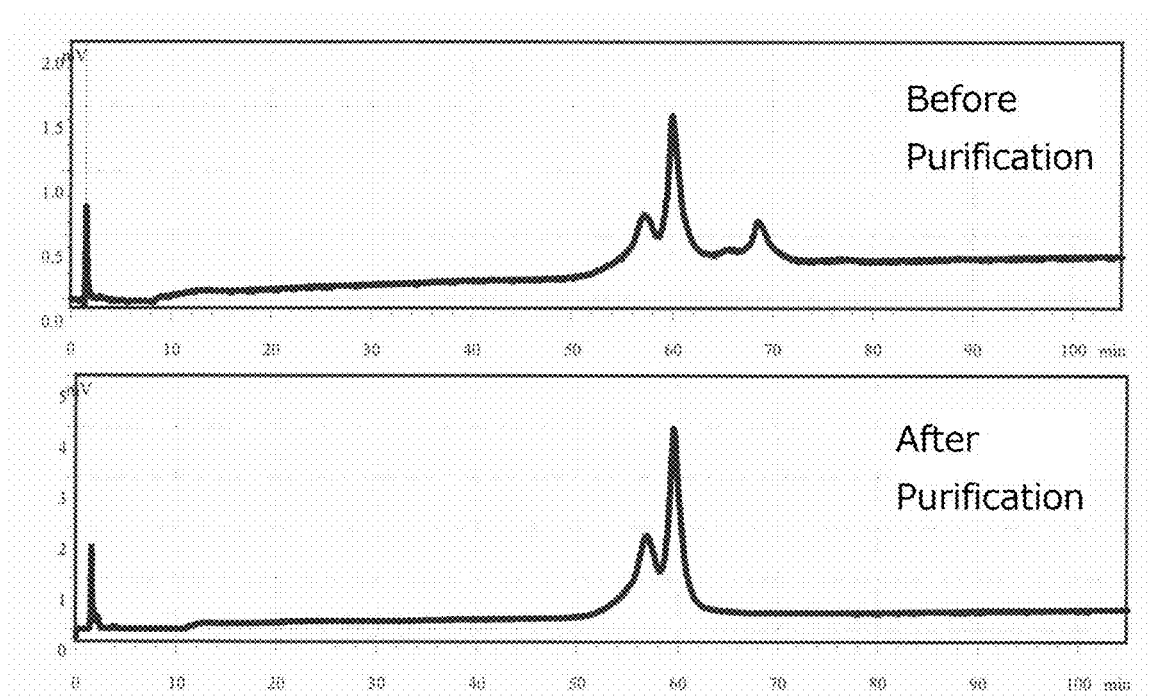
FIG. 16 includes HPLC profiles before and after purification of a glycoengineered antibody which was produced by introducing a N-glycan A2 to trastuzumab which had been produced by the silk gland of silkworm.

Using an AKTA-FPLC system that was set at 4° C., glycoengineered antibodies (A2 form, G2 form, G0 form, and M3 form) (500 μg) that had been each obtained from trastuzumab produced by the silk gland of silkworms were separated by stepwise gradient elution, at a flow rate of 1.35 ml/min, using two liquids, namely, a 20 mM sodium acetate aqueous solution (pH 4.15) and a 20 mM sodium acetate+500 mM sodium chloride aqueous solution, employing a Mono S column (manufactured by GE Healthcare, 4.6×100 mm), and they were then concentrated using an ultrafiltration filter Amicon Ultra-15-10k (manufactured by Millipore). Utilizing Propac WCX-10 (4.0×250 mm) with a HPLC system (manufactured by Shimadzu Corporation) and UV detection at 280 nm, separation and purification were confirmed by gradient elution at a flow rate of 1.0 ml/min, using two liquids, namely, a 10 mM sodium acetate aqueous solution (pH 4.15) and a 10 mM sodium acetate+1000 mM sodium chloride aqueous solution. As a result, it was confirmed that all of the glycoengineered antibodies (A2 form, G2 form, G0 form, and M3 form) could be separated and purified (the data regarding the A2 form are shown as a typical example in FIG. 15 and FIG. 16).

Example 14

MS Analysis of Glycoengineered Antibodies

The purified glycoengineered antibodies (A2 form, G2 form, G0 form, and M3 form) (20 μg) were each dissolved in a 100 mM ammonium hydrogen carbonate aqueous solution (50 μL), and a 1.0% (w/v) RapiGest aqueous solution (5 μL) was added to the solution. The obtained mixture was heated at 90° C. for 15 minutes, and was then cooled at room temperature for 30 minutes. To this reaction solution, trypsin (Sequence Grade) (0.25 mg/ml, 5 μL) was added, and the obtained mixture was reacted at 37° C. for 30 hours. Thereafter, the reaction solution was heated at 90° C. for 30 minutes to inactivate the enzyme, and it was then desalted by a G-25 column (0.8×6 cm, 3 mL) and was concentrated. To the resulting solution, water (20 μL) and pyridine (10 μL) were added, and a 200 mM benzoic acid-N-hydroxysuccinimide ester dimethylformamide solution (20 μL) was added to the reaction solution, and the obtained mixture was then reacted at 57° C. for 12 hours. Thereafter, a 0.5 M sodium hydroxide aqueous solution (60 μL) was added to the reaction solution, and the thus obtained mixture was then stirred at room temperature for 30 minutes. Thereafter, water (200 μL) was added to the reaction solution, and the mixture was then washed with EtOAc (400 μL) three times, followed by vacuum concentration. This reaction product was desalted by a G-25 column (0.8×6 cm, 3 mL), was then loaded on a C18 Spin column (10 mg), and was then fully washed with water (2 mL). Thereafter, the reaction product was recovered with a 25% acetonitrile aqueous solution (650 μL) and a 50% acetonitrile aqueous solution (650 μL), and was then concentrated under reduced pressure. To this sample, water (20 μL), Sepharose 4B (wet 50 μL), ethanol (100 μL), and n-butanol (400 μL) were added in this order, and the obtained mixture was then stirred at room temperature for 1 hour. Thereafter, the solution was transferred into an empty column, was then washed with n-butanol:ethanol:water=8:2:1 (v/v/v) (2 mL). A trastuzumab glycopeptide was recovered with ethanol:water=1:2 (v/v) (2 mL), and was then concentrated under reduced pressure.

This sample was dissolved in water (10 μL), and 0.5 μL of the solution was then added onto a MALDI target plate. The solution was mixed with a DHBA solution (10 mg/ml of 50% acetonitrile aqueous solution) (1 μL), and was then dried and hardened. Employing MALDI-TOF MS apparatus (AXIMA-TOF2) manufactured by Shimadzu Corporation, MS measurement was carried out in a linear positive mode.

Figure 17:
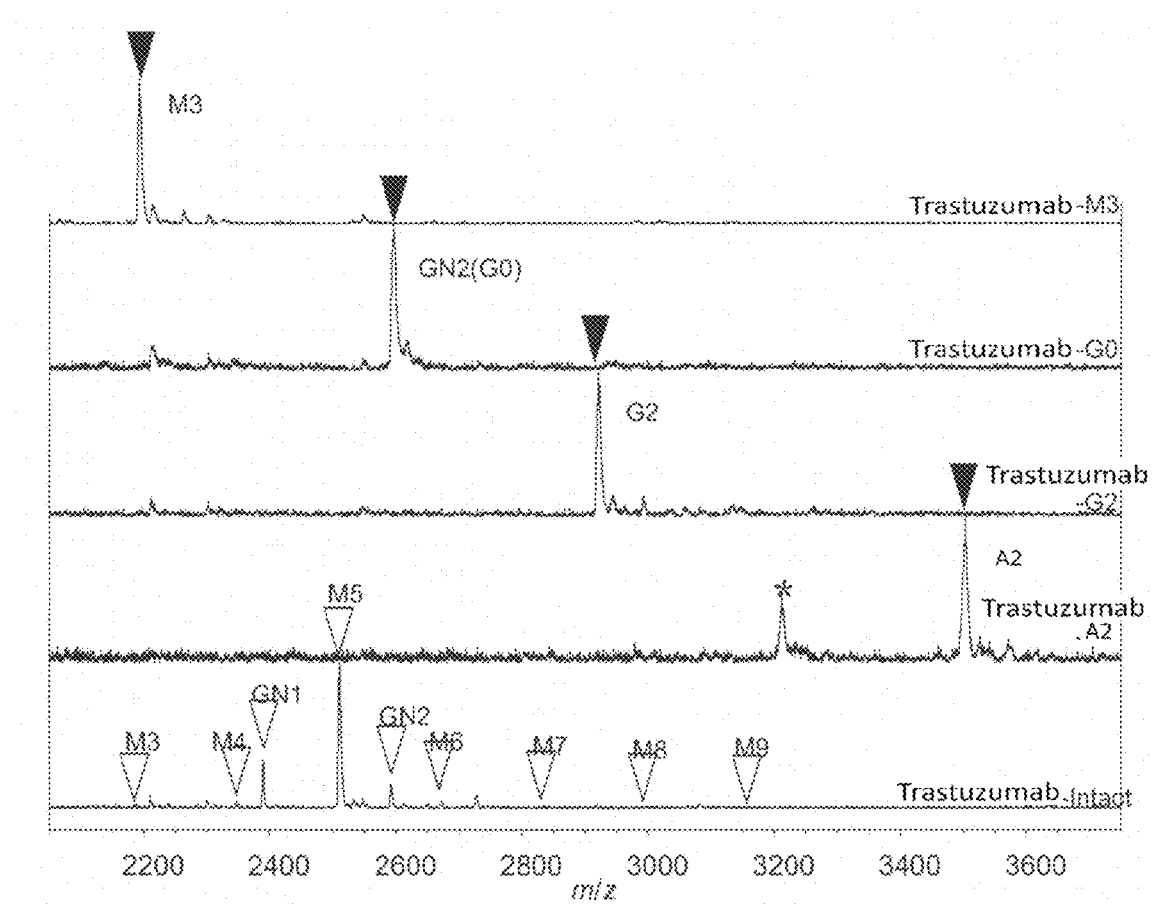
FIG. 17 shows MS spectra of glycopeptides derived from glycoengineered antibodies (A2 form, G2 form, G0 form, and M3 form) after purification and that from trastuzumab produced by the silk gland of silkworm.

In the MS measurement of the purified trastuzumab-A2, m/z=3498.7, in which a sialic acid-containing complex type N-glycan that was an A2 N-glycan linked to Bz-Glu-Glu-Gln-Tyr-Asn-Ser-Thr-Tyr-Arg (SEQ ID NO: 8), and a fragment ion m/z=3207.7, in which one sialic acid is lost upon the MS measurement, were detected. In the MS measurement of the purified trastuzumab-G2, m/z=2916.7, in which a complex type N-glycan that was a G2 N-glycan linked to Bz-Glu-Glu-Gln-Tyr-Asn-Ser-Thr-Tyr-Arg (SEQ ID NO: 8), was detected. In the MS measurement of the purified trastuzumab-G0, m/z=2592.7, in which a complex type N-glycan that was a G0 (GN2) N-glycan linked to Bz-Glu-Glu-Gln-Tyr-Asn-Ser-Thr-Tyr-Arg (SEQ ID NO: 8), was detected. In the MS measurement of the purified trastuzumab-M3, m/z=2186.5, in which a mannose type N-glycan that was a M3 N-glycan linked to Bz-Glu-Glu-Gln-Tyr-Asn-Ser-Thr-Tyr-Arg (SEQ ID NO: 8), was detected (FIG. 17). From these results, it was confirmed that glycoengineered antibodies having homogeneous N-glycans (A2 form, G2 form, G0 form, and M3 form) could be prepared.

Example 15

Binding Test of Glycoengineered Antibodies to FcγRIIIa-V158

With reference to the report of LG. Presta et al. (J. Biol. Chem. (2001) 276, 6591-6604), a binding test was carried out to examine the binding of each glycoengineered trastuzumab (A2 form, G2 form, G0 form, and M3 form) to FcγRIIIa-V158. A humanized FcγRIIIa-V158 solution (manufactured by Novoprotein, 10 μg/ml of PBS, 100 μl) was added to an ELISA microplate (manufactured by Thermoscientific), and it was then immobilized at 4° C. overnight and was then blocked with a 50 mM Tris-HCl buffer solution (pH 8.0) containing a 0.14 M saline, 1% BSA and 0.05% Tween 20. Between the steps, the resultant was washed with a 50 mM Tris-HCl buffer solution (pH 8.0) containing a 0.14 M saline and 0.05% Tween 20, five times. Subsequently, the purified glycoengineered trastuzumabs (A2 form, G2 form, G0 form, and M3 form), native trastuzumab (intact form), an antibody whose N-glycans are cleaved by PNGaseF (aglycon form), and trastuzumab produced by CHO cells (CHO form, manufactured by F. Hoffmann-La Roche) were each diluted with a 50 mM Tris-HCl buffer solution (pH 8.0) that contained a 0.14 M saline, 1% BSA and 0.05% Tween 20. Each diluted solution (100 μl) was added to a plate well in which humanized FcγRIIIa-V158 had been immobilized, and they were allowed to bind to each other at 27° C. for 2 hours. Thereafter, an antibody solution was removed from the plate, and was then fully washed. Thereafter, the amount of an antibody binding to the plate was detected using HRP Conjugate Protein G (manufactured by Bio-rad). As a dye reagent, a TMB solution (manufactured by eBioscience) was allowed to react therewith, and the reaction product was then quenched with a 0.18 M sulfuric acid aqueous solution. Thereafter, the wavelength at 450 nm was detected using a plate reader.

Figure 18:
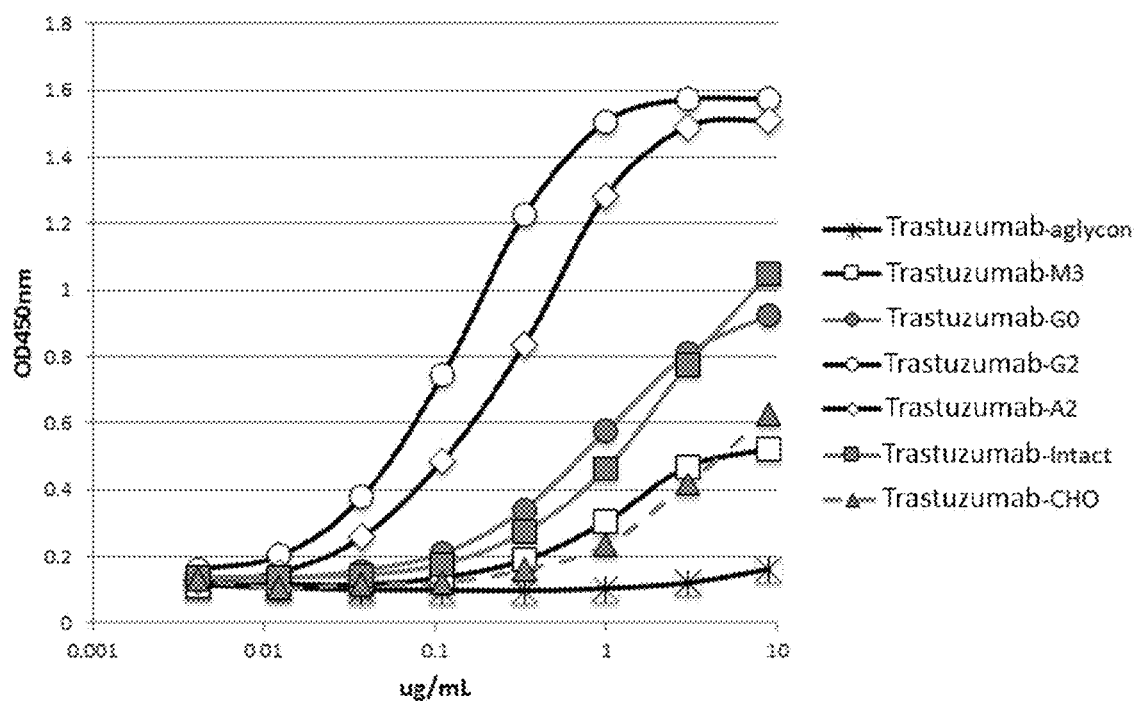
FIG. 18 is a graph of the results of a binding test of glycoengineered antibodies (A2 form, G2 form, G0 form, and M3 form), a native antibody (intact form), a N-glycan-cleaved antibody (aglycon form), and trastuzumab produced from CHO cells (CHO form) to FcγRIIIa-V158. (Longitudinal axis: OD 450 nm; and horizontal axis: protein concentration (μg/ml)).

The results are shown in FIG. 18. From these results, it was found that the presence or absence of N-glycans linked to an antibody and the types thereof are largely associated with the binding of the antibody to FcγRIIIa-V158. In addition, it was also found that trastuzumab having no without core fucose binds to FcγRIIIa-V158, more strongly than trastuzumab (CHO form) produced by CHO cells does. Moreover, it was further found that a change in N-glycans other than the presence or absence of core fucose also has a great influence on the binding activity of the antibody to FcγRIIIa-V158. In particular, it was demonstrated that the binding activity of a G2 or A2 N-glycan form is excellent in comparison to intact form having no core fucose, and that such a binding activity is not simply caused by the absence of fucose, but that these N-glycan structures themselves directly contribute to the binding activity of the antibody to the humanized FcγRIIIa-V158.

Example 16

ADCC Reporter Test of Glycoengineered Antibodies

Using ADCC Reporter Bioassay Kit manufactured by Promega, antibody-dependent cellular cytotoxicity (ADCC) on glycoengineered trastuzumabs (A2 form, G2 form, G0 form, and M3 form) was measured.

As target cells, human breast cancer cells (SKBR-3) in which a Her2 receptor is expressed at a high level, and nude mouse transplantable human breast cancer cells (BT-474) were used. As effector cells, genetically recombinant Jurkat cells, which stably express a V158 variant of the Fc-γ receptor IIIa and stably retains a NFAT response sequence for driving the expression of firefly luciferase, were used.

Figure 19:
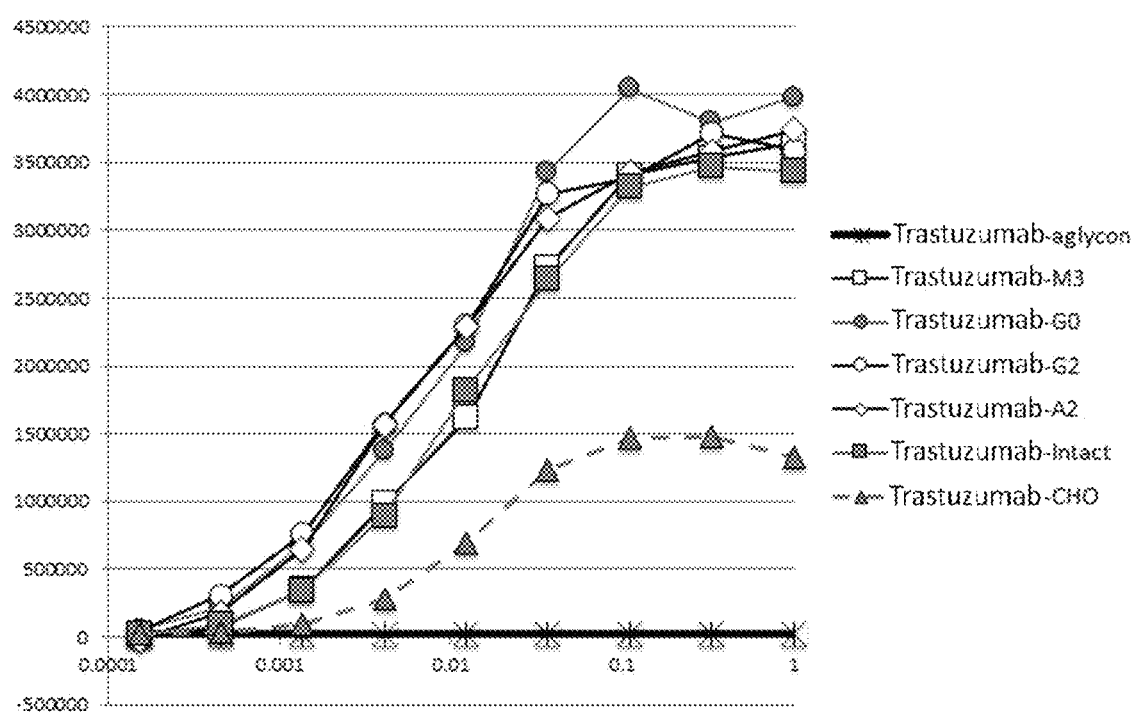
FIG. 19 is a graph of the results of an ADCC reporter assay of glycoengineered antibodies (A2 form, G2 form, G0 form, and M3 form), a native antibody (intact form), a N-glycan-cleaved antibody (aglycon form), and trastuzumab produced from CHO cells (CHO form), using SKBR-3 as target cells. (Longitudinal axis: luciferase activity: fluorescence amount (RLU); and horizontal axis: protein concentration (μg/ml)).
Figure 20:
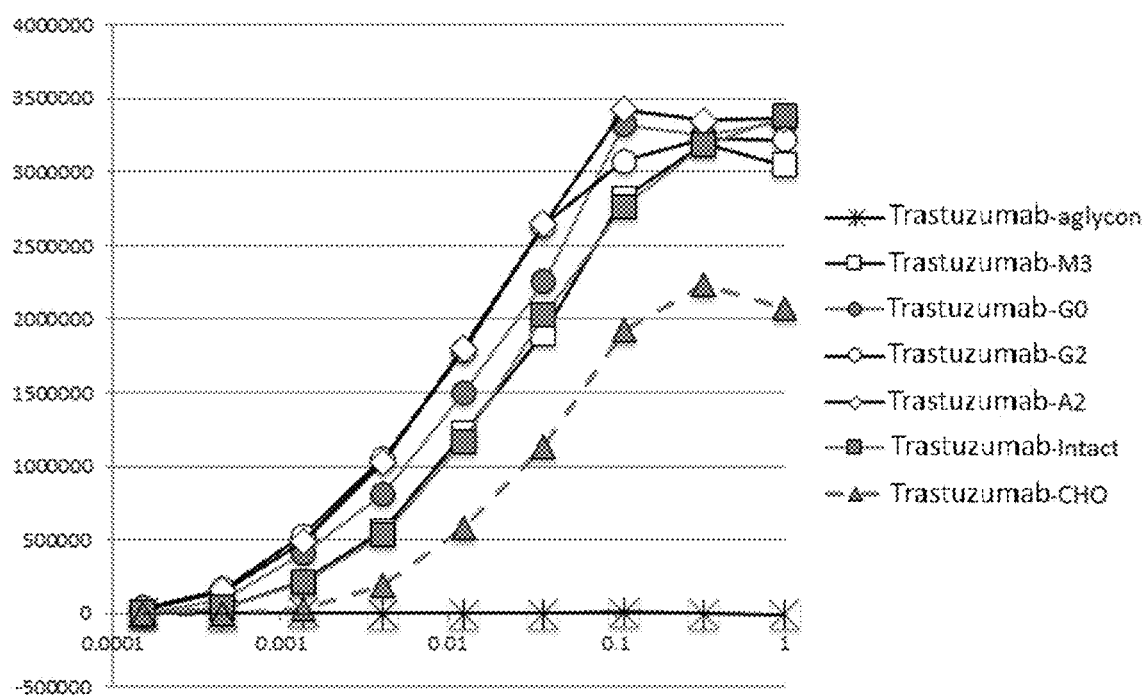
FIG. 20 is a graph of the results of an ADCC reporter assay of glycoengineered antibodies (A2 form, G2 form, G0 form, and M3 form), a native antibody (intact form), a N-glycan-cleaved antibody (aglycon form), and trastuzumab produced from CHO cells (CHO form), using BT-474 as target cells. (Longitudinal axis: luciferase activity: fluorescence amount (RLU); and horizontal axis: protein concentration (μg/ml)).

SKBR-3 cells and BT-474 cells were each cultured in a RPMI medium containing 10% FBS, and thereafter, the cells were subcultured in an amount of 1,500 cells per well of a 96-well plate. The resulting cells were washed with 100 μL of a serum-free RPMI1640 medium, and the medium was then exchanged with 50 μL of an ADCC assay medium (RPMI1640+MEM-NEAA (essential amino acids)+4% Super-low IgG FBS (manufactured by Hyclone)). Then, the cells were cultured overnight. Subsequently, using purified glycoengineered trastuzumabs (A2 form, G2 form, G0 form, and M3 form), native trastuzumab (intact form), an antibody whose N-glycans are hydrolyzed by PNGaseF (aglycon form), and trastuzumab produced by CHO cells (CHO form, manufactured by F. Hoffmann-La Roche) were diluted with an ADCC assay medium. The thus obtained solutions (25 μl) having different concentrations were each added to a well containing the target cells, and the obtained mixture was then left at rest at 37° C. for 30 minutes. In order to set the ratio of effector cells:target cells at 50:1, Jurkat ADCC reporter cells were suspended in an ADCC assay medium, and the thus obtained solution (25 μl) was added to the plate in an amount of 75,000 cells per well. The cells were left at rest at 37° C. in a 5% CO2 incubator for 20 hours. Thereafter, a Bio-Glo luciferase reaction solution (manufactured by Promega) was added to the culture solution in an amount equal to the culture solution, and the obtained mixture was then reacted for 15 minutes at room temperature. Thereafter, the chemical fluorescence of luciferase was detected. The results are shown in FIG. 19 and FIG. 20.

As a result of the analysis, the antibodies having N-glycans with no core fucose exhibited extremely high ADCC, in comparison to the trastuzumab produced by CHO cells (CHO form). When an antibody having mannose at a non-reducing end was compared with an antibody having complex type N-glycans, the antibody having complex type N-glycans exhibited stronger ADCC. It was found that there is a small difference in response to ADCC activity between SKBR-3 and BT-474.

The invention claimed is:

1. A method for preparing a N-glycan hydrolyzed antibody or a Fc thereof, comprising reacting the antibody or the Fc thereof with several endoglycosidases, wherein each of the several endoglycosidases hydrolyzes N-glycans linked to the antibody or the Fc thereof; and obtaining a N-glycan hydrolyzed antibody or a Fc thereof.

2. The method of claim 1, wherein said several endoglycosidases are a combination of endoglycosidases having different substrate specificity that are classified into EC3.2.1.96.

3. The method of claim 2, wherein said several endoglycosidases are two or more types of endoglycosidases selected from the group consisting of endoglycosidase D, endoglycosidase H, endoglycosidase S, endoglycosidase M, endoglycosidase LL, endoglycosidase F1, endoglycosidase F2, and endoglycosidase F3.

4. The method of claim 3, wherein said several endoglycosidases are any one combination of the following (i) to (Xi):
(i) endoglycosidase D and endoglycosidase S,
(ii) endoglycosidase S and endoglycosidase LL,
(iii) endoglycosidase D and endoglycosidase LL,
(iv) endoglycosidase D and endoglycosidase H,
(v) endoglycosidase S and endoglycosidase H,
(vi) endoglycosidase F1 and endoglycosidase F2,
(vii) endoglycosidase F1 and endoglycosidase F3,
(viii) endoglycosidase F2 and endoglycosidase F3,
(iX) endoglycosidase D, endoglycosidase S and endoglycosidase LL,
(X) endoglycosidase D, endoglycosidase S and endoglycosidase H, and
(Xi) endoglycosidase D, endoglycosidase S and endoglycosidase F1.

5. The method of claim 1, wherein the N-glycans hydrolyzed antibody or the Fc thereof is an antibody or a Fc thereof whose N-glycans are hydrolyzed other than N-acetylglucosamine that directly attaches to the antibody or the Fc thereof.

6. The method of claim 5, wherein the N-glycans hydrolyzed antibody or the Fc thereof is an antibody or a Fc thereof whose N-glycans are hydrolyzed other than N-acetylglucosamine that directly attaches to the asparagine at position 297 of an IgG antibody.

7. The method of claim 1, further comprising selecting said several endoglycosidases by determining a combination of two or more types of endoglycosidases suitable for hydrolyzing N-glycans linked to an antibody by
  determining information of the hydrolyzed amount of two or more types of objective N-glycans with desired structure that heterogeneously attach to an antibody or a Fc thereof by endoglycosidases according to the following method:
    (a) reacting the antibody or the Fc thereof with endoglycosidases,
    (b) treating the endoglycosidases reacted antibody or the Fc thereof with protease to produce a glycopeptide,
    (c) treating the endoglycosidases non-reacted antibody or the Fc thereof with protease to produce a glycopeptide,
    (d) quantifying the glycopeptide having objective N-glycans that are obtained by treating the endoglycosidases treated antibody or the Fc thereof with protease in said treatment step (b),
    (e) quantifying the glycopeptide having objective N-glycans that are obtained by treating the endoglycosidases non-treated antibody or the Fc thereof with protease in said protease treatment step (c), and
    (f) determining information of the hydrolyzed amount of each of the objective N-glycans hydrolyzed by endoglycosidases calculated from quantitative value obtained in the quantification step for the antibody or the Fc thereof reacted with endoglycosidases and for the antibody or the Fc thereof not reacted with endoglycosidases;
  selecting a combination of two or more types of endoglycosidases showing complementary N-glycan hydrolysis from the obtained information of the hydrolyzed amount of objective N-glycans by endoglycosidases, and
  determining the selected two or more types of endoglycosidases as a combination of endoglycosidases suitable for hydrolyzing the N-glycans linked to the antibody.

8. The method of claim 1, wherein the antibody is an antibody produced by silkworms.

9. The method of claim 1, wherein the antibody is a non-human antibody, a chimeric antibody, a humanized antibody, or a human antibody.

10. A method for preparing an antibody or a Fc thereof having a desired homogeneous N-glycan, comprising:
  an acceptor preparation step comprising preparing an acceptor antibody or a Fc thereof that is an antibody or a Fc thereof whose N-glycans are hydrolyzed by the method of claim 1, and
  an antibody remodeling step comprising reacting the acceptor antibody or the Fc thereof with a glycosyl donor using glycosynthase to synthesize the antibody or the Fc thereof having the desired homogeneous N-glycan.

11. The method of claim 10, wherein the desired homogeneous N-glycan is high mannose type N-glycans or complex type N-glycans.

* * * * *

(12) EX PARTE REEXAMINATION CERTIFICATE (11814th)
United States Patent
Shirai et al.

(10) Number: US 9,550,834 C1
(45) Certificate Issued: Mar. 9, 2021

(54) METHODS FOR PREPARING GLYCAN-HYDROLYZED ANTIBODY, AND HOMOGENEOUS GLYCOSYLATED ANTIBODY

(71) Applicants: THE NOGUCHI INSTITUTE, Tokyo (JP); IMMUNO-BIOLOGICAL LABORATORIES CO., LTD., Fujioka (JP)

(72) Inventors: Takashi Shirai, Tokyo (JP); Masako Mori, Tokyo (JP); Masaki Kurogochi, Tokyo (JP); Masahiro Tomita, Fujioka (JP)

(73) Assignees: THE NOGUCHI INSTITUTE, Tokyo (JP); IMMUNO-BIOLOGICAL LABORATORIES CO., LTD., Fujioka (JP)

Reexamination Request:
No. 90/014,428, Jan. 2, 2020

Reexamination Certificate for:
Patent No.: 9,550,834
Issued: Jan. 24, 2017
Appl. No.: 14/690,028
Filed: Apr. 17, 2015

(30) Foreign Application Priority Data

Apr. 25, 2014 (JP) ................................ 2014-091157
Oct. 31, 2014 (JP) ................................ 2014-222191

(51) Int. Cl.
*C07K 16/32* (2006.01)
*C12Q 1/37* (2006.01)

(52) U.S. Cl.
CPC ................ *C07K 16/32* (2013.01); *C12Q 1/37* (2013.01); *C07K 2317/14* (2013.01); *C07K 2317/21* (2013.01); *C07K 2317/24* (2013.01); *C07K 2317/41* (2013.01); *C07K 2317/72* (2013.01); *C07K 2317/732* (2013.01); *C12Y 302/01096* (2013.01); *G01N 2333/924* (2013.01); *G01N 2400/02* (2013.01)

(58) Field of Classification Search
None
See application file for complete search history.

(56) References Cited

To view the complete listing of prior art documents cited during the proceeding for Reexamination Control Number 90/014,428, please refer to the USPTO's public Patent Application Information Retrieval (PAIR) system under the Display References tab.

*Primary Examiner* — Sharon Turner

(57) ABSTRACT

The present invention is aimed to provide a method for preparing an acceptor that is N-glycan hydrolyzed antibody or a Fc fragment thereof used for producing antibody having a homogeneous N-glycan structure; a method for determining a combination of endoglycosidases for use in said preparation; and a method for measuring N-glycans linked to an antibody. The present invention is directed to a method for producing a N-glycan hydrolyzed antibody or Fc fragment thereof, comprising reacting the antibody or the Fc fragment thereof with several endoglycosidases; and a method for determining quantitative information of an objective N-glycan with a desired structure linked to an antibody or a Fc thereof, comprising a protease treatment step and a glycopeptide measurement step, etc.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-6 and 9-11 are cancelled.

Claims 7 and 8 were not reexamined.

\* \* \* \* \*

SEQUENCE LISTING

<160> NUMBER OF SEQ ID NOS: 8

<210> SEQ ID NO 1
<211> LENGTH: 2769
<212> TYPE: DNA
<213> ORGANISM: Lactococcus lactis subsp. Lactis MAFF 516032
<220> FEATURE:
<221> NAME/KEY: CDS
<222> LOCATION: (1)..(2766)

<400> SEQUENCE: 1

```
aaa aaa tcg aaa aaa att ttt att aga ata tgc ctt ttt aca gga att        48
Lys Lys Ser Lys Lys Ile Phe Ile Arg Ile Cys Leu Phe Thr Gly Ile
1               5                   10                  15 ttg gca tct gca act tta ctg aca gct tgt ttt gga act tca gca aaa        96
Leu Ala Ser Ala Thr Leu Leu Thr Ala Cys Phe Gly Thr Ser Ala Lys
            20                  25                  30 cat gtg aaa gct aat tat aaa gtg aca gca gaa gca att cca gat tac       144
His Val Lys Ala Asn Tyr Lys Val Thr Ala Glu Ala Ile Pro Asp Tyr
        35                  40                  45 caa agt aag aat gct ccc att tca tct tat tgg atg cct gat aaa ttt       192
Gln Ser Lys Asn Ala Pro Ile Ser Ser Tyr Trp Met Pro Asp Lys Phe
    50                  55                  60 cta gaa tgg tca gcg gaa aat gac aaa gat tta gtt tac aat caa tcc       240
Leu Glu Trp Ser Ala Glu Asn Asp Lys Asp Leu Val Tyr Asn Gln Ser
65                  70                  75                  80 cga gtg cca ctt acc aaa aga att tct cct gat aaa cta agt cca tcc       288
Arg Val Pro Leu Thr Lys Arg Ile Ser Pro Asp Lys Leu Ser Pro Ser
                85                  90                  95 aat caa aat cag aac aaa aag aca aaa att gtc gcc tta tcg atg atg       336
Asn Gln Asn Gln Asn Lys Lys Thr Lys Ile Val Ala Leu Ser Met Met
            100                 105                 110 aac tca caa act tct gga aat cct tcg cgg ggc acg aca aaa ttt gag       384
Asn Ser Gln Thr Ser Gly Asn Pro Ser Arg Gly Thr Thr Lys Phe Glu
        115                 120                 125 agc tat act ttt gat tat tgg caa tac att gac aca ctg gtt tat tgg       432
Ser Tyr Thr Phe Asp Tyr Trp Gln Tyr Ile Asp Thr Leu Val Tyr Trp
    130                 135                 140 ggt ggc tca tct ggt gaa gga ata att gta act cca tca gca gat gtt       480
Gly Gly Ser Ser Gly Glu Gly Ile Ile Val Thr Pro Ser Ala Asp Val
145                 150                 155                 160 att gat gaa gca cac agc aat ggt gtt ccg gta ctt gga aca att ttc       528
Ile Asp Glu Ala His Ser Asn Gly Val Pro Val Leu Gly Thr Ile Phe
                165                 170                 175
```

```
tta ccg cct aaa gaa tac ggt gga aaa gta gat tgg gtc aaa aca atg      576
Leu Pro Pro Lys Glu Tyr Gly Gly Lys Val Asp Trp Val Lys Thr Met
            180                 185                 190 ctc aaa aaa gat gag caa gga caa tat cca ttt gcc agt caa atg gtt      624
Leu Lys Lys Asp Glu Gln Gly Gln Tyr Pro Phe Ala Ser Gln Met Val
        195                 200                 205 aag gtt gcc aag act tat gga ttt gag gga tgg ttt atc aat gaa gaa      672
Lys Val Ala Lys Thr Tyr Gly Phe Glu Gly Trp Phe Ile Asn Glu Glu
    210                 215                 220 acc caa ggg cta aat gct gac gat gca gct aac atg aaa gcc ttg att      720
Thr Gln Gly Leu Asn Ala Asp Asp Ala Ala Asn Met Lys Ala Leu Ile
225                 230                 235                 240 caa cag gtg aaa aaa gaa gat tct agt ctt caa atc atg tgg tat gat      768
Gln Gln Val Lys Lys Glu Asp Ser Ser Leu Gln Ile Met Trp Tyr Asp
                245                 250                 255 gcc atg act aaa gat gga aaa gtg gat tgg caa aat cag tta aat gac      816
Ala Met Thr Lys Asp Gly Lys Val Asp Trp Gln Asn Gln Leu Asn Asp
            260                 265                 270 caa aat gcg aca ttt gta caa gat aaa gca gca gac gcg atg ttt tta      864
Gln Asn Ala Thr Phe Val Gln Asp Lys Ala Ala Asp Ala Met Phe Leu
        275                 280                 285 aat ttc tgg tgg act caa aat aat ttg gcc gac caa aaa tta ctt gaa      912
Asn Phe Trp Trp Thr Gln Asn Asn Leu Ala Asp Gln Lys Leu Leu Glu
    290                 295                 300 aaa tcg aat ctc tat gct aaa aat cac aat att gac cct tat aat att      960
Lys Ser Asn Leu Tyr Ala Lys Asn His Asn Ile Asp Pro Tyr Asn Ile
305                 310                 315                 320 tat gcc gga ata gat gtg caa gcg aaa gac gtc caa act cca gtt aaa     1008
Tyr Ala Gly Ile Asp Val Gln Ala Lys Asp Val Gln Thr Pro Val Lys
                325                 330                 335 tgg aac ctt tta gaa aaa gga aat caa gcc act caa aca tca att gga     1056
Trp Asn Leu Leu Glu Lys Gly Asn Gln Ala Thr Gln Thr Ser Ile Gly
            340                 345                 350 ctc tat gca gca agc gct acc tat act aac gca agt aat tgg gat gat     1104
Leu Tyr Ala Ala Ser Ala Thr Tyr Thr Asn Ala Ser Asn Trp Asp Asp
        355                 360                 365 ttt caa aat cgt gaa tca gca ttc tgg gtc aat caa aaa gca gac cct     1152
Phe Gln Asn Arg Glu Ser Ala Phe Trp Val Asn Gln Lys Ala Asp Pro
    370                 375                 380 cgt caa gtt gat cac tct gtt aat gaa tca tgg aca gga ctt tcc aaa     1200
Arg Gln Val Asp His Ser Val Asn Glu Ser Trp Thr Gly Leu Ser Lys
385                 390                 395                 400 tat gtt ctg gaa aaa tca gca ata agc ggt aat gaa ttt aat act aat     1248
Tyr Val Leu Glu Lys Ser Ala Ile Ser Gly Asn Glu Phe Asn Thr Asn
                405                 410                 415 ttt aat tta gga aat ggt tat aac tat ttt aaa gct ggt caa aaa atc     1296
Phe Asn Leu Gly Asn Gly Tyr Asn Tyr Phe Lys Ala Gly Gln Lys Ile
            420                 425                 430 tca gaa atg gat tgg aac gac cgc agt tta gca ggt att tta cca tct     1344
Ser Glu Met Asp Trp Asn Asp Arg Ser Leu Ala Gly Ile Leu Pro Ser
        435                 440                 445 tac cgc tgg att att gac aac gaa gga aaa aat aaa ata agt cca agc     1392
Tyr Arg Trp Ile Ile Asp Asn Glu Gly Lys Asn Lys Ile Ser Pro Ser
    450                 455                 460 ttc gac ttt gca aat gct tat aac ggt gga aat tca ctg aaa ttt atg     1440
Phe Asp Phe Ala Asn Ala Tyr Asn Gly Gly Asn Ser Leu Lys Phe Met
465                 470                 475                 480 gct gaa cat tta gat gca ggg aaa agc tca aac atc aca ttg ttt gct     1488
Ala Glu His Leu Asp Ala Gly Lys Ser Ser Asn Ile Thr Leu Phe Ala
```

|  |  |  |  |  |  |  |  |  |  |  |  |  |  |  |  |
|---|---|---|---|---|---|---|---|---|---|---|---|---|---|---|---|
|  |  | 485 |  |  |  |  | 490 |  |  |  |  | 495 |  |  |  |
| agt | gat | ttg | aaa | att | gat | aag | gga | gca | aaa | ttc | tct | gtt | agt | atg | cgc |
| Ser | Asp | Leu | Lys | Ile | Asp | Lys | Gly | Ala | Lys | Phe | Ser | Val | Ser | Met | Arg |
|  |  | 500 |  |  |  |  | 505 |  |  |  |  | 510 |  |  |  |

1536 tca gac caa gcg ctt aaa gtt tct gca atc tta gaa cta gca aat ggt  1584
Ser Asp Gln Ala Leu Lys Val Ser Ala Ile Leu Glu Leu Ala Asn Gly
         515                 520                 525 caa aaa gtt agc att aca gga gat aaa agc ctg act gag aat tgg tca  1632
Gln Lys Val Ser Ile Thr Gly Asp Lys Ser Leu Thr Glu Asn Trp Ser
530                 535                 540 gaa ata agt ttt gat gtt aag aaa ttt gaa ggt caa aca atc aaa aaa  1680
Glu Ile Ser Phe Asp Val Lys Lys Phe Glu Gly Gln Thr Ile Lys Lys
545                 550                 555                 560 atc ggt tta agc ata aaa tct gat caa gca atg gat ttt aaa gcc att  1728
Ile Gly Leu Ser Ile Lys Ser Asp Gln Ala Met Asp Phe Lys Ala Ile
                 565                 570                 575 aat cta gga gaa atg act ttg acc act ggt caa aaa gtc gct cca atc  1776
Asn Leu Gly Glu Met Thr Leu Thr Thr Gly Gln Lys Val Ala Pro Ile
         580                 585                 590 gta ctt tcg gat gca aaa gta act gat gaa gct ttt gaa gaa gaa gga  1824
Val Leu Ser Asp Ala Lys Val Thr Asp Glu Ala Phe Glu Glu Glu Gly
         595                 600                 605 aca gta ggc ggt ttt aga ctt tct tgg aaa tca gat gca act aaa aat  1872
Thr Val Gly Gly Phe Arg Leu Ser Trp Lys Ser Asp Ala Thr Lys Asn
610                 615                 620 aat ttt tct act tat gaa atc tat cag ttg aat gat gat gga agt aaa  1920
Asn Phe Ser Thr Tyr Glu Ile Tyr Gln Leu Asn Asp Asp Gly Ser Lys
625                 630                 635                 640 gaa ttt tta gga gca agc aat atc aat gcc ttc ttt gtt aat gcc tta  1968
Glu Phe Leu Gly Ala Ser Asn Ile Asn Ala Phe Phe Val Asn Ala Leu
                 645                 650                 655 aaa cgc ggc aaa aat atc aat tca aca aaa ttt gaa att gtc cca att  2016
Lys Arg Gly Lys Asn Ile Asn Ser Thr Lys Phe Glu Ile Val Pro Ile
         660                 665                 670 aat aag gct gga gaa tct gga cat tca gtt acg acc tct gtg aaa tgg  2064
Asn Lys Ala Gly Glu Ser Gly His Ser Val Thr Thr Ser Val Lys Trp
         675                 680                 685 cca gat aat tca tta gct aaa gcg gca ttt gta gca gat aaa acc cta  2112
Pro Asp Asn Ser Leu Ala Lys Ala Ala Phe Val Ala Asp Lys Thr Leu
690                 695                 700 gtt acg att ggt gaa aaa gta act tta atg aat caa tct aat tta gct  2160
Val Thr Ile Gly Glu Lys Val Thr Leu Met Asn Gln Ser Asn Leu Ala
705                 710                 715                 720 tcc gtc aaa tat aaa tgg gaa att gac ggt gca agt ccc gct act tct  2208
Ser Val Lys Tyr Lys Trp Glu Ile Asp Gly Ala Ser Pro Ala Thr Ser
                 725                 730                 735 aca gaa aag aat cct caa gta agt ttt gat aaa gca ggg agt tat tcc  2256
Thr Glu Lys Asn Pro Gln Val Ser Phe Asp Lys Ala Gly Ser Tyr Ser
         740                 745                 750 gtc aaa tta acg gcc atc aat gaa aaa gga caa gaa gat tca gtc act  2304
Val Lys Leu Thr Ala Ile Asn Glu Lys Gly Gln Glu Asp Ser Val Thr
         755                 760                 765 caa act gaa ctg att act gta att gat caa cca gta gaa tta aca aat  2352
Gln Thr Glu Leu Ile Thr Val Ile Asp Gln Pro Val Glu Leu Thr Asn
770                 775                 780 ttt gca tta aat caa tcc gtt caa gta gac agt ttc act aat gaa tct  2400
Phe Ala Leu Asn Gln Ser Val Gln Val Asp Ser Phe Thr Asn Glu Ser
785                 790                 795                 800 gaa tca gga cca aaa gca gtt gat gga aaa tta aat acc aaa tgg tgt  2448

```
Glu Ser Gly Pro Lys Ala Val Asp Gly Lys Leu Asn Thr Lys Trp Cys
                805                 810                 815 gcc gtt ggc acg ggt aaa cac aat att aca att gac ctt ggg aaa tca        2496
Ala Val Gly Thr Gly Lys His Asn Ile Thr Ile Asp Leu Gly Lys Ser
            820                 825                 830 gaa aaa atc aat caa gtc ctg att gac cat gct caa aaa gga gga gaa        2544
Glu Lys Ile Asn Gln Val Leu Ile Asp His Ala Gln Lys Gly Gly Glu
        835                 840                 845 tca cct gac atg aat act tct gat tac acc att gag att tca aag gat        2592
Ser Pro Asp Met Asn Thr Ser Asp Tyr Thr Ile Glu Ile Ser Lys Asp
    850                 855                 860 aat caa aat tgg aca gaa gtt gtc aac gtt aag aaa aat aaa ttg ggg        2640
Asn Gln Asn Trp Thr Glu Val Val Asn Val Lys Lys Asn Lys Leu Gly
865                 870                 875                 880 gaa acc aaa gat tct ttc aaa cag aca gaa gcg cgg tac gtt agg atc        2688
Glu Thr Lys Asp Ser Phe Lys Gln Thr Glu Ala Arg Tyr Val Arg Ile
                885                 890                 895 aca gcc att aaa cca aca caa gga gca gat acc gct gtt cgt tta tat        2736
Thr Ala Ile Lys Pro Thr Gln Gly Ala Asp Thr Ala Val Arg Leu Tyr
            900                 905                 910 gaa ata caa gta tta gga caa aaa aat agc taa                            2769
Glu Ile Gln Val Leu Gly Gln Lys Asn Ser
        915                 920

<210> SEQ ID NO 2
<211> LENGTH: 922
<212> TYPE: PRT
<213> ORGANISM: Lactococcus lactis subsp. Lactis MAFF 516032

<400> SEQUENCE: 2

Lys Lys Ser Lys Lys Ile Phe Ile Arg Ile Cys Leu Phe Thr Gly Ile
1               5                   10                  15

Leu Ala Ser Ala Thr Leu Leu Thr Ala Cys Phe Gly Thr Ser Ala Lys
            20                  25                  30

His Val Lys Ala Asn Tyr Lys Val Thr Ala Glu Ala Ile Pro Asp Tyr
        35                  40                  45

Gln Ser Lys Asn Ala Pro Ile Ser Ser Tyr Trp Met Pro Asp Lys Phe
    50                  55                  60

Leu Glu Trp Ser Ala Glu Asn Asp Lys Asp Leu Val Tyr Asn Gln Ser
65                  70                  75                  80

Arg Val Pro Leu Thr Lys Arg Ile Ser Pro Asp Lys Leu Ser Pro Ser
                85                  90                  95

Asn Gln Asn Gln Asn Lys Lys Thr Lys Ile Val Ala Leu Ser Met Met
            100                 105                 110

Asn Ser Gln Thr Ser Gly Asn Pro Ser Arg Gly Thr Thr Lys Phe Glu
        115                 120                 125

Ser Tyr Thr Phe Asp Tyr Trp Gln Tyr Ile Asp Thr Leu Val Tyr Trp
    130                 135                 140

Gly Gly Ser Ser Gly Glu Gly Ile Ile Val Thr Pro Ser Ala Asp Val
145                 150                 155                 160

Ile Asp Glu Ala His Ser Asn Gly Val Pro Val Leu Gly Thr Ile Phe
                165                 170                 175

Leu Pro Pro Lys Glu Tyr Gly Gly Lys Val Asp Trp Val Lys Thr Met
            180                 185                 190

Leu Lys Lys Asp Glu Gln Gly Gln Tyr Pro Phe Ala Ser Gln Met Val
        195                 200                 205

Lys Val Ala Lys Thr Tyr Gly Phe Glu Gly Trp Phe Ile Asn Glu Glu
```

```
              210                 215                 220
Thr Gln Gly Leu Asn Ala Asp Ala Ala Asn Met Lys Ala Leu Ile
225                 230                 235                 240

Gln Gln Val Lys Lys Glu Asp Ser Ser Leu Gln Ile Met Trp Tyr Asp
                245                 250                 255

Ala Met Thr Lys Asp Gly Lys Val Asp Trp Gln Asn Gln Leu Asn Asp
                    260                 265                 270

Gln Asn Ala Thr Phe Val Gln Asp Lys Ala Ala Asp Ala Met Phe Leu
                275                 280                 285

Asn Phe Trp Trp Thr Gln Asn Leu Ala Asp Gln Lys Leu Leu Glu
            290                 295                 300

Lys Ser Asn Leu Tyr Ala Lys Asn His Asn Ile Asp Pro Tyr Asn Ile
305                 310                 315                 320

Tyr Ala Gly Ile Asp Val Gln Ala Lys Asp Val Gln Thr Pro Val Lys
                    325                 330                 335

Trp Asn Leu Leu Glu Lys Gly Asn Gln Ala Thr Gln Thr Ser Ile Gly
                340                 345                 350

Leu Tyr Ala Ala Ser Ala Thr Tyr Thr Asn Ala Ser Asn Trp Asp Asp
            355                 360                 365

Phe Gln Asn Arg Glu Ser Ala Phe Trp Val Asn Gln Lys Ala Asp Pro
        370                 375                 380

Arg Gln Val Asp His Ser Val Asn Glu Ser Trp Thr Gly Leu Ser Lys
385                 390                 395                 400

Tyr Val Leu Glu Lys Ser Ala Ile Ser Gly Asn Glu Phe Asn Thr Asn
                405                 410                 415

Phe Asn Leu Gly Asn Gly Tyr Asn Tyr Phe Lys Ala Gly Gln Lys Ile
                420                 425                 430

Ser Glu Met Asp Trp Asn Asp Arg Ser Leu Ala Gly Ile Leu Pro Ser
            435                 440                 445

Tyr Arg Trp Ile Ile Asp Asn Glu Gly Lys Asn Lys Ile Ser Pro Ser
450                 455                 460

Phe Asp Phe Ala Asn Ala Tyr Asn Gly Gly Asn Ser Leu Lys Phe Met
465                 470                 475                 480

Ala Glu His Leu Asp Ala Gly Lys Ser Ser Asn Ile Thr Leu Phe Ala
                485                 490                 495

Ser Asp Leu Lys Ile Asp Lys Gly Ala Lys Phe Ser Val Ser Met Arg
                500                 505                 510

Ser Asp Gln Ala Leu Lys Val Ser Ala Ile Leu Glu Leu Ala Asn Gly
                515                 520                 525

Gln Lys Val Ser Ile Thr Gly Asp Lys Ser Leu Thr Glu Asn Trp Ser
            530                 535                 540

Glu Ile Ser Phe Asp Val Lys Lys Phe Glu Gly Gln Thr Ile Lys Lys
545                 550                 555                 560

Ile Gly Leu Ser Ile Lys Ser Asp Gln Ala Met Asp Phe Lys Ala Ile
                565                 570                 575

Asn Leu Gly Glu Met Thr Leu Thr Thr Gly Gln Lys Val Ala Pro Ile
                580                 585                 590

Val Leu Ser Asp Ala Lys Val Thr Asp Glu Ala Phe Glu Glu Gly
                595                 600                 605

Thr Val Gly Gly Phe Arg Leu Ser Trp Lys Ser Asp Ala Thr Lys Asn
            610                 615                 620

Asn Phe Ser Thr Tyr Glu Ile Tyr Gln Leu Asn Asp Asp Gly Ser Lys
625                 630                 635                 640
```

Glu Phe Leu Gly Ala Ser Asn Ile Asn Ala Phe Val Asn Ala Leu
                645                 650                 655

Lys Arg Gly Lys Asn Ile Asn Ser Thr Lys Phe Glu Ile Val Pro Ile
                660                 665                 670

Asn Lys Ala Gly Glu Ser Gly His Ser Val Thr Thr Ser Val Lys Trp
            675                 680                 685

Pro Asp Asn Ser Leu Ala Lys Ala Ala Phe Val Ala Asp Lys Thr Leu
        690                 695                 700

Val Thr Ile Gly Glu Lys Val Thr Leu Met Asn Gln Ser Asn Leu Ala
705                 710                 715                 720

Ser Val Lys Tyr Lys Trp Glu Ile Asp Gly Ala Ser Pro Ala Thr Ser
                725                 730                 735

Thr Glu Lys Asn Pro Gln Val Ser Phe Asp Lys Ala Gly Ser Tyr Ser
                740                 745                 750

Val Lys Leu Thr Ala Ile Asn Glu Lys Gly Gln Glu Asp Ser Val Thr
            755                 760                 765

Gln Thr Glu Leu Ile Thr Val Ile Asp Gln Pro Val Glu Leu Thr Asn
        770                 775                 780

Phe Ala Leu Asn Gln Ser Val Gln Val Asp Ser Phe Thr Asn Glu Ser
785                 790                 795                 800

Glu Ser Gly Pro Lys Ala Val Asp Gly Lys Leu Asn Thr Lys Trp Cys
                805                 810                 815

Ala Val Gly Thr Gly Lys His Asn Ile Thr Ile Asp Leu Gly Lys Ser
                820                 825                 830

Glu Lys Ile Asn Gln Val Leu Ile Asp His Ala Gln Lys Gly Gly Glu
            835                 840                 845

Ser Pro Asp Met Asn Thr Ser Asp Tyr Thr Ile Glu Ile Ser Lys Asp
        850                 855                 860

Asn Gln Asn Trp Thr Glu Val Val Asn Val Lys Lys Asn Lys Leu Gly
865                 870                 875                 880

Glu Thr Lys Asp Ser Phe Lys Gln Thr Glu Ala Arg Tyr Val Arg Ile
                885                 890                 895

Thr Ala Ile Lys Pro Thr Gln Gly Ala Asp Thr Ala Val Arg Leu Tyr
                900                 905                 910

Glu Ile Gln Val Leu Gly Gln Lys Asn Ser
        915                 920

<210> SEQ ID NO 3
<211> LENGTH: 24
<212> TYPE: DNA
<213> ORGANISM: Artificial Sequence
<220> FEATURE:
<223> OTHER INFORMATION: Sense primer EndoLL-12F

<400> SEQUENCE: 3
ttggaggatt ttatgaaaaa atcg                                    24

<210> SEQ ID NO 4
<211> LENGTH: 27
<212> TYPE: DNA
<213> ORGANISM: Artificial Sequence
<220> FEATURE:
<223> OTHER INFORMATION: Antisense primer EndoLL stopR

<400> SEQUENCE: 4
tcagctattt ttttgtccta atacttg                                 27

```
<210> SEQ ID NO 5
<211> LENGTH: 30
<212> TYPE: DNA
<213> ORGANISM: Artificial Sequence
<220> FEATURE:
<223> OTHER INFORMATION: Sense primer 6P1-EndoLL-F

<400> SEQUENCE: 5
gggcccctgg gatccaaaaa atcgaaaaaa                                    30

<210> SEQ ID NO 6
<211> LENGTH: 30
<212> TYPE: DNA
<213> ORGANISM: Artificial Sequence
<220> FEATURE:
<223> OTHER INFORMATION: Antisense primer 6P1-EndoLL-R

<400> SEQUENCE: 6
atgcggccgc tcgagttagc tattttttg                                     30

<210> SEQ ID NO 7
<211> LENGTH: 9
<212> TYPE: PRT
<213> ORGANISM: Artificial Sequence
<220> FEATURE:
<223> OTHER INFORMATION: IgG1 oligopeptide fragment

<400> SEQUENCE: 7

Glu Glu Gln Phe Asn Ser Thr Phe Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Trastuzumab oligopeptide fragment

<400> SEQUENCE: 8

Glu Glu Gln Tyr Asn Ser Thr Tyr Arg
1               5
```